(12) United States Patent
Nicholson et al.

(10) Patent No.: US 7,373,256 B2
(45) Date of Patent: May 13, 2008

(54) METHOD FOR THE IDENTIFICATION OF MOLECULES AND BIOMARKERS USING CHEMICAL, BIOCHEMICAL AND BIOLOGICAL DATA

(76) Inventors: Jeremy K. Nicholson, 13 Tidenham Gardens, Croydon, Surrey (GB) CR0 UT; Elaine Holmes, 59 Petley Road, London (GB) W6 9SU; Olivier Cloarec, 19 St. Annes Road, London (GB) SW13 9LH; Derek J. Crockford, 29 Longcroft Lane, Welwyn Garden City, Herts. (GB) AL8 6EA; John C. Lindon, 27 Aperfield Road, Biggin Hill, Kent (GB) TN16 3LU; Mattias Rantalainen, 7A Redan Street, London (GB) W14 0AB ( * ) Notice: Subject to any disclaimer, the term of this patent is extended or adjusted under 35 U.S.C. 154(b) by 0 days.

(21) Appl. No.: 11/398,530

(22) Filed: Apr. 6, 2006

(65) Prior Publication Data
US 2007/0043518 A1 Feb. 22, 2007

Related U.S. Application Data

(60) Provisional application No. 60/672,500, filed on Apr. 19, 2005.

(51) Int. Cl.
*G06F 19/00* (2006.01)
(52) U.S. Cl. .............................. 702/19; 702/22; 702/23; 702/27; 702/28; 702/30; 702/32; 702/76
(58) Field of Classification Search .................. 702/22, 702/23, 27, 28, 30, 32, 76, 179, 189; 250/255, 250/339.12; 436/173, 174, 63, 518; 356/301; 324/310, 312
See application file for complete search history.

(56) References Cited

U.S. PATENT DOCUMENTS

| | | | | |
|---|---|---|---|---|
| 4,800,279 A * | 1/1989 | Hieftje et al. | ........... | 250/339.09 |
| 5,121,337 A * | 6/1992 | Brown | ........................ | 702/28 |
| 5,446,681 A * | 8/1995 | Gethner et al. | ................ | 702/27 |
| 5,712,797 A * | 1/1998 | Descales et al. | ............... | 702/30 |
| 5,850,623 A * | 12/1998 | Carman et al. | ................ | 702/28 |
| 6,070,128 A * | 5/2000 | Descales et al. | ............... | 702/30 |
| 7,181,348 B2 * | 2/2007 | Wishart et al. | ................ | 702/22 |
| 7,191,069 B2 * | 3/2007 | Wishart et al. | ................ | 702/22 |
| 2002/0145425 A1 | 10/2002 | Ebbels et al. | | |
| 2003/0129666 A1 * | 7/2003 | Tanaka et al. | ................ | 435/7.2 |

(Continued)

OTHER PUBLICATIONS

Beebe, K.B. et al, 1998, *Chemometrics: A Practical Guide*, John Wiley & Sons: New York, pp. 56-182.

(Continued)

*Primary Examiner*—Carol S. W. Tsai
(74) *Attorney, Agent, or Firm*—Nixon & Vanderhye P.C.

(57) ABSTRACT

This invention pertains generally to the field of multivariate statistics, and in particular to new methods for the analysis (e.g., chemometrics) of chemical, biochemical, and biological data, including, for example, spectral data, including but not limited to nuclear magnetic resonance (NMR) spectral data. These methods are useful, for example, in metabonomics, proteomics, transcriptomics, genomics, etc., and form a part of other methods, for example, methods for the identification of chemical species, methods for the identification of biomarkers that are useful in methods of classification, diagnosis, prognosis, etc.

28 Claims, 25 Drawing Sheets
(18 of 25 Drawing Sheet(s) Filed in Color)

U.S. PATENT DOCUMENTS

2007/0023627 A1* 2/2007 Finch et al. .............. 250/282
2007/0061091 A1* 3/2007 Schweitzer et al. .......... 702/76

OTHER PUBLICATIONS

Braunschweiler, L., et al, 1983, "Coherence transfer by istropic mixing: application to proton correlation spectroscopy", *Magn. Reson.*, vol. 53, pp. 521-528.

Brindle, J.T. et al, 2002, "Rapid and noninvasive diagnosis of the presence and severity of coronary heart disease using $^1$H-NMR-based metabonomics", *Nat. Med.*, vol. 8, pp. 1439-1444.

Claridge, T.D.W., 1999, *High-Resolution NMR techniques in Organic Chemistry*; Elsevier: Amsterdam.

Cloarec, O., et al, 2005, "Evaluation of the orthogonal projection on latent structure model limitations caused by chemical shift variability and improved visualization of biomarker changes in $^1$H NMR spectroscopic metabonomic studies", *Anal. Chem.*, vol. 77, pp. 517-526.

Cloarec, O., et al., 2005, "Statistical total correlation spectroscopy: An exploratory approach for latent biomarker identification from metabolic $^1$H NMR data sets", *Anal. Chem.*, vol. 77, pp. 1282-1289.

Holmes, E., et al, 1994, "Automatic data reduction and pattern recognition methods for analysis of $^1$H nuclear magnetic resonance spectra of human urine from normal and pathological states", *Anal. Biochem.*, vol. 220, pp. 284-296.

Holmes, E., et al, 2000, "Chemometric models for toxicity classification based on NMR spectra of biofluids", *Chem. Res. Toxicol.*, vol. 13, pp. 471-478.

Holmes, E., et al, 1998, "The identification of novel biomarkers of renal toxicity using automatic data reduction techniques and PCA of proton NMR spectra of urine", *Chemom. Intell. Lab. Syst.*, vol. 44, pp. 245-255.

Lindon, J. C., et al, 2003, "So what's the deal with tabonomics? Metabonomics measures the fingerprint of biochemical perturbations caused by disease, drugs, and toxins", *Anal. Chem.*, vol. 75, pp. 385A-391A.

Nicholson, J. K., et al, 1999, "Metabonomics'; understanding the metabolic responses of living systems to pathophysiological stimuli via multivariate statistical analysis of biological NMR spectroscopic data", *Xenobiotica*, vol. 29, pp. 1181-1189.

Noda, I., 1989, "Two-dimensional infrared spectroscopy", *J. Am. Chem. Soc.*, vol. 111, pp. 8116-8118.

Noda, I., 1993, "Generalized two-dimensional correlation method applicable to infrared, raman, and other types of spectroscopy", *Appl. Spectrosc.*, vol. 47, pp. 1329-1336.

Noda, I., 1990, "Two-dimensional infrared (2D IR) spectroscopy: theory and applications", *Appl. Spectrosc.*, vol. 44, pp. 550-561.

Noda, I., et al, 2000, "Generalized two-dimensional correlation spectroscopy", *Appl. Spectrosc.*, vol. 54, pp. 236A-248A.

Osaki, Y., et al, 1998, "Two-dimensional near infrared correlation spectroscopy: principle and its applications", *J. Near Infrared Spectrosc.*, vol. 6, pp. 19-31.

Plumb, R. S., et al, 2002, "Metabonomics: the use of electrospray mass spectrometry coupled to reversed-phase liquid chromatography shows potential for the screening of rat urine in drug development", *Rapid Commun. Mass Spectrom.*, vol. 16, pp. 1991-1996.

Sasic, S., et al, 2000, "A new possibility of the generalized two-dimensional correlation spectroscopy. 1. Sample—sample correlation spectroscopy", *J. Phys. Chem. A*, vol. 104, pp. 6380-6387.

Trygg, J., et al, 2002, "Orthogonal projections to latent structures (O-PLS)", *J. Chemom.*, vol. 16, pp. 119-128.

Trygg, J., 2002, "O2-PLS for qualitative and quantitative analysis in multivariate calibration", *J. Chemom.*, vol. 16, pp. 283-293.

Trygg, J., et al, 2003, "O2-PLS, a two-block (X-Y) latent variable regression (LVR) method with an integral OSC filter", *J. Chemom.*, vol. 17, pp. 53-64.

\* cited by examiner

METHOD FOR THE IDENTIFICATION OF MOLECULES AND BIOMARKERS USING CHEMICAL, BIOCHEMICAL AND BIOLOGICAL DATA

RELATED APPLICATION

This application is related to U.S. Provisional Patent Application No. 60/672,500 filed 19 Apr. 2005, the contents of which are incorporated herein by reference in their entirety.

TECHNICAL FIELD

This invention pertains generally to the field of multivariate statistics, and in particular to new methods for the analysis (e.g., chemometrics) of chemical, biochemical, and biological data, including, for example, spectral data, including but not limited to nuclear magnetic resonance (NMR) spectral data. These methods are useful, for example, in metabonomics, proteomics, transcriptomics, genomics, etc., and form a part of other methods, for example, methods for the identification of chemical species, methods for the identification of biomarkers that are useful in methods of classification, diagnosis, prognosis, etc.

BACKGROUND

A number of patents and publications are cited herein in order to more fully describe and disclose the invention and the state of the art to which the invention pertains. Full citations for these documents are provided herein. Each of these documents is incorporated herein by reference in its entirety into the present disclosure, to the same extent as if each individual documents was specifically and individually indicated to be incorporated by reference. For the avoidance of doubt, the citation of a document herein is not an admission that the document is in fact prior art.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Biosystems can conveniently be viewed at several levels of bio-molecular organisation based on biochemistry, i.e., genetic and gene expression (genomic and transcriptomic), protein and signalling (proteomic) and metabolic control and regulation (metabonomic). There are also important cellular ionic regulation variations that relate to genetic, proteomic and metabolic activities, and systematic studies on these even at the cellular and sub-cellular level should also be investigated to complete the full description of the bio-molecular organisation of a bio-system.

Significant progress has been made in developing methods to determine and quantify the biochemical processes occurring in living systems. Such methods are valuable in the diagnosis, prognosis and treatment of disease, the development of drugs, for improving therapeutic regimes for current drugs, and the like.

While genomic and proteomic methods may be useful aids, for example, in drug development, they do suffer from substantial limitations. A "metabonomic" approach has been developed which is aimed at augmenting and complementing the information provided by genomics and proteomics. "Metabonomics" is conventionally defined as "the quantitative measurement of the multiparametric metabolic response of living systems to pathophysiological stimuli or genetic modification." This concept has arisen primarily from the application of $^1$H NMR spectroscopy to study the metabolic composition of biofluids, cells, and tissues and from studies utilising pattern recognition (PR), expert systems and other chemoinformatic tools to interpret and classify complex NMR-generated metabolic data sets. Metabonomic methods have the potential, ultimately, to determine the entire dynamic metabolic make-up of an organism.

As outlined above, each level of bio-molecular organisation requires a series of analytical bio-technologies appropriate to the recovery of the individual types of bio-molecular data. Genomic, proteomic and metabonomic technologies by definition generate massive data sets that require appropriate multi-variate statistical tools (chemometrics, bio-informatics) for data mining and to extract useful biological information. These data exploration tools also allow the inter-relationships between multivariate data sets from the different technologies to be investigated, they facilitate dimension reduction and extraction of latent properties and allow multidimensional visualization.

This leads to the concept of "bionomics", the quantitative measurement and understanding of the integrated function (and dysfunction) of biological systems at all major levels of bio-molecular organisation. In the study of altered gene expression, (known as transcriptomics), the variables are mRNA responses measured using gene chips, in proteomics, protein synthesis and associated post-translational modifications are typically measured using (mainly) gel-electrophoresis coupled to mass spectrometry. In both cases, thousands of variables can be measured and related to biological end-points using statistical methods. In metabolic (metabonomic) studies, NMR (especially $^1$H) and mass spectrometry have been used to provide this level of data density on bio-materials although these data can be supplemented by conventional biochemical assays.

For in vivo mammalian studies, the ability to perform metabonomic studies on biofluids is very important because it gives integrated systems-based information on the whole organism. Furthermore, in clinical settings, for the full utilization of functional genomic knowledge in patient screening, diagnostics and prognostics, it is much more practical and ethically-acceptable to analyse biofluid samples than to perform human tissue biopsies and measure gene responses.

Metabonomics offers a number of distinct advantages (over genomics and proteomics) in a clinical setting: firstly, it can often be performed on standard preparations (e.g., of serum, plasma, urine, etc.), circumventing the need for specialist preparations of cellular RNA and protein required for genomics and proteomics, respectively. Secondly, many of the risk factors already identified with a particular disorder are small molecule metabolites that will contribute to the metabonomic dataset.

A limiting factor in understanding high-content biochemical information (e.g., NMR spectra, mass spectra) is their complexity. The most efficient way to investigate these complex multiparametric data is employ the metabonomic approach in combination with computer-based "pattern recognition" (PR) methods and expert systems. These statistical tools are similar to those currently being explored by workers in the fields of genomics and proteomics.

Pattern recognition (PR) methods can be used to reduce the complexity of data sets, to generate scientific hypotheses and to test hypotheses. In general, the use of pattern recognition algorithms allows the identification, and, with some methods, the interpretation of some non-random behaviour in a complex system which can be obscured by noise or random variations in the parameters defining the system. Also, the number of parameters used can be very large such that visualisation of the regularities, which for the human brain is best in no more than three dimensions, can be difficult. Usually the number of measured descriptors is much greater than three and so simple scatter plots cannot be used to visualise any similarity between samples. Pattern recognition methods have been used widely to characterise many different types of problem ranging for example over linguistics, fingerprinting, chemistry, and psychology. In the context of the methods described herein, pattern recognition is the use of multivariate statistics, both parametric and non-parametric, to analyse spectroscopic data, and hence to classify samples and to predict the value of some dependent variable based on a range of observed measurements.

Although the utility of the metabonomic approach is well established, its full potential has not yet been exploited. The metabolic variation is often subtle, and powerful analysis methods are required for detection of particular analytes, especially when the data (e.g., NMR spectra) are so complex. New methods to extract useful metabolic information from biofluids are needed in order to be able to achieve clinically useful diagnosis of disease. Methods of analysing data (e.g., NMR spectral data), such as those described herein, may be used to identify diagnostic chemical species (e.g., biomarkers) that may subsequently be used to classify a test sample or subject, for example, in diagnosis, prognosis, etc. These methods represent a significant advance over previously described methodologies.

SUMMARY OF THE INVENTION

One aspect of the present invention pertains to a method of identifying a sample constituent (e.g., a chemical species) on the basis of measurement values (e.g., NMR signal intensity values) for corresponding measurement variables (e.g., chemical shifts) that are correlated, specifically as determined by generating a measure of the correlation between: each spectrum of measurement values (e.g., NMR signal intensity values) in a first set of spectra and each spectrum of measurement values (e.g., NMR signal intensity values) in a second set of spectra. Note that, in this context, "spectrum" and "spectra" are used in the mathematical sense—see below.

Thus, one aspect of the present invention pertains to a method of identifying a sample constituent (e.g., a chemical species) of a sample, the method comprising the steps of:

(a) providing a plurality of spectra defining a first set of spectra, wherein each spectrum of said set of spectra is a spectrum of measurement values derived from different measurements of a property of a sample comprising said sample constituent, each measurement value corresponding to one of a range of measurement variables defining the spectrum;

(b) providing a plurality of spectra defining a second set of spectra, wherein each spectrum of said set of spectra is a spectrum of measurement values derived from different measurements of a property of a sample comprising said sample constituent, each measurement value corresponding to one of a range of measurement variables defining the spectrum;

(c) generating a measure of the correlation between: each spectrum of measurement values in the first set of spectra and each spectrum of measurement values in the second set of spectra;

(d) generating association data though which a particular measurement variable in any spectrum of the first set of spectra, and a particular measurement variable in any spectrum of the second set of spectra, is associated to the measure of correlation between: the measurement values of the respective given measurement variables;

(e) identifying said sample constituent using the measure of correlation and the association data.

Another aspect of the present invention pertains to a method of identifying a sample constituent (e.g., a chemical species) on the basis of measurement values (e.g., NMR signal intensity values) for corresponding measurement variables (e.g., chemical shifts) that are correlated, specifically as determined by generating a measure of the correlation between: the measurement values (e.g., NMR signal intensity values) in spectra of a first set of spectra corresponding to the measurement variable (e.g., chemical shift) of interest, and measurement values (e.g., NMR signal intensity values) corresponding to some or all measurement variables (e.g., chemical shifts) in a spectrum of a second set of spectra. Again note that, in this context, "spectrum" and "spectra" are used in the mathematical sense—see below.

Thus, one aspect of the present invention pertains to a method of identifying a sample constituent of a sample, the method comprising the steps of:

(a) providing a plurality of spectra defining a first set of spectra, wherein each spectrum of said set of spectra is a spectrum of measurement values derived from different measurements of a property of a sample comprising said sample constituent, each measurement value corresponding to one of a range of measurement variables defining the spectrum;

(b) providing a plurality of spectra defining a second set of spectra, wherein each spectrum of said set of spectra is a spectrum of measurement values derived from different measurements of a property of a sample comprising said sample constituent, each measurement value corresponding to one of a range of measurement variables defining the spectrum;

(c) selecting a measurement variable of interest from a spectrum of the first set of spectra; and (d) generating a measure of the correlation between: the measurement values in the spectra of the first set of spectra corresponding to the measurement variable of interest, and measurement values corresponding to some or all of the measurement variables in the spectra of the second set of spectra, (e) generating association data through which the measurement variable of interest in any spectrum of the first set of spectra, and a measurement variable in any spectrum of the second set of spectra is associated to the measure of correlation between: the measurement values of the respective measurement variables;

(f) identifying said sample constituent using the measure of correlation and the association data.

Another aspect of the present invention pertains to a method of identifying a plurality of biologically correlated sample constituents (e.g., chemical species) of a sample on the basis of measurement values (e.g., NMR signal intensity values) for corresponding measurement variables (e.g., chemical shifts) that are correlated, specifically as determined by generating a measure of the correlation between: each spectrum of measurement values (e.g., NMR signal intensity values) in a first set of spectra and each spectrum of measurement values (e.g., NMR signal intensity values) in a second set of spectra. Note that, in this context, "spectrum" and "spectra" are used in the mathematical sense—see below.

Another aspect of the invention pertains to a method of identifying a plurality of biologically correlated sample constituents of a sample, the method comprising the steps of:

(a) providing a plurality of spectra defining a first set of spectra, wherein each spectrum of said set of spectra is a spectrum of measurement values derived from different measurements of a property of a sample comprising said first sample constituent and said second sample constituent, each measurement value corresponding to one of a range of measurement variables defining the spectrum;

(b) providing a plurality of spectra defining a second set of spectra, wherein each spectrum of said set of spectra is a spectrum of measurement values derived from different measurements of a property of a sample comprising said first sample constituent and said second sample constituent, each measurement value corresponding to one of a range of measurement variables defining the spectrum;

(c) generating a measure of the correlation between: each spectrum of measurement values in the first set of spectra and each spectrum of measurement values in the second set of spectra;

(d) generating association data through which a particular measurement variable in any spectrum of the first set of spectra, and a particular measurement variable in any spectrum of the second set of spectra, is associated to the measure of correlation between: the measurement values of the respective given measurement variables;

(e) identifying said plurality of biologically correlated sample constituents using the measure of correlation and the association data.

Another aspect of the present invention pertains to a method of identifying a class-discriminant chemical species (e.g., biomarker) for a particular class membership (e.g., with disease, without disease) on the basis of measurement values (e.g., NMR signal intensity values) for corresponding measurement variables (e.g., chemical shifts) that are correlated, specifically as determined by generating a measure of the correlation between: the measurement value (e.g., NMR signal intensity value) of a class-discriminant measurement variable (e.g., class-discriminant chemical shift) of interest, and the measurement values (e.g., NMR signal intensity values) of some or all of the other measurement variables (e.g., other chemical shifts) in a data vector comprising, at least, spectral data (e.g., NMR spectral data), where the class-discriminant measurement variable (e.g., class-discriminant chemical shift) of interest is selected on the basis of correlation with the particular class, as determined using a supervised mathematical model (e.g., PLS-DA).

Another aspect of the present invention pertains to a method of identifying a class-discriminant chemical species for a particular class membership, comprising the steps of:

(a) providing a data set that comprises a plurality of data vectors for each of a plurality of classes,
each data vector comprising, at least, a spectrum and a class representation variable,
wherein said spectrum comprises measurement values derived from different measurements of a property of a sample representative of one of said plurality of classes,
each measurement value corresponding to one of a range of measurement variables;

(b) modelling said data set using a supervised mathematical model;

(c) calculating the degree of correlation between: measurement variables and class representation variables of the supervised mathematical model;

(d) identifying class-discriminant measurement variables as those measurement variables that are correlated with the particular class, thereby being discriminant for the particular class;

(e) selecting a class-discriminant measurement variable of interest according to the degree of correlation with the particular class;

(f) generating a measure of the correlation between: the measurement value of the class-discriminant measurement variable of interest, and measurement values corresponding to some or all of the other measurement variables, (g) identifying correlated measurement variables of measurement values that are relatively highly correlated with the measurement value of the class-discriminant measurement variable of interest;

(h) identifying said class-discriminant chemical species for the particular class membership using said correlated measurement variables.

These and other aspects of the present invention are described herein.

As will be appreciated by one of skill in the art, features and preferred embodiments of one aspect of the present invention will also pertain to other aspects of the present invention.

BRIEF DESCRIPTION OF THE DRAWINGS

The patent or application file contains at least one drawing executed in color. Copies of this patent or patent application publication with color drawing(s) will be provided by the United States Patent and Trademark Office upon request and payment of the necessary fee.

DETAILED DESCRIPTION OF THE INVENTION

Introduction

Figure 1:
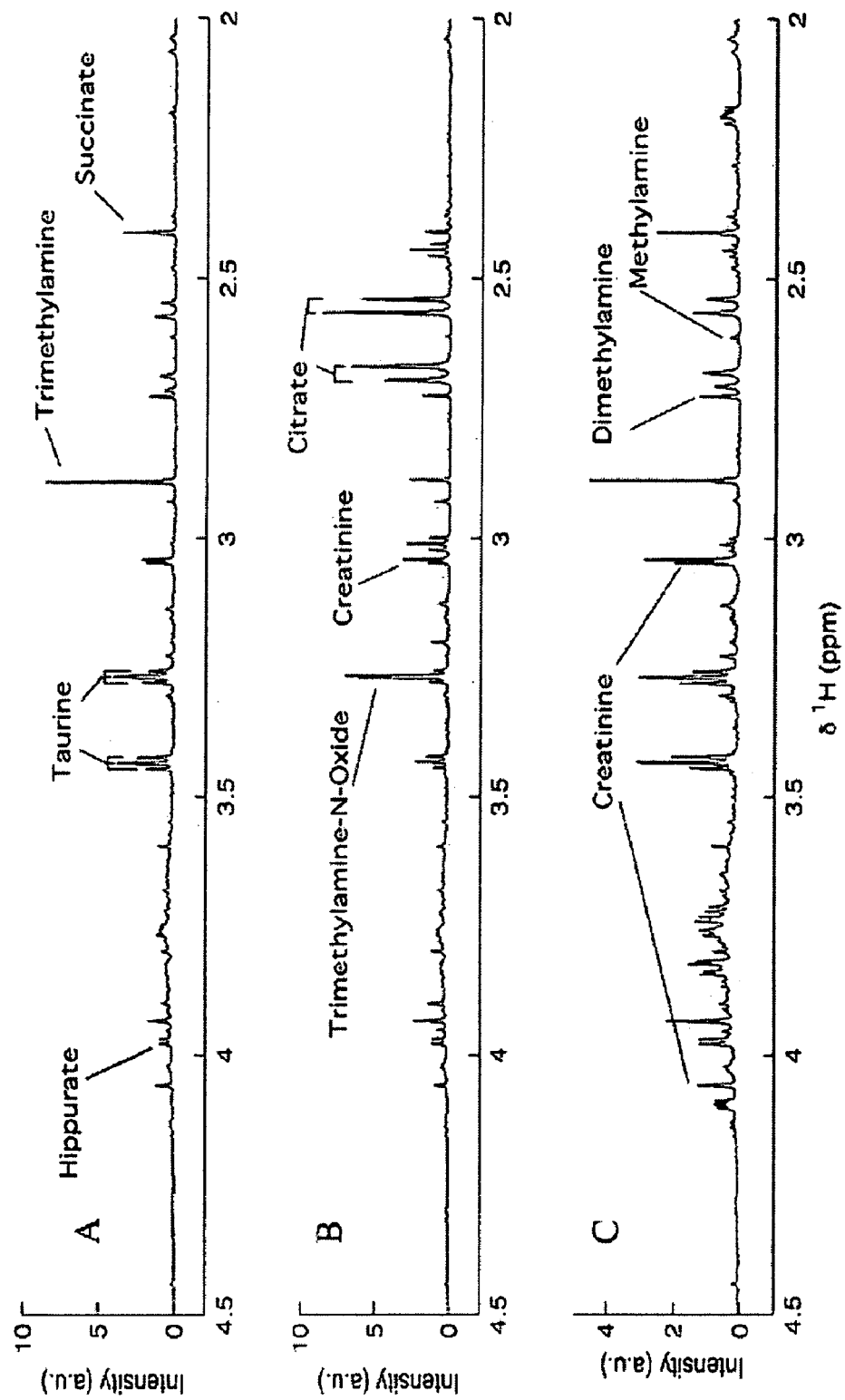
FIG. 1 is an example of partial 600-MHz $^1$H NMR spectra for three different mouse strains showing some assignments of the most abundant metabolites: (A) BALB/c; (B) C57BL/6; (C) 129S6. See Study 1 below.

Methods (which employ multivariate statistical analysis, and optionally pattern recognition (PR) techniques, and optionally data filtering techniques) of analysing data (e.g., NMR spectra, MS spectra, etc.) from a test population, and which yield accurate mathematical models which may subsequently be used to classify a test sample or subject, and/or in diagnosis, have been developed.

An NMR spectrum (or a mass spectrum, etc.) provides a fingerprint or profile for the sample to which it pertains. Such spectra represent a measure of all detectable (e.g., NMR detectable, etc.) species present in the sample (rather than a select few) and also, to some extent, interactions between these species. As such, these spectra are characterised by a high data density that, heretofore, has not been fully exploited. The methods described herein facilitate the analysis of such spectra in a manner never before described.

These methods find particular application in the field of medicine. For example, analysis of NMR spectra for samples taken from a population characterised by a certain condition can be analysed in order to reveal biomarkers that can be used to classify a sample (and therefore the corresponding subject), for example, as having, or not having, a particular condition, with a high degree of confidence.

The identities of (e.g., endogenous) species, that typically comprise only a small fraction of the total (number of or amount of) species in a sample, but that are invariably associated with the presence of a particular condition (e.g., disease), are encoded within the high data density of the spectra (e.g., NMR spectra). The methods described herein permit their identification and subsequent use for classification, diagnosis, etc.

Described herein is a Statistical TOtal Correlation Spectroscopy (STOCSY) analysis method for aiding the identification of chemical species based on spectral data and/or non-spectral data, which is particularly useful in methods of identifying potential biomarker molecules in metabonomic studies based on NMR spectroscopic data.

STOCSY takes advantage of the multi-collinearity of the intensity variables in a set of spectra (for example, $^1$H NMR spectra) to generate a pseudo-two-dimensional spectrum (for example, NMR spectrum) that displays the correlation among the intensities of the various peaks across the whole sample. When applied to NMR, this method is similar to two-dimensional NMR spectroscopic methods. However, this method is not limited to the usual connectivities that are deducible from more standard two-dimensional NMR spectroscopic methods, such as TOCSY (see, e.g., Claridge, T. D. W., *High-Resolution NMR techniques in Organic Chemistry*; Elsevier: Amsterdam, 1999). Moreover, two or more molecules involved in the same pathway can also present high intermolecular correlations because of biological covariance or can even be anti-correlated.

The combination of STOCSY with supervised pattern recognition, and particularly orthogonal projection on latent structure-discriminant analysis (O-PLS-DA), offers a new powerful framework for analysis of metabonomic data. In a first step O-PLS-DA extracts the part of spectra (e.g., NMR spectra) related to discrimination. This information may then be cross-combined with the STOCSY results in order to help identify the molecules responsible for the metabolic variation.

In general, metabonomic and metabolomic studies are based on spectroscopic or spectrometric data of complex biosamples, mainly from $^1$H NMR spectroscopy, but more recently from liquid or gas chromatography with mass spectrometry (MS) and or UV absorption studies using a diode array detector. See, for example, Brindle, J. T.; Antti, H.; Holmes, E.; Tranter, G.; Nicholson, J. K.; Bethell, H. W.; Clarke, S.; Schofield, P. M.; McKilligin, E.; Mosedale, D. E.; Grainger, D. J., *Nat. Med.*, 2002, 8, 1439-1444; Lindon, J. C.; Holmes, E.; Nicholson, J. K., *Anal. Chem.*, 2003, 75, 384A-391A; Nicholson, J. K.; Lindon, J. C.; Holmes, E., *Xenobiotica*, 1999, 29, 1181-1189; Plumb, R. S.; Stumpf, C. L.; Gorenstein, M. V.; Castro-Perez, J. M.; Dear, G. J.; Anthony, M.; Sweatman, B. C.; Connor, S. C.; Haselden, J. N., *Rapid Commun. Mass Spectrom.*, 2002, 16, 1991-1996.) Multivariate statistical and pattern recognition methods have been developed to extract sample classification and associated biomarker information from NMR spectroscopic data because of the high complexity of biofluids containing potentially thousands of different metabolites. (See, e.g., Nicholson, J. K.; Foxall, P. J. D.; Spraul, M.; Farrant, R. D.; Lindon, J. C., *Anal. Chem.*, 1995, 67, 793-811.) A well-established way to analyze NMR spectral data has involved first a reduction of these data by integration of spectral sections into bins (frequency windows), which have generally corresponded to a typical spectral width of 0.01-0.04 ppm. This serves to stabilize effects of the peak position variation due to physicochemical environment differences (pH, ionic concentration) and allow a smaller, more manageable, number of variables for statistical processing. (See, e.g., Holmes, E.; Foxall, P. J. D.; Nicholson, J. K.; Neild, G. H.; Brown, S. M.; Beddell, C. R.; Sweatman, B. C.; Rahr, E.; Lindon, J. C.; Spraul, M.; Neidig, P., *Anal. Biochem.*, 1994, 220, 284-296.) Analysis is then carried out using chemometric tools, such as principal components analysis (PCA) and projection to latent structures (PLS, also called partial least squares), to discover the variables describing the metabolic variation involved in the particular study and to allow categorization of the samples from the study. (See, e.g., Holmes, E.; Nicholls, A. W.; Lindon, J. C.; Connor, S. C.; Connelly, J. C.; Haselden, J. N.; Damment, S. J.; Spraul, M.; Neidig, P.; Nicholson, J. K., *Chem. Res. Toxicol.*, 2000, 13, 471-478.) Finally, the parts of the spectra corresponding to the most discriminatory variables are displayed in order to allow identification of the varying metabolites or biomarkers for a particular condition. (See, e.g., Holmes, E.; Nicholson, J. K.; Nicholls, A. W.; Lindon, J. C.; Connor, S. C.; Polley, S.; Connelly, J., *Chemom. Intell. Lab. Syst.*, 1998, 44, 245-255.)

Recently, it has been shown that it is possible to use full spectral resolution, including all intensity values in a full spectrum, and that inclusion of variable peak position data such as caused by pH differences between samples) can even be beneficial. (See, e.g., Cloarec, O.; Dumas, M.-E.; Trygg, J.; Craig, A.; Barton, R. H.; Lindon, J. C.; Nicholson, J. K.; Holmes, E., submitted for publication in *Anal. Chem. Analytical Chemistry A*.) The interpretation of autoscaled chemometric models combining back-scaled PLS coefficient plots and variable weights demonstrated that this peak position variation can be handled successfully, and can in fact provide additional useful information on the physicochemical variations in metabonomic data sets. This method proved to be a useful tool in identifying the $^1$H NMR resonances corresponding to the most influential metabolites without the need to re-consult the initial spectra. However, when the number of different resonances is high, as in a biofluid such as urine, the identification of the molecules can be difficult. In order to address this difficulty in interpretation, the inventors have developed statistical total correlation spectroscopy (STOCSY).

The methods described herein are in some ways similar to methods introduced by Sasic et al. (see, e.g., Sasic, S.; Muzynski, A.; Ozaki, Y., *J. Phys. Chem. A*, 2000, 104, 6380-6387) and also a method for generalized two-dimensional correlation spectroscopy proposed by Noda (see, e.g., Noda, I.; Dowrey, A. E.; Marcott, C.; Story, G. M.; Ozaki, Y., *Appl. Spectrosc.*, 2000, 54, 236A-248A; Noda, I., *J. Am. Chem. Soc.*, 1989, 111, 8116-8118; Noda, I., *Appl. Spectrosc.*, 1993, 47, 1329-1336; Noda, I,. *Appl. Spectrosc.*, 1990, 44, 550-561). Slightly similar correlative approaches have been applied to infrared, Raman, near-infrared, and fluorescence spectroscopies, where correlations between different spectral features could be identified (see, e.g., Osaki, Y.; Wang, Y. J., *Near Infrared Spectrosc.*, 1998, 19, 6-13). However, such correlation methods have not yet been applied to NMR spectroscopy, nor to the spectroscopy of complex mixtures where the information density and resolution is much higher than that obtained from other spectroscopic techniques.

The methods described herein allow identification of highly correlated peak intensities that can lead directly to identification of peaks from the same molecule and hence assist with molecule identification. Additionally, identification of lower or even negative correlations could permit the identification of substances in the same metabolic pathway whose concentrations are interdependent or under some common regulatory mechanism. Both types of information are important for biomarker analysis and identification.

Also described herein is a new framework for the data analysis of metabonomic data combining spectroscopy (e.g., NMR spectroscopy) with orthogonal projection on latent structure. (See, e.g., Trygg, J.; Wold, S., *J. Chemom.*, 2002, 16, 119-128.) This combination allows the rapid visualization and identification of the molecules involved in the differentiation between metabolic states arising from strains of animal, toxicity, disease, therapeutic intervention (biomarkers), etc.

Thus, one aspect of the present invention pertains to new methods of identifying a chemical species in a sample using, for. example, NMR spectroscopy. In general, statistical methods (e.g., the calculation of part or all of a correlation matrix) are applied to spectral data (for example, spectral data that is, or comprises, NMR spectral data) and/or non-spectral data, in order to determine those parts of the spectrum (e.g., those peaks of the NMR spectrum) that are highly correlated, and a structural assignment is then made on that basis (e.g., on the basis of the highly correlated peaks). Such methods may be conveniently described as Statistical Total Correlation Spectroscopy (STOCSY).

Another aspect of the present invention pertains to new methods of identifying biomarkers (e.g., chemical species) that are useful in classification (e.g., in diagnosis). In general, pattern recognition methods are applied to modelling data of known classes (e.g., with disease, without disease) that is, or comprises, spectral data (e.g., NMR spectral data) and/or non-spectral data, in order to determine those parts of the spectrum (e.g., those peaks of the NMR spectrum) that are highly discriminant (e.g., are useful in discriminating between classes). Having identified particular parts of the spectrum (e.g., peaks in the NMR spectrum) that are useful in discrimination, STOCSY analysis (as described above) is applied to those parts of the spectrum (e.g., peaks in the NMR spectrum) in order to identify the underling chemical species that is highly discriminant (e.g., are useful in discriminating between classes).

Features of these methods are described in Cloarec et al., *Anal. Chem.*, 1 Mar. 2005, Vol. 77, pp. 1282-1289, first published on the Web on 1 Jan. 2005. For the avoidance of doubt, the contents of this document are incorporated herein by reference in their entirety into the present disclosure.

Methods of Identifying Chemical Species

As mentioned above, one aspect of the present invention pertains to new methods of identifying a chemical species in a sample using, for example, NMR spectroscopy. In general, statistical methods (e.g., the calculation of part or all of a correlation matrix) are applied to spectral data (for example, spectral data that is, or comprises, NMR spectral data) and/or non-spectral data, in order to determine those parts of the spectrum (e.g., those peaks of the NMR spectrum) that are highly correlated, and a structural assignment is then made on that basis (e.g., on the basis of the highly correlated peaks). Such methods may be conveniently described as Statistical Total Correlation Spectroscopy (STOCSY).

Statistical Total Correlation Spectroscopy (STOCSY):

Statistical total correlation spectroscopy (STOCSY) is based on the properties of the correlation matrix C, computed from a set of sample spectra according to $$C = \frac{1}{n-1} X_1^t X_2$$

where $X_1$ and $X_2$ denote the autoscaled (each variable is centered and scaled to unit variance) experimental matrices of $n \times v_1$ and $n \times v_2$, respectively; n is the number of spectra (one for each sample) and $v_1$ and $v_2$ are the number of variables in the spectra for each matrix. C is therefore a matrix of $v_1 \times v_2$, where each value is a correlation coefficient between two variables of the matrices $X_1$ and $X_2$. The simplest case is the autocorrelation analysis where $X_1 = X_2$.

The covariance matrix, V, is calculated in the same way as the correlation matrix, C, except that $X_1$ and $X_2$ denote the centred (each variable is centered, but not scaled to unit variance) experimental matrices.

Note that, in this context, "spectrum" and "spectra" are used in the mathematical sense, and refer to an array or arrays of data, i.e., an array or arrays of measurement values and corresponding measurement variables. This is distinct from the term "spectral data," which, as used herein, refers to data that is spectroscopic data (e.g., NMR data, UV absorption data, IR absorption data) (e.g., an NMR spectrum, a UV absorption spectrum, an IR absorption spectrum) or spectrometric data (e.g., mass spectrum data) (e.g., a mass spectrum). In one embodiment, the "spectrum" is, or comprises, an array of spectral data. In one embodiment, the "spectrum" is, or comprises, or additionally comprises, other non-spectral data, such as metabonomic, proteomic, transcriptomic, and/or genomic data.

Because the different resonance intensities from a single molecule will always have the same ratio (if the spectrometer conditions are kept identical between samples), the relative intensities will be theoretically totally correlated (correlation coefficient r=1). In real samples of biofluids, r is always less than 1 because of spectral noise or peak overlaps from other molecules. However, in practice, the correlation matrix from a set of spectra containing different amounts of the same molecule shows very high correlations between the variables corresponding to the resonances of the same molecule.

Plotting the correlation matrix (e.g., as a correlation map) provides a graphic representation of the multi-sample spectroscopic data set comparable to that of a two-dimensional (2D) correlation NMR experiment conducted on one sample containing all the molecules of all the samples.

The closest NMR experiment to STOCSY is TOCSY (total correlation spectroscopy), the signals of which arise from protons within a spin system. (See, e.g., Braunschweiler, L.; Ernst, R. R., *J. Magn. Reson.*, 1983, 53, 521-528.) In a standard TOCSY experiment, NMR data is collected for a single sample while a perturbation is applied; it is this perturbation that generates variation that contains additional information about the system. In contrast, in a STOCSY experiment, NMR data is collected for a number of samples, without the application of a perturbation; here, it is the inherent variation of the samples that contains additional information about the system.

In principle, concentrations of other molecules can also be correlated to the initial molecule of interest, and quantitative relationships between molecules can therefore be highlighted. For example, molecules in the same biochemical pathway may exhibit a similar or even co-dependent response to a stimulus. In this case, the correlation between resonances from different molecules would be high but not usually as strong as for resonances on the same molecule.

The method is not restricted to the $^1$H-$^1$H correlation but can be applied to different nuclei. If these involve different NMR-active nuclei ($^{13}$C-$^{13}$C, $^1$H-$^{13}$C, $^1$H-$^{31}$P, $^{13}$C-$^{31}$P, etc.), $X_1$ not equal to $X_2$, then heteronuclear correlation is also possible, yielding molecular connectivity information using both types of nuclear spin properties.

Also, it should be noted that STOCSY can be used to derive NMR spectral splittings and J couplings with the same theoretical precision of the one-dimensional (1D) spectral properties from which the 2D data set was derived and it is not limited by low resolution in the $F_1$ domain of most correlation 2D experiments, which are typically much lower than the standard 1D spectrum. This is possible, of course, provided that any physicochemical environment variation between samples does not induce variation of the peak positions.

Additionally, note that although the methods are described herein primarily with reference to NMR spectral data, the methods are also applicable to other types of data, including, for example, spectral data, for example, mass spectral (MS) data, infrared absorption data (e.g., FTIR), UV absorption data, etc., and non-spectral data, for example, metabonomic, proteomic, transcriptomic, and/or genomic data.

2-Dimensional STOCSY:

Thus, one aspect of the present invention pertains to a method of identifying a sample constituent (e.g., a chemical species) on the basis of measurement values (e.g., NMR signal intensity values) for corresponding measurement variables (e.g., chemical shifts) that are correlated, specifically as determined by generating a measure of the correlation between: each spectrum of measurement values (e.g., NMR signal intensity values) in a first set of spectra and each spectrum of measurement values (e.g., NMR signal intensity values) in a second set of spectra.

Thus, one aspect of the present invention pertains to a method of identifying a sample constituent (e.g., a chemical species) of a sample, the method comprising the steps of:
(a) providing a plurality of spectra defining a first set of spectra, wherein each spectrum of said set of spectra is a spectrum of measurement values derived from different measurements of a property of a sample comprising said sample constituent, each measurement value corresponding to one of a range of measurement variables defining the spectrum;
(b) providing a plurality of spectra defining a second set of spectra, wherein each spectrum of said set of spectra is a spectrum of measurement values derived from different measurements of a property of a sample comprising said sample constituent, each measurement value corresponding to one of a range of measurement variables defining the spectrum;
(c) generating a measure of the correlation between: each spectrum of measurement values in the first set of spectra and each spectrum of measurement values in the second set of spectra;
(d) generating association data though which a particular measurement variable in any spectrum of the first set of spectra, and a particular measurement variable in any spectrum of the second set of spectra, is associated to the measure of correlation between: the measurement values of the respective given measurement variables;
(e) identifying said sample constituent using the measure of correlation and the association data.

In one embodiment, step (a) is generating a plurality of spectra defining a first set of spectra.

In one embodiment, step (b) is generating a plurality of spectra defining a second set of spectra.

In one embodiment, said first set of spectra and said second set of spectra are identical.

In one embodiment, said first set of spectra and said second set of spectra are different.

In one embodiment, said plurality of spectra (e.g., defining a first set of spectra, defining a second set of spectra) is at least 3, e.g., at least 5, e.g., at least 10, e.g., at least 20, e.g., at least 50, e.g., at least 100).

Again, note that, in this context, "spectrum" and "spectra" are used in the mathematical sense, and refers to an array or arrays of data, i.e., an array or arrays of measurement values and corresponding measurement variables. This is distinct from the term "spectral data," which, as used herein, refers to data that is spectroscopic data (e.g., NMR data, UV absorption data, IR absorption data) (e.g., an NMR spectrum, a UV absorption spectrum, an IR absorption spectrum) or spectrometric data (e.g., mass spectrum data) (e.g., a mass spectrum). In one embodiment, the "spectrum" is, or comprises, an array of spectral data. In one embodiment, the "spectrum" is, or comprises, or additionally comprises, other non-spectral data, such as metabonomic,. proteomic, transcriptomic, and/or genomic data.

Again, note that although these methods are described herein primarily with reference to NMR spectral data, these methods are also applicable to other types of spectral data and/or non-spectral data.

For example, the "spectrum" may be an NMR spectrum (e.g., $^1$H NMR, $^{13}$C NMR, $^{31}$P NMR, etc.); the "measurement values" may be NMR signal intensity values; the "property" may be NMR signal; the "measurement variables" may be chemical shifts or a surrogate therefor; etc.

For example, the "spectrum" may be a mass spectrum (MS); the "measurement values" may be mass spectral intensity values (e.g., integrated ion counts, etc.); the "property" may be mass spectral ion signal; the "measurement variables" may be mass-to-charge (m/z) ratios or a surrogate therefor; etc.

For example, the "spectrum" may be an infrared (IR) spectrum (e.g., a Fourier transform infrared (FTIR) spectrum); the "measurement values" may be infrared absorption values; the "property" may be infrared absorption; the "measurement variables" may be wave number (i.e., reciprocal wavelength) or a surrogate therefor; etc.

For example, the "spectrum" may be an ultraviolet (UV) absorption spectrum; the "measurement values" may be absorption values; the "property" may be ultraviolet absorption; the "measurement variables" may be wavelength, or a surrogate therefor; etc.

For example, the "spectrum" may be an array of metabonomic data; the "measurement values" may be metabolite levels; the "property" may be the amount of metabolite; the "measurement variables" may be a name or label associated with the metabolite, or a surrogate therefor; etc.

For example, the "spectrum" may be an array of proteomic data; the "measurement values" may be protein levels; the "property" may be the amount of protein; the "measurement variables" may be a name or label associated with the protein, or a surrogate therefor; etc.

For example, the "spectrum" may be an array of transcriptomic data; the "measurement values" may be expressed protein levels; the "property" may be the amount of expressed protein; the "measurement variables" may be a name or label associated with the gene, or a surrogate therefor; etc.

For example, the "spectrum" may be an array of genomic data; the "measurement values" may be indicators of the presence or absence of a gene; the "property" may be presence or absence of the gene; the "measurement variables" may be a name or label associated with the gene, or a surrogate therefor; etc.

In one embodiment, the method is a method of identifying a sample constituent (e.g., a chemical species) from a spectrum (e.g., an NMR spectrum) of measurement values (e.g., NMR signal intensity values) derived from different measurements of a property (e.g., NMR signal) of a sample comprising said sample constituent, each measurement value (e.g., NMR signal intensity value) corresponding to one of a range of measurement variables (e.g., chemical shifts) defining the spectrum, the method comprising the steps of:

(a) providing a plurality of said spectra defining a first set of spectra (e.g., NMR spectra);
(b) providing a plurality of said spectra defining a second set of spectra (e.g., NMR spectra);
(c) generating a measure of the correlation between: each spectrum of measurement values (e.g., NMR signal intensity values) in the first set of spectra and each spectrum of measurement values (e.g., NMR signal intensity values) in the second set of spectra;
(d) generating association data with which a particular measurement variable (e.g., chemical shift) in any spectrum of the first set of spectra, and a particular measurement variable (e.g., chemical shift) in any spectrum of the second set of spectra, is associated to the measure of correlation between: the measurement values (e.g., NMR signal intensity value) of the respective given measurement variables (e.g., chemical shifts);
(e) identifying said sample constituent using the measure of correlation and the association data.

In one embodiment, step (a) is generating a plurality of said spectra defining a first set of spectra (e.g., NMR spectra).

In one embodiment, step (b) is generating a plurality of said spectra defining a second set of spectra (e.g., NMR spectra).

In one embodiment, said first set of spectra and said second set of spectra are identical.

In one embodiment, said first set of spectra and said second set of spectra are different.

For example, a set (e.g., first set, second set) of spectra (e.g., NMR spectra) may be represented as a matrix representation in which each measurement value (e.g., NMR signal intensity value) has data items associated with it identifying the measurement variable (e.g., the value of the independent variable of the spectrum) (e.g., chemical shift) with which the measurement value is associated, and also identifying the spectrum (e.g., which spectrum of the set of spectra, e.g., the spectrum number) with which the measurement value is associated. The measurement values (e.g., NMR signal intensity values) of a plurality of spectra common to a set may then be represented as elements of a common matrix in which the data item representing the spectrum to which a measurement value belongs (e.g., which spectrum of the set of spectra) corresponds with a predetermined row co-ordinate in the matrix, while the measurement variable (e.g., chemical shift) with which it is associated corresponds to a predetermined column co-ordinate in the matrix (or vice versa). In this way each measurement (e.g., NMR signal intensity value) in each spectrum in a set of spectra may be assigned a matrix co-ordinate, and successive measurement values viewed along a row (or, alternatively, a column) of the matrix may represent a given spectrum as a whole.

The property (e.g., NMR signal intensity value) measured in a given spectrum of a set is preferably the property measured in each of the other spectra of the set (e.g., the set is a set of NMR spectra). The measurement variable(s) (e.g., chemical shift) employed in a spectrum is/are preferably shared by all spectra common to a set (e.g., each NMR spectrum of the set of NMR spectra is for the same range of chemical shift). For example, each spectrum of a set of spectra may be a spectrum of NMR signal intensity plotted as a function of chemical shift (which serves as the independent variable in the spectrum), such that each measurement in the spectrum is associated with a respective chemical shift value, and each measurement value is an NMR signal intensity value.

Preferably, each spectrum of a given set of spectra is distinct from, or generated separately from, any other spectrum within the set. In this way, each spectrum of a set is potentially different from any other spectrum of the set.

Optionally, each spectrum of a given set of spectra is obtained for the same sample comprising the sample constituent. Optionally, each spectrum of a given set of spectra is obtained for a different sample comprising the sample constituent.

The step of providing/generating a measure of the correlation between each spectrum of measurement values in the first set of spectra and each spectrum of measurement values in the second set of spectra may be preformed by the following method:

(i) representing each of the first and second sets in a matrix form (such as described above) with row co-ordinates of each matrix identifying different spectra of the set and column co-ordinates of each matrix identifying measurement values (e.g., NMR signal intensity value) associated with a given measurement variable (e.g., chemical shift) common to each spectrum (or vice versa, i.e., exchange rows for columns);

(ii) autoscaling each matrix (i.e., each column of the matrix is centred and scaled by subtracting its mean from each row value and by dividing each row value by the standard deviation of the column);

(iii) multiplying the transpose of the autoscaled matrix representing the first set of spectra with the autoscaled matrix representing the second set of spectra.

In this way, one obtains a correlation matrix, each element of which represents a measure of the correlation (subsequent to any desired normalisation thereof) between measurement values (e.g., NMR signal intensity values) of one set with measurement values in the other set.

By employing a matrix representation for the first and second sets, one may produce a measure/measures of correlation also represented in matrix form as discussed above (e.g., the correlation matrix). Accordingly, the association data, through which a measurement variable in any spectrum of the first set of spectra and a measurement variable in any spectrum of the second set of spectra is associated to the measure of correlation between the measurement values corresponding to the respective measurement variables, naturally follows from the matrix co-ordinate ordering of the elements of the correlation matrix. It may be convenient to consider the association data to be the link through which a particular measure of correlation (between particular measurement values) is linked to (associated with) the underlying measurement variables (for those measurement values).

Specifically, successive values of correlation matrix column co-ordinates within a given row of the correlation matrix may correspond with successive values of the measurement variable employed in (and common to) the spectra of the first set of spectra, while successive values of correlation matrix row co-ordinates within a given column of the correlation matrix may correspond with successive values of the measurement variable employed in (and common to) the spectra of the second set of spectra (or vice versa). Thus, each value of the measurement variable employed within a given spectrum at which a measurement value was obtained identifies that measurement value. Using the matrix co-ordinates of a given correlation matrix element, one may associate that correlation matrix element with the values of the measurement variables (e.g., chemical shifts) in the spectra of the first and second sets which resulted in that correlation element.

In a very simplified, but illustrative, example, consider a set of three spectra:

Spectrum A=$(x_{1,1}, x_{1,2}, x_{1,3})$;

Spectrum B=$(x_{2,1}, x_{2,2}, x_{2,3})$;

Spectrum C=$(x_{3,1}, x_{3,2}, x_{3,3})$;

here represented as row vectors (e.g., a, b, c) having elements (e.g., $x_{1,1}$, $x_{1,2}$, $x_{1,3}$) corresponding to (in this case, three) successive measurement values (e.g., NMR signal intensities) corresponding to (in this case, three) different respective values (values 1, 2 and 3) of the measurement variable (e.g., chemical shifts, $\delta_1$, $\delta_2$, and $\delta_3$) employed in the spectrum. For example, $x_{2,2}$ may be the NMR signal intensity at chemical shift $\delta_2$ (e.g., $\delta$ 5.217) for spectrum B, etc. Of course, a typical spectrum (e.g., NMR spectrum) has many hundreds, if not many thousands of elements, for example, each corresponding to a particular chemical shift, $\delta_i$, a particular chemical shift range, $\Delta\delta_i$, etc.

A first set, S1, of spectra may be constructed in matrix form using these three separate spectra as:

$$S1 = \begin{pmatrix} x_{1,1} & x_{1,2} & x_{1,3} \\ x_{2,1} & x_{2,2} & x_{2,3} \\ x_{3,1} & x_{3,2} & x_{3,3} \end{pmatrix}$$

and the corresponding autoscaled matrix is:

$$X1 = \begin{pmatrix} \frac{x_{1,1} - \bar{x}_1}{s_1} & \frac{x_{1,2} - \bar{x}_1}{s_2} & \frac{x_{1,3} - \bar{x}_3}{s_3} \\ \frac{x_{2,1} - \bar{x}_1}{s_1} & \frac{x_{2,2} - \bar{x}_2}{s_2} & \frac{x_{2,3} - \bar{x}_3}{s_3} \\ \frac{x_{3,1} - \bar{x}_1}{s_1} & \frac{x_{3,2} - \bar{x}_2}{s_2} & \frac{x_{3,3} - \bar{x}_3}{s_3} \end{pmatrix}$$

where $s_i$ and $\bar{x}_i$ are the standard deviation and the mean of the column i, respectively.

A second set, X2, of spectra may be identical to the first set, or may contain different spectra. For simplicity, the present example assumes that the first set is identical to the second set (i.e., X1=X2 and S1=S2), such that the correlation matrix C is given by:

$$C = \frac{1}{2} \begin{pmatrix} \frac{x_{1,1} - \bar{x}_1}{s_1} & \frac{x_{1,2} - \bar{x}_1}{s_2} & \frac{x_{1,3} - \bar{x}_3}{s_3} \\ \frac{x_{2,1} - \bar{x}_1}{s_1} & \frac{x_{2,2} - \bar{x}_2}{s_2} & \frac{x_{2,3} - \bar{x}_3}{s_3} \\ \frac{x_{3,1} - \bar{x}_1}{s_1} & \frac{x_{3,2} - \bar{x}_2}{s_2} & \frac{x_{3,3} - \bar{x}_3}{s_3} \end{pmatrix} \cdot \begin{pmatrix} \frac{x_{1,1} - \bar{x}_1}{s_1} & \frac{x_{1,2} - \bar{x}_1}{s_2} & \frac{x_{1,3} - \bar{x}_3}{s_3} \\ \frac{x_{2,1} - \bar{x}_1}{s_1} & \frac{x_{2,2} - \bar{x}_2}{s_2} & \frac{x_{2,3} - \bar{x}_3}{s_3} \\ \frac{x_{3,1} - \bar{x}_1}{s_1} & \frac{x_{3,2} - \bar{x}_2}{s_2} & \frac{x_{3,3} - \bar{x}_3}{s_3} \end{pmatrix}$$

$$C = \begin{pmatrix} C_{1,1} & C_{1,2} & C_{1,3} \\ C_{2,1} & C_{2,2} & C_{2,3} \\ C_{3,1} & C_{3,2} & C_{3,3} \end{pmatrix}$$

where:

$$C_{i,j} = \frac{1}{2} \sum_{k=1}^{3} \left( \frac{x_{k,j} - \bar{x}_i}{s_i} \right) \cdot \left( \frac{x_{k,j} - \bar{x}_j}{s_j} \right),$$

$C_{i,j} = C_{j,i}$ and because $X1 = X2$, $C_{i,i} = 1$

Again, since a typical spectrum (e.g., NMR spectrum) has many hundreds, if not many thousands of elements, the correlation matrix, C, is a square matrix, with many hundreds, if not many thousands of rows/columns, where each element has co-ordinates (row and column numbers), each of which corresponds, for example, to a particular chemical shift, $\delta_i$, a particular chemical shift range, $\Delta\delta_i$, etc.

Thus, the value of an element (e.g. $C_{2,3}$) of the correlation matrix provides the measure of correlation between specific parts of spectra (e.g., the NMR signal intensity at a particular chemical shift), and the matrix co-ordinates ("23") (e.g., the association data) identify the specific parts of the spectra (e.g., the particular chemical shift values) with which the measure is associated—namely, the measurement variable values 2 and 3 (e.g., $\delta_2$ and $\delta_3$, e.g., $\delta$ 5.217 and $\delta$ 1.192).

The values of each matrix element of the succession of matrix elements in a given row (or column) of the correlation matrix thus represents the measures of the correlation as between: (a) the measurement values of the spectra at a corresponding succession of values of the measurement variable (identified by the column (or row) number of the matrix element in the succession), and (b) the measurement values of the spectra at one common value of the measurement variable (identified by the row number for that row (or column)).

For example, when S is a matrix with rows representing a number of NMR spectra, (i.e., elements of each row being the NMR signal intensity for successive chemical shift values for that spectrum), then a particular row of the correlation matrix (e.g., the row of C associated with $\delta$ 5.217) gives the correlation as between: (a) the NMR signal intensity for each of the range of chemical shift values, and (b) the NMR signal intensity for $\delta$ 5.217. Also, a particular element in a particular row of the correlation matrix (e.g., the element associated with $\delta$ 2.313 in the row of C associated with $\delta$ 5.217) gives the correlation between: (a) the NMR signal intensity at $\delta$ 2.313, and (b) the NMR signal intensity for $\delta$ 5.217.

The association data and correlation measures may be graphically presented in combination with each other using any suitable graphical representation means as would be readily apparent to the skilled person. For example, the data may be graphically presented by generating a 2-dimensional (2D) plot employing the same or similar co-ordinate system as the correlation matrix, for example, so that the values of some or all of the matrix elements of the correlation matrix are plotted/represented in a common graphic at a relative position within the graphic which matches the relative positions between the matrix elements in the correlation matrix itself (e.g., a correlation map).

In this way, a graphical representation of the correlation matrix itself may be produced in order to enable the user to readily and rapidly digest the information contained within the correlation matrix. The value of each matrix element of the correlation matrix, when graphically plotted, may be represented by a colour coding, for example, to give a colour map. In another approach, the value of each matrix element of the correlation matrix, when graphically plotted, may be represented by a vector or point, thereby defining a surface or "terrain" plot or "contour" plot, collectively with the other correlation matrix element values so represented.

Selected parts or regions of interest within the array of correlation matrix elements may be graphically represented—such as the correlation values associated with a specific row/column of the matrix, or a group/band of neighbouring rows/columns. For example, a particular row of the correlation matrix may be presented as a correlation spectrum, where correlation matrix elements are plotted versus the measurement variables (e.g., chemical shifts).

Also, it may be especially useful to present a particular row of the covariance matrix as a covariance spectrum, where covariance matrix elements are plotted versus the measurement variables (e.g., chemical shifts), and each point is plotted with a colour that indicates the value of the associated correlation matrix element. Thus, the row of the covariance matrix give the shape, and the corresponding row of the correlation matrix gives the colour.

A graphical representation of the correlation matrix as a surface or "terrain" plot or "contour" plot may be useful. When NMR spectral data has been used, the plot may be interpreted in a manner analogous to that used to interpret conventional TOCSY spectra. For example, coupling constants, J, can be determined in same manner. However, as discussed in the examples below, the STOCSY analysis yields much higher resolution data, and permits much more structural information to be extracted.

Note also that, whereas conventional TOCSY data usually only reveal "coupling" between proximal parts of a chemical species giving rise to NMR signal intensity, STOCSY usually reveals "correlation" between all parts of a given chemical species giving rise to NMR signal intensity, and therefore often greatly assists peak assignment and structural determination of the chemical species under investigation.

1-Dimensional STOCSY:

Note that, in order to generate the correlation measures associated with correlation between a specific measurement(s) (i.e. value(s) of measurement variable) located within the spectra, and some other specific measurement(s) located elsewhere within the spectra, one need only calculate the matrix element(s) of the correlation matrix which have matrix co-ordinates associated with the specific measurements (measurement variable value(s)) in question. That is, one need not calculate the whole correlation matrix in order to do this. For example, if one is only interested in the correlation measures associated with a particular measurement variable (e.g., a particular chemical shift value, e.g., $\delta$ 5,217), then it is only necessary to calculate the corresponding row of the correlation matrix.

Thus, one aspect of the present invention pertains to a method of identifying a sample constituent (e.g., a chemical species) on the basis of measurement values (e.g., NMR signal intensity values) for corresponding measurement variables (e.g., chemical shifts) that are correlated, specifically as determined by generating a measure of the correlation between: the measurement values (e.g., NMR signal intensity values) in spectra of a first set of spectra corresponding to the measurement variable (e.g., chemical shift) of interest, and measurement values (e.g., NMR signal intensity values) corresponding to some or all measurement variables (e.g., chemical shifts) in a spectrum of a second set of spectra.

Thus, one aspect of the present invention pertains to a method of identifying a sample constituent of a sample, the method comprising the steps of:

(a) providing a plurality of spectra defining a first set of spectra, wherein each spectrum of said set of spectra is a spectrum of measurement values derived from different measurements of a property of a sample comprising said sample constituent, each measurement value corresponding to one of a range of measurement variables defining the spectrum;

(b) providing a plurality of spectra defining a second set of spectra, wherein each spectrum of said set of spectra is a spectrum of measurement values derived from different measurements of a property of a sample comprising said sample constituent, each measurement value corresponding to one of a range of measurement variables defining the spectrum;

(c) selecting a measurement variable of interest from a spectrum of the first set of spectra; and (d) generating a measure of the correlation between: the measurement values in the spectra of the first set of spectra corresponding to the measurement variable of interest, and measurement values corresponding to some or all of the measurement variables in the spectra of the second set of spectra;

(e) generating association data through which the measurement variable of interest in any spectrum of the first set of spectra, and a measurement variable in any spectrum of the second set of spectra is associated to the measure of correlation between: the measurement values of the respective measurement variables;

(f) identifying said sample constituent using the measure of correlation and the association data.

In one embodiment, step (a) is generating a plurality of spectra defining a first set of spectra.

In one embodiment, step (b) is generating a plurality of spectra defining a second set of spectra.

In one embodiment, said first set of spectra and said second set of spectra are identical. In one embodiment, said first set of spectra and said second set of spectra are different.

In one embodiment, said plurality of spectra (e.g., defining a first set of spectra, defining a second set of spectra) is at least 3, e.g., at least 5, e.g., at least 10, e.g., at least 20, e.g., at least 50, e.g., at least 100).

Again, note that, in this context, "spectrum" and "spectra" are used in the mathematical sense, and refers to an array or arrays of data, i.e., an array or arrays of measurement values and corresponding measurement variables. This is distinct from the term "spectral data," which, as used herein, refers to data that is spectroscopic data (e.g., NMR data, UV absorption data, IR absorption data) (e.g., an NMR spectrum, a UV absorption spectrum, an IR absorption spectrum) or spectrometric data (e.g., mass spectrum data) (e.g., a mass spectrum). In one embodiment, the "spectrum" is, or comprises, an array of spectral data. In one embodiment, the "spectrum" is, or comprises, or additionally comprises, other non-spectral data, such as metabonomic, proteomic, transcriptomic, and/or genomic data.

In one embodiment, the method is a method of identifying a sample constituent (e.g., a chemical species) from a spectrum (e.g., an NMR spectrum) of measurement values (e.g., NMR signal intensity values) derived from different measurements of a property (e.g., NMR signal) of a sample comprising said sample constituent, each measurement value (e.g., NMR signal intensity value) corresponding to one of a range of measurement variables (e.g., chemical shifts) defining the spectrum, the method comprising the steps of:

(a) providing a plurality of said spectra defining a first set of spectra (e.g., NMR spectra);

(b) providing a plurality of said spectra defining a second set of spectra (e.g., NMR spectra);

(c) selecting a measurement variable (e.g., chemical shift) of interest from a spectrum of one of the first and second sets;

(d) generating a measure of the correlation between: the measurement values (e.g., NMR signal intensity values) in the spectra of the first set of spectra corresponding to the measurement variable (e.g., chemical shift) of interest, and measurement values (e.g., NMR signal intensity values) corresponding to some or all measurement variables (e.g., chemical shifts) in the spectra of the second set of spectra;

(e) generating association data with which the measurement variable (e.g., chemical shift) of interest in any spectrum of the first set of spectra, and a measurement variable (e.g., chemical shift) in any spectrum of the second set of spectra is associated to the measure of correlation between: the measurement values (e.g.,
NMR signal intensity values) of the respective measurement variables (e.g., chemical shifts);

(f) identifying said sample constituent using the measure of correlation and the association data.

Again, note that although these methods are described herein primarily with reference to NMR spectral data, these methods are also applicable to other types of spectral data and/or non-spectral data. For example, the "spectrum" may be a mass spectrum (MS); the "measurement values" may be mass spectral intensity values (e.g., integrated ion counts, etc.); the "property" may be mass spectral ion signal; the "measurement variables" may be mass-to-charge (m/z) ratios; etc. Similarly, for example, the "spectrum" may be an infrared (IR) spectrum (e.g., a Fourier transform infrared (FTIR) spectrum); the "measurement values" may be infrared absorption values; the "property" may be infrared absorption; the "measurement variables" may be wave number (i.e., reciprocal wavelength); etc. Similarly, for example, the "spectrum" may be an array of proteomic data; the "measurement values" may be protein levels; the "property" may be the amount of protein; the "measurement variables" may be a name or label associated with the protein; etc.

In one embodiment, step (a) is generating a plurality of said spectra defining a first set of spectra (e.g., NMR spectra).

In one embodiment, step (b) is generating a plurality of said spectra defining a second set of spectra (e.g., NMR spectra).

In one embodiment, said first set of spectra and said second set of spectra are identical. In one embodiment, said first set of spectra and said second set of spectra are different.

This aspect may be illustrated with reference to the three spectra (A, B, and C) exemplified above. Wishing to know, for example, the degree of correlation between the measurement values in the three spectra corresponding to measurement "1" (the value "1" of the measurement variable, e.g., NMR signal intensity, at chemical shift $\delta_1$), and all of the measurement values (values 1, 2 and 3 of the measurement variable, e.g., NMR signal intensity, at chemical shifts $\delta_1$, $\delta_2$, and $\delta_3$), one need only calculate the correlation matrix elements of the first row (or column) of the correlation matrix C—namely:

$$C_{1,j} = \frac{1}{2}\sum_{k=1}^{3}\left(\frac{x_{k,j} - \overline{x}_i}{s_i}\right) \cdot \left(\frac{x_{k,j} - \overline{x}_j}{s_j}\right)$$

These three vector element values may be generated using the whole of the spectrum of all three spectra (spectra A, B, and C). Element $C_{1,j}$ provides a measure of the correlation of the measurement values $x_{1,1}, x_{2,1}, x_{3,1}$ (e.g., NMR signal intensity at chemical shift $\delta_1$) and all the measurement values $x_{1,j}, x_{2,j}, x_{3,j}$ (e.g., NMR signal intensity at chemical shift $\delta_j$), including itself because we considered S1=S2.

These correlation values may be plotted (or represented) together with a plot of any of the three spectra (A, B, or C) in order to indicate the extent to which the parts (parts 1, 2 and 3) of the spectrum are correlated with part "1" of the spectrum. This may be most effectively done, for example, by colour-coding the parts of the plotted spectra with a colour indicative of the degree of correlation.

For example, the range of correlation (e.g., 0 to 1) may be mapped onto a range of colour (e.g., from blue to red), and the spectrum (e.g., NMR spectrum) (e.g., any one of spectra A, B, or C) may be plotted in colour, wherein each data point (e.g., corresponding to a particular chemical shift) is plotted in a colour (e.g., from blue to red) that indicates the correlation of that data point with the particular data point (e.g., chemical shift) of interest (e.g., corresponding to an NMR peak of interest). In the resulting colour-coded spectrum (e.g., NMR spectrum), those features (e.g., NMR peaks) that are "most red" are highly correlated to the feature (e.g., NMR peak) of interest, while those features (e.g., NMR peaks) that are "most blue" are less correlated to the feature (e.g., NMR peak) of interest.

In this way correlations between different parts of a given spectrum may be determined and visualised with ease of interpretation. Those parts of given spectrum that have been identified as highly correlated can be considered to arise from the same chemical species, and so may be used as an aid in determining the identity and/or structure of the chemical species.

A measurement variable of interest (e.g., a particular chemical shift; a particular peak) may be selected simply because it forms a part of an interesting or unusual part of a spectrum, such as being the peak value of a spectral resonance, for example, as determined using pattern recognition techniques.

Illustrative Flowcharts

Figure 26:
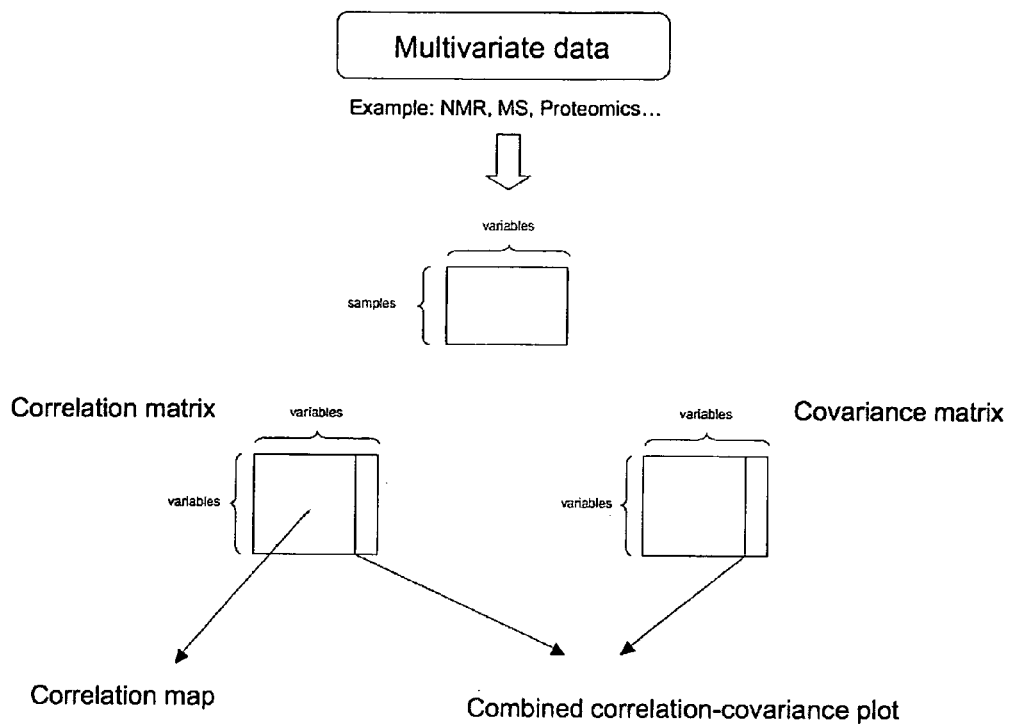
FIG. 26 is a flowchart illustrating some of the analysis methods described herein, when applied to one set of multivariate data (i.e., where S1 is equal to S2).
Figure 27:
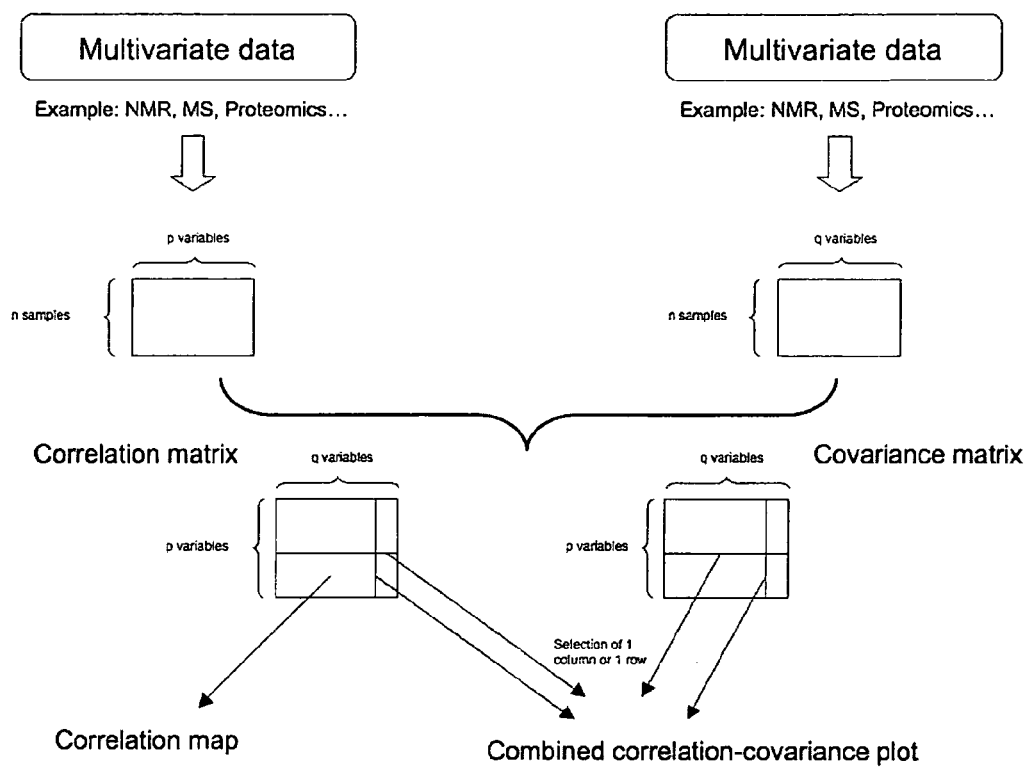
FIG. 27 is a flowchart illustrating some of the analysis methods described herein, when applied to two sets of multivariate data (i.e., where S1 is not equal to S2).

FIG. 26 and FIG. 27 are flowcharts illustrating these analysis methods.

In FIG. 26, the method is applied to one set of multivariate data (i.e., where S1 is equal to S2) (e.g., $^1$H NMR data; $^{31}$P NMR data; MS data; metabonomic data, proteomic data, transcriptomics data; genomic data; etc.). The correlation matrix and the covariance matrix are calculated as described herein. The correlation matrix may be used to present a correlation map, e.g., a contour map where the contours indicate the degree of correlation. Additionally, one column (or row) of the covariance matrix (i.e., the one associated with the variable, e.g., chemical shift, selected to be the focus of the correlation study) may be plotted and colour-coded according to the correlation, as found in the corresponding column (or row) of the correlation matrix (to yield a combined correlation-covariance plot), in order to show visually those variables that are highly correlated. This may be described as a "combined correlation-covariance plot", in which the "shape" is taken from the covariance matrix and the "colour" is taken from the correlation matrix.

In FIG. 27, the method is applied to two sets of multivariate data (i.e., where S1 is not equal to S2) (e.g., $^1$H NMR data and $^{31}$P NMR data; $^1$H NMR data and MS data; $^1$H NMR data and transcriptomics data; $^1$H NMR data and genomic data; etc.). Again, the correlation matrix and the covariance matrix are calculated as described herein. Again, the correlation matrix may be used to present a correlation map, e.g., a contour map where the contours indicate the degree of correlation. Again, one column (or row) of the covariance matrix (i.e., the one associated with the variable, e.g., chemical shift, selected to be the focus of the correlation study) may be plotted and colour-coded according to the correlation, as found in the corresponding column (or row) of the correlation matrix (to yield a combined correlation-covariance plot), in order to show visually those variables that are highly correlated. Again, this may be described as a "combined correlation-covariance plot", in which the "shape" is taken from the covariance matrix and the "colour" is taken from the correlation matrix.

One advantage of the combined correlation-covariance plot is that the covariance and the correlation are represented simultaneously for one variable, and that it allows one to display the correlation between variables without distortion of their initial relative intensities.

In very simplified terms, one embodiment of the method may be summarised as:

(1) provide a sample;
(2) provide or generate a first set of spectra (e.g., $^1$H NMR spectra for the range δ 0 to δ 10) for that sample; each spectrum forms a row in the matrix S1;
(3) provide or generate a second set of spectra (e.g., $^{31}$P NMR spectra for the range of δ 2 to δ 5) for that sample; each spectrum forms a row in the matrix S2;
(4) calculate the correlation matrix, C, and the covariance matrix, V;
(5) optionally plot the correlation matrix, C, as a correlation map; this may be useful to visualize the correlation data;
(6) select one variable of interest (e.g., one $^1$H chemical shift; one $^{31}$P chemical shift; one m/z value; one protein; one gene; etc.) to be the focus of the correlation study; this one variable will have associated with it one row (or one column) of the correlation matrix, C, and one row (or one column) of the covariance matrix, V;
(7) plot that row (or column) of the covariance matrix, V, as function of that row's variable (e.g., $^1$H chemical shift, $^{31}$P chemical shift, m/z, protein label, gene label, etc.) (to give a covariance plot), but plot it in a colour that reflects the correlation, as found in the corresponding row (or column) of the correlation matrix, C.

It is possible for the two sets of spectra to be identical, that is, S1=S2. In this case, the correlation matrix, C, and the covariance matrix, V, are both square.

It is possible for the two sets of spectra to be different, that is, S1 not equal to S2. In this case, the correlation matrix, C, and the covariance matrix, V, may not be square.

Methods of Identifying Biologically Correlated Species

As discussed herein, the methods described herein may be used to identify those measurement values/variables that are correlated, and on that basis, allow identification of a sample constituent. In the simple case of NMR, peaks/chemical shifts can be allocated to a single species on the basis of the correlation data, and then those peaks/chemical shifts assigned (e.g., using the literature) in order to make a structural assignment.

Also as discussed herein (see, for example, Study 2 and Study 5, below), correlated measurement values/variable may also be used to identify distinct interdependent species, for example, distinct species that are biologically correlated, for example, both involved in the same mechanistic and/or metabolic pathway and/or are under a common regulatory mechanism (e.g., a series of genes). The correlation may be, for example, a strong positive correlation or a strong negative correlation (or anti-correlation). This might indicate, for example, an enzyme, its susbstrate, and its product; as the amount of enzyme increases, the amount of substrate decreases, and the amount of product increases. Signals representing the substrate should be strongly anti-correlated with signals representing the product, assuming that no other reactions are involved. This type of information is particularly useful in biological studies, for example, in studies attempting to understand metabolic processes. This information is also useful in the search for biomarkers (and alternative biomarkers).

Thus, in analogy to the methods described above, one aspect of the present invention pertains to a method of identifying a plurality of biologically correlated sample constituents (e.g., chemical species) of a sample on the basis of measurement values (e.g., NMR signal intensity values) for corresponding measurement variables (e.g., chemical shifts) that are correlated, specifically as determined by generating a measure of the correlation between: each spectrum of measurement values (e.g., NMR signal intensity values) in a first set of spectra and each spectrum of measurement values (e.g., NMR signal intensity values) in a second set of spectra. Note that, in this context, "spectrum" and "spectra" are used in the mathematical sense—see below.

Thus, in analogy to the methods described above, one aspect of the invention pertains to a method of identifying a plurality of biologically correlated sample constituents of a sample, the method comprising the steps of:

(a) providing a plurality of spectra defining a first set of spectra, wherein each spectrum of said set of spectra is a spectrum of measurement values derived from different measurements of a property of a sample comprising said first sample constituent and said second sample constituent, each measurement value corresponding to one of a range of measurement variables defining the spectrum;

(b) providing a plurality of spectra defining a second set of spectra, wherein each spectrum of said set of spectra is a spectrum of measurement values derived from different measurements of a property of a sample comprising said first sample constituent and said second sample constituent, each measurement value corresponding to one of a range of measurement variables defining the spectrum;

(c) generating a measure of the correlation between: each spectrum of measurement values in the first set of spectra and each spectrum of measurement values in the second set of spectra;

(d) generating association data through which a particular measurement variable in any spectrum of the first set of spectra, and a particular measurement variable in any spectrum of the second set of spectra, is associated to the measure of correlation between: the measurement values of the respective given measurement variables;

(e) identifying said plurality of biologically correlated sample constituents using the measure of correlation and the association data.

Methods of Identifying Biomarkers

As discussed above, another aspect of the present invention pertains to new methods of identifying biomarkers (e.g., chemical species) that are useful in classification (e.g., in diagnosis). In general, pattern recognition methods are applied to modelling data of known classes (e.g., with disease, without disease) that is, or comprises, spectral data (e.g., NMR spectral data), in order to determine those parts of the spectrum (e.g., those peaks of the NMR spectrum) that are highly discriminant (e.g., are useful in discriminating between classes). Having identified particular parts of the spectrum (e.g., peaks in the NMR spectrum) that are useful in discrimination, STOCSY analysis (as described above) is applied to those parts of the spectrum (e.g., peaks in the NMR spectrum) in order to identify the underling chemical species that is/are highly discriminant (e.g., that is/are useful in discriminating between classes).

As discussed above in connection with the STOCSY methods, the step of selecting a measurement variable (e.g., chemical shift) of interest may be performed either subjectively, by application of skill and judgement of the user, and/or by application of methods for objectively identifying which measurement within a spectrum (e.g., which peak, which chemical shift) has a measurement value (e.g., an NMR signal intensity) which is likely to possess a relatively high degree of correlation with other criteria (e.g., other measurements in the spectrum, class membership, etc.).

For example, pattern recognition techniques may be employed in this selection step. Such pattern recognition techniques may be applied alone or in combination, with other pattern recognition techniques and/or other statistical analysis techniques, in order to select a measurement (e.g., chemical shift) of interest, as discussed in more detail below.

In a simple, but illustrative example, a data set comprising NMR spectral data is provided representing the classes of interest. The data set may be, for example, a set of NMR spectra consisting of one NMR spectrum for each of a number of samples taken from individuals representing the different classes. So, for example, a study population might comprise 100 individuals: 50 that are known to be in one class (e.g., with a particular disease) and 50 that are known to be in another class (e.g., without the disease). A sample (e.g., a blood sample, a urine sample, etc.) is collected from each individual, and NMR data (e.g., an NMR spectrum) collected for each sample. Some or all of this NMR data (e.g., all or parts of the NMR spectra), together with an indicator of the class membership (e.g., indicating the class of the individual, with disease, without disease), and optionally together with other data (e.g., other spectral data, such as mass spectral data, other non-spectral data, such as clinical data), form a data vector (in this example, the data set comprises 100 data vectors). This data set is then modelled using a supervised mathematical model using conventional modelling methods (e.g., PLS-DA, etc.). From the mathematical model, it is possible to calculate those variables (e.g., descriptors, e.g., chemical shifts) that are responsible for separation in the model, e.g., for discrimination of one class from the other class or classes.

Having identified those class-discriminant variables (e.g., descriptors, e.g., chemical shifts) that are more responsible for separation in the model, e.g., for discrimination of one class from the other class or classes, it may be possible to identify the underlying class-discriminant chemical species (e.g., biomarker(s)) directly, for example, using conventional NMR assignment tables. However, this is often difficult or impossible with NMR spectra for complex mixtures, such as urine and blood. By additionally applying methods similar to the STOCSY methods described above, it is possible to identify other variables (e.g., descriptors, e.g., chemical shifts) that are correlated with the class-discriminant variable of interest, and use the identity of those other variables (e.g., chemical shifts) to identify the underlying class-discriminant chemical species (e.g., biomarker(s)).

Thus, one aspect of the present invention pertains to a method of identifying a class-discriminant chemical species (e.g., biomarker) for a particular class membership (e.g., with disease, without disease) on the basis of measurement values (e.g., NMR signal intensity values) for corresponding measurement variables (e.g., chemical shifts) that are correlated, specifically as determined by generating a measure of the correlation between: the measurement value (e.g., NMR signal intensity value) of a class-discriminant measurement variable (e.g., class-discriminant chemical shift) of interest, and the measurement values (e.g., NMR signal intensity values) of some or all of the other measurement variables (e.g., other chemical shifts) in a data vector comprising, at least, spectral data (e.g., NMR spectral data), where the class-discriminant measurement variable (e.g., class-discriminant chemical shift) of interest is selected on the basis of correlation with the particular class, as determined using a supervised mathematical model (e.g., PLS-DA).

Thus, one aspect of the present invention pertains to a method of identifying a class-discriminant chemical species (e.g., biomarker) for a particular class membership (e.g., with disease, without disease), comprising the steps of:

(a) providing a data set that comprises a plurality of data vectors (e.g., 5 or more) for each of a plurality of classes (e.g., with disease, without disease), each data vector comprising, at least, a spectrum and a class representation variable (e.g., indicating class membership), wherein said spectrum comprises measurement values derived from different measurements of a property of a sample representative of one of said plurality of classes, each measurement value corresponding to one of a range of measurement variables;

(b) modelling said data set using a supervised mathematical model (e.g., PLS-DA);

(c) calculating the degree of correlation between: measurement variables and class representation variables (e.g., with disease, without disease) of the supervised mathematical model (e.g., calculating the model correlation coefficients, e.g., loadings);

(d) identifying class-discriminant measurement variables as those measurement variables that are correlated (preferably, have a relatively high degree of correlation) with the particular class, thereby being discriminant for the particular class (e.g., identifying those measurement variables associated with large magnitude correlation coefficients, e.g., large magnitude loadings);

(e) selecting a class-discriminant measurement variable of interest according to the degree of correlation (preferably a high degree of correlation) with the particular class;

(f) generating a measure of the correlation between: the measurement value of the class-discriminant measurement variable of interest, and measurement values corresponding to some or all of the other measurement variables, (g) identifying correlated measurement variables of measurement values that are relatively highly correlated with the measurement value of the class-discriminant measurement variable of interest;

(h) identifying said class-discriminant chemical species (e.g., biomarker) for the particular class membership (e.g., with disease, without disease) using said correlated measurement variables.

Again, note that, in this context, "spectrum" and "spectra" are used in the mathematical sense, and refers to an array or arrays of data, i.e., an array or arrays of measurement values and corresponding measurement variables. This is distinct from the term "spectral data," which, as used herein, refers to data that is spectroscopic data (e.g., NMR data, UV absorption data, IR absorption data) (e.g., an NMR spectrum, a UV absorption spectrum, an IR absorption spectrum) or spectrometric data (e.g., mass spectrum data) (e.g., a mass spectrum). In one embodiment, the "spectrum" is, or comprises, an array of spectral data. In one embodiment, the "spectrum" is, or comprises, or additionally comprises, other non-spectral data, such as metabonomic, proteomic, transcriptomic, and/or genomic data.

In one embodiment, the method is a method of identifying a class-discriminant chemical species (e.g., biomarker) for a particular class membership (e.g., with disease, without disease), comprising the steps of:

(a) providing a data set that comprises a plurality of data vectors (e.g., 5 or more) for each of a plurality of classes (e.g., with disease, without disease), each data vector comprising, at least, spectral data (e.g., NMR spectral data) and a class representation variable (e.g., indicating class membership), wherein said spectral data (e.g., NMR spectral data) comprises measurement values (e.g., NMR signal intensity values) derived from different measurements of a property (e.g., NMR signal) of a sample representative of one of said plurality of classes, each measurement value (e.g., NMR signal intensity value) corresponding to one of a range of measurement variables (e.g., chemical shifts);

(b) modelling said data set using a supervised mathematical model (e.g., PLS-DA);

(c) calculating the degree of correlation between: measurement variables (e.g., chemical shifts) and class representation variables (e.g., with disease, without disease), of the supervised mathematical model (e.g., calculating the model correlation coefficients, e.g., loadings);

(d) identifying class-discriminant measurement variables (e.g., class-discriminant chemical shifts) as those measurement variables that are correlated (preferably, have a relatively high degree of correlation) with the particular class, thereby being discriminant for the particular class (e.g., identifying those chemical shifts associated with large magnitude correlation coefficients, e.g., large magnitude loadings);

(e) selecting a class-discriminant measurement variable (e.g., a class-discriminant chemical shift) of interest according to the degree of correlation (preferably a high degree of correlation) with the particular class;

(f) generating a measure of the correlation between: the measurement value (e.g., NMR signal intensity value) of the class-discriminant measurement variable (e.g., class-discriminant chemical shift) of interest, and the measurement values (e.g., NMR signal intensity values) of some or all of the other measurement variables (e.g., other chemical shifts) in a data vector, (g) identifying correlated measurement variables (e.g., correlated chemical shifts) of measurement values (e.g., NMR signal intensity values) that are relatively highly correlated with the measurement value (e.g., NMR signal intensity value) of the class-discriminant measurement variable (e.g., a class-discriminant chemical shift) of interest;

(h) identifying said class-discriminant chemical species (e.g., biomarker) for the particular class membership (e.g., with disease, without disease) using said correlated measurement variables (e.g., correlated chemical shifts).

In one embodiment, step (a) is generating a data set, as defined above.

In one embodiment, said plurality of data vectors is at least 3, e.g., at least 5, e.g., at least 10, e.g., at least 20, e.g., at least 50, e.g., at least 100).

In one embodiment, said plurality of classes is at least 2, e.g., at least 3, e.g., at least 5.

A "supervised" mathematical methods or model is one that provides a means of discriminating between classes of samples, of spectra, etc., by analysis of correlations between data vectors representing those samples, spectra, etc.

Examples of suitable supervised mathematical methods and models include pattern recognition models such as Partial Least Squares—Discriminant Analysis (also known as Projection of Latent Structure—Discriminant Analysis) (PLS-DA).

An "orthogonal" supervised mathematical method or model may be employed which removes from measures of the variation in the descriptor variables (e.g., NMR spectra) any systematic variation in those variables which is orthogonal to the variables in the model that represent and/or discriminate class. That is to say, variation in the input data set that is not related to the class variables is removed, so as to permit clearer interpretation of remaining variations in the data set.

Examples of suitable orthogonal supervised methods and models include Orthogonal Partial Least Squares—Discriminant Analysis (O-PLS-DA), and Partial Least Squares (PLS) with Orthogonal Signal Correction (OSC)—OSC serving to remove orthogonal variations from the data set.

In step (d), class-discriminant measurement variables (e.g., class-discriminant chemical shifts) are identified on the basis of correlation (preferably, a relatively high degree of correlation) with the particular class. This may be done the basis of the magnitude of the correlation coefficients (e.g., PLS coefficients) or loadings, e.g., reflecting the correlation between: the measurement variable (e.g., chemical shift) and a class-representation variable (e.g., the variable reflecting class membership).

For example, step (d) may include calculating the PLS-DA (or O-PLS-DA, etc.) coefficients and graphically representing those coefficients as a function of the measurement variable (e.g., chemical shift) of the spectra of the set, and identifying those parts of the plot of coefficients that are associated with class-discriminant measurement variables (e.g., class-discriminant chemical shifts).

In this way, it is possible to identify class-discriminant PLS coefficients in a plot of PLS coefficients for a model. This may assist the user with the rapid visual identification of class-discriminant measurement variables (e.g., chemical shifts), and thereby assist the user with the identification of the underlying chemical species (e.g., biomarker). This may also assist the user with the rapid visual identification of combinations of class-discriminant measurement variables, and thereby identification of the underlying chemical species (e.g., biomarker(s)), or a combination of several underlying chemical species (e.g., biomarker combination).

It has been found that models based on mean centred data sets are often poor, because large, but variable, measurement values (e.g., NMR signal intensity values), that do not reflect class membership, may dominate the model.

It has also been found that models based on unit variance (UV) scaled data reduce the effect of such large, but variable, measurement values. For example, large PLS coefficients derived from a discriminant PLS model of a unit variance (UV) scaled data set—when expressed as a function of the measurement variables (e.g., chemical shift)—are often suitable indicators of the correlation between the measurement variables (e.g., chemical shift) of a data set and the class representation variables (e.g., that indicate class membership). This is primarily due to the fact that discriminant modelling of a UV scaled spectral set enhances PLS coefficients which are associated with "steady" measurement variables—having a relatively low standard deviation—and suppresses PLS coefficients associated with "unsteady" measurement variables—having a relatively high standard deviation. Consequently, a plot of PLS coefficients for a model of UV-scaled spectral set possesses peaks occurring only at relatively steady regions of the measurement variable, and has small or no peaks at relatively unsteady regions of measurement variable. Steady measurement variables are more likely to be class-discriminant measurement variables than unsteady ones.

Consequently, step (b) above may be achieved, for example, using a method comprising the steps of:
(i) calculating the standard deviation of the measurement value (e.g., NMR signal intensity value) associated with each measurement variable (e.g., chemical shift), in the data set (e.g., calculating, for each chemical shift, the standard deviation of the NMR signal intensity value at that chemical shift, using all of the NMR spectral data in the data set);
(ii) scaling the NMR spectral data by dividing each measurement value (e.g., NMR signal intensity value) in the data set by the standard deviation thereof (e.g., for each NMR signal intensity value, dividing it by the standard deviation calculated for NMR signal intensity values at that chemical shift, as calculated in (i));
(iii) modelling the scaled data set using a supervised mathematical model (e.g., PLS-DA, O-PLS-DA), including calculating the model coefficients (e.g., PLS coefficients or loadings) for a scaled spectrum chosen from the scaled set.

However, it may be difficult to extract the identity of the class-discriminant variables solely from conventional plots of the PLS coefficients versus the measurement variables (e.g., chemical shifts).

This difficulty may be overcome, for example, by "back scaling" the PLS coefficients, and then plotting (in an appropriate manner) the resulting back-scaled UV-scaled PLS coefficients along with the original UV-scaled PLS coefficients. Back-scaling the PLS coefficients is achieved by multiplying each of the PLS coefficients, as derived from the UV scaled data set, with the standard deviation of the measurement value for the measurement variable with which the PLS coefficient is associated, thereby reversing the UV scaling effect on the PLS coefficients.

For example, the range of the magnitude of the original UV-scaled PLS coefficients may be mapped onto a range of colour (e.g., from blue to red), and the back-scaled UV-scaled PLS coefficients may be plotted in colour, wherein each data point (e.g., corresponding to a particular back-scaled UV-scaled PLS coefficient at a particular chemical shift) is plotted in a colour (e.g., from blue to red) that indicates the corresponding original UV-scaled PLS coefficient. In the resulting colour-coded plot, those features (e.g., NMR peaks) that are "most red" appear at the more important class-discriminant measurement variables, while those features (e.g., NMR peaks) that are "most blue" appear at the less important class-discriminant measurement variables.

Alternatively, more important class-discriminant variables may be identified by modelling the data set (calculating correlation coefficients or loadings) twice, using two differently-scaled (e.g., mean centered, unit variance scaled) versions of the data set, and then combining (e.g., "double-mapping") the results (e.g., correlation coefficient, loadings) in order to provide a much better indication of those variables (e.g., descriptors, e.g., chemical shifts) that are more responsible for separation in the model, and/or for discrimination of one class from the other class or classes.

For example, PLS coefficients may be calculated for both the mean centered data set, and for the UV-scaled data set. The range of the magnitude of the UV-scaled PLS coefficients may be mapped onto a range of colour (e.g., from blue to red), and the mean centered PLS coefficients may be plotted in colour, wherein each data point (e.g., corresponding to a particular mean centered PLS coefficient at a particular chemical shift) is plotted in a colour (e.g., from blue to red) that indicates the corresponding UV-scaled PLS coefficient. In the resulting colour-coded plot, those features (e.g., NMR peaks) that are "most red" appear at the more important class-discriminant measurement variables, while those features (e.g., NMR peaks) that are "most blue" appear at the less important class-discriminant measurement variables.

Steps (f), (g), and (h) are similar to the 1-Dimensional STOCSY methods described above, for example, where the measurement variable of interest (e.g., a particular chemical shift; a particular peak) is selected because it is a class-discriminant measurement variable (e.g., a class-discriminant chemical shift) with a high degree of correlation with the particular class.

Note that a plurality of class-discriminant measurement variables (e.g., discriminant chemical shifts) may be identified in step (d), and that none, some, or all of these class-discriminant measurement variables (e.g., discriminant chemical shifts) may be correlated with other class-discriminant measurement variables (e.g., discriminant chemical shifts), as determined, for example, using the STOCSY methods described above.

That is to say, the measurement value (e.g., NMR signal intensity) corresponding to one class-discriminant measurement variable (e.g., a particular chemical shift) may be correlated with the measurement value (e.g., NMR signal intensity) corresponding with a different class-discriminant measurement variable (e.g., another particular chemical shift). This might indicate that the two class-discriminant measurement variables (e.g., class-discriminant chemical shifts) arise from the same chemical species, or that they arise from different chemical species that are metabolically related (e.g., different products along a common metabolic pathway).

Alternatively, the measurement value (e.g., NMR signal intensity) corresponding with one class-discriminant measurement variable (e.g., a particular chemical shift) may be uncorrelated with the measurement value (e.g., NMR signal intensity) corresponding with a different class-discriminant measurement variable (e.g., another particular chemical shift). This would likely indicate that the two class-discriminant measurement variables (e.g., class-discriminant chemical shifts) arise from different chemical species, and that each might be a biomarker, and additionally that the two together may form a biomarker combination.

Additional Aspects and Features

Some additional aspects and features of the invention are described below.

NMR Spectroscopy

Once again note that although the methods are described herein primarily with reference to NMR spectral data, the methods are also applicable to other types of spectral, for example, mass spectral (MS) data, infrared absorption data (e.g., FTIR), UV absorption data, and non-spectal data, such as metabonomic data, proteomic data, transcriptomic data, genomic data, etc.

Nonetheless, many preferred embodiments of the invention pertain to methods that employ NMR spectral data (e.g., NMR spectra, data obtained or derived from NMR spectra, etc.).

NMR spectroscopic techniques can be classified according to the number of frequency axes and these include 1D-, 2D-, and 3D-NMR. 1D spectra include, for example, single pulse; water-peak eliminated either by saturation or non-excitation; spin-echo, such as CPMG (i.e., edited on the basis of spin-spin relaxation); diffusion-edited, selective excitation of specific spectra regions. 2D spectra include for example J-resolved (JRES); 1H-1H correlation methods, such as NOESY, COSY, TOCSY and variants thereof; heteronuclear correlation including direct detection methods, such as HETCOR, and inverse-detected methods, such as 1H-13C HMQC, HSQC, HMBC. 3D spectra, include many variants, all of which are combinations of 2D methods, e.g. HMQC-TOCSY, NOESY-TOCSY, etc. All of these NMR spectroscopic techniques can also be combined with magic-angle-spinning (MAS) in order to study samples other than isotropic liquids, such as tissues, which are characterised by anisotropic composition.

The principal nucleus studied in biomedical NMR spectroscopy is the proton or $^1$H nucleus. This is the most sensitive of all naturally occurring nuclei. The chemical shift range is about 10 ppm for organic molecules. In addition $^{13}$C NMR spectroscopy using either the naturally abundant 1.1% $^{13}$C nuclei or employing isotopic enrichment is useful for identifying metabolites. The $^{13}$C chemical shift range is about 200 ppm. Other nuclei find special application. These include $^{15}$N (in natural abundance or enriched), $^{19}$F (for example, for studies of drug metabolism), and $^{31}$P (for example, for studies of endogenous phosphate biochemistry).

In order to obtain an NMR spectrum, it is necessary to define a "pulse program". At its simplest, this is application of a radio-frequency (RF) pulse followed by acquisition of a free induction decay (FID)—a time-dependent oscillating, decaying voltage which is digitised in an analog-digital converter (ADC). At equilibrium, the nuclear spins are present in a number of quantum states and the RF pulse disturbs this equilibrium. The FID is the result of the spins returning towards the equilibrium state. It is necessary to choose the length of the pulse (usually a few microseconds) to give the optimum response.

This, and other experimental parameters are chosen on the basis of knowledge and experience on the part of the spectroscopist. See, for example, T. D. W. Claridge, *High-Resolution NMR Techniques in Organic Chemistry: A Practical Guide to Modern NMR for Chemists*, Oxford University Press, 2000. These are based on the observation frequency to be used, the known properties of the nucleus under study (i.e., the expected chemical shift range will determine the spectral width, the desired peak resolution determines the number of data points, the relaxation times determine the recycle time between scans, etc.). The number of scans to be added is determined by the concentration of the analyte, the inherent sensitivity of the nucleus under study and its abundance (either natural or enhanced by isotopic enrichment).

After data acquisition, a number of possible manipulations are possible. The FID can be multiplied by a mathematical function to improve the signal-to-noise ratio or reduce the peak line widths. The expert operator has choice over such parameters. The FID is then often filled by a number of zeros and then subjected to Fourier transformation. After this conversion from time-dependent data to frequency dependent data, it is necessary to phase the spectrum so that all peaks appear upright—this is done using two parameters by visual inspection on screen (now automatic routines are available with reasonable success). At this point the spectrum baseline can be curved. To remedy this, one defines points in the spectrum where no peaks appear and these are taken to be baseline. Usually, a polynomial function is fitted to these points, but other methods are available, and this function subtracted from the spectrum to provide a flat baseline. This can also be done in an automatic fashion. Other manipulations are also possible. It is possible to extend the FID forwards or backwards by "linear prediction" to improve resolution or to remove so-called truncation artefacts which occur if data acquisition of a scan is stopped before the FID has decayed into the noise. All of these decisions are also applicable to 2- and 3-dimensional NMR spectroscopy.

An NMR spectrum consists of a series of digital data points with a y value (relating to signal strength) as a function of equally spaced x-values (frequency). These data point values run over the whole of the spectrum. Individual peaks in the spectrum are identified by the spectroscopist or automatically by software and the area under each peak is determined either by integration (summation of the y values of all points over the peak) or by curve fitting.

A peak can be a single resonance or a multiplet (e.g., doublet, triplet) of resonances corresponding to a single type of nucleus in a particular chemical environment (e.g., the two protons ortho to the carboxyl group in benzoic acid). Integration is also possible of the 3-dimensional peak volumes in 2-dimensional NMR spectra. The intensity of a peak in an NMR spectrum is proportional to the number of nuclei giving rise to that peak (if the experiment is conducted under conditions where each successive accumulated free induction decay (FID) is taken starting at equilibrium). Also, the relative intensity of peaks from different analytes in the same sample is proportional to the concentration of that analyte (again if equilibrium prevails at the start of each scan).

Thus, the term "NMR signal intensity value," as used herein, pertains to some measure related to the NMR peak area, and may be absolute or relative. NMR signal intensity may be, for example, a combination of a plurality of NMR signal intensities, e.g., a linear combination of a plurality of NMR signal intensities.

In the context of NMR signal intensity, the term "NMR" refers to any type of NMR spectroscopy.

Typically, the $^1$H observation frequency is from about 200 MHz to about 900 MHz, more typically from about 400 MHz to about 900 MHz, yet more typically from about 500 MHz to about 750 MHz. $^1$H observation frequencies of 500 and 600 MHz may be particularly preferred. Instruments with the following $^1$H observation frequencies are/were commercially available: 200, 250, 270 (discontinued), 300, 360 (discontinued), 400, 500, 600, 700, 750, 800, and 900 MHz.

Higher frequencies are used to obtain better signal-to-noise ratio and for greater spectral dispersion of resonances. This gives a better chance of identifying the molecules giving rise to the peaks. The benefit is not linear because in addition to the better dispersion, the detailed spectral peaks can move from being "second-order"—where analysis by inspection is not possible, towards "first-order," where it is. Both peak positions and intensities within multiplets change in a non-linear fashion as this progression occurs. Lower observation frequencies would be used where cost is an issue, but this is likely to lead to reduced effectiveness for classification and identification of biomarkers.

In general, NMR data is handled as a data matrix. Typically, each row in the matrix corresponds to an individual sample (often referred to as a "data vector"), and the entries in the columns are, for example, spectral intensity of a particular data point, at a particular $\delta$ or $\Delta\delta$ (often referred to as "descriptors").

It is often useful to pre-process data, for example, by addressing missing data, translation, scaling, weighting, etc.

Multivariate projection methods, such as principal component analysis (PCA) and partial least squares analysis (PLS), are so-called scaling sensitive methods. By using prior knowledge and experience about the type of data studied, the quality of the data prior to multivariate modelling can be enhanced by scaling and/or weighting. Adequate scaling and/or weighting can reveal the important and interesting variation hidden within in the data, and therefore make subsequent multivariate modelling more efficient. Scaling and weighting may be used to place the data in the correct metric, based on knowledge and experience of the studied system, and therefore reveal patterns already inherently present in the data.

If at all possible, missing data, for example, gaps in column values, should be avoided. However, if necessary, such missing data may replaced or "filled" with, for example, the mean value of a column ("mean fill"); a random value ("random fill"); or a value based on a principal component analysis ("principal component fill"). Each of these different approaches will have a different effect on subsequent pattern recognition analysis.

"Translation" of the descriptor coordinate axes can be useful. Examples of such translation include normalisation and mean centring.

"Normalisation" may be used to remove sample-to-sample variation. Many normalisation approaches are possible, and they can often be applied at any of several points in the analysis. Usually, normalisation is applied after redundant spectral regions have been removed. In one approach, each spectrum is normalised (scaled) by a factor of 1/A, where A is the sum of the absolute values of all of the descriptors for that spectrum. In this way, each data vector has the same length, specifically, 1. For example, if the sum of the absolute values of intensities for each bucket (i.e., a small range of $\delta$) in a particular spectrum is 1067, then the intensity for each bucket for this particular spectrum is scaled by 1/1067.

"Mean centring" may be used to simplify interpretation. Usually, for each descriptor, the average value of that descriptor for all samples is subtracted. In this way, the mean of a descriptor coincides with the origin, and all descriptors are "centred" at zero. For example, if the average intensity at $\delta$ 10.0-9.96, for all spectra, is 1.2 units, then the intensity at $\delta$ 10.0-9.96, for all spectra, is reduced by 1.2 units.

In "unit variance scaling" (UV scaling), data can be scaled to equal variance. Usually, the value of each descriptor is scaled by 1/StDev, where StDev is the standard deviation for that descriptor for all samples. For example, if the standard deviation for the bucket at $\delta$ 10.0-9.96, for all spectra, is 2.5 units, then the intensity for the bucket at $\delta$ 10.0-9.96, for all spectra, is scaled by 1/2.5 or 0.4. Unit variance scaling may be used to reduce the impact of "noisy" data. For example, some metabolites in biofluids show a strong degree of physiological variation (e.g., diurnal variation, dietary-related variation) that is unrelated to any pathophysiological process, class, etc. Without unit variance scaling, these noisy metabolites may dominate subsequent analysis.

"Pareto scaling" is, in some sense, intermediate between mean centering and unit variance scaling. In effect, smaller peaks in the spectra can influence the model to a higher degree than for the mean centered case. Also, the loadings are, in general, more interpretable than for unit variance based models. In pareto scaling, the value of each descriptor is scaled by 1/sqrt(StDev), where StDev is the standard deviation for that descriptor for all samples. In this way, each descriptor has a variance numerically equal to its initial standard deviation. The pareto scaling may be performed, for example, on raw data or mean centered data.

Pattern Recognition Methods

Suitable mathematical models providing an efficient way to investigate complex multiparametric data in a metabonomic approach include computer-based "pattern recognition" (PR) methods and expert systems. These statistical tools are similar to those currently being explored by workers in the fields of genomics and proteomics.

Pattern recognition (PR) methods can be used to generate scientific hypotheses and to test hypotheses. There are two main approaches. One set of methods is termed "unsupervised" and these simply reduce data complexity in a rational way and also produce display plots that can be interpreted by the human eye. The other approach is termed "supervised" whereby a training set of samples with known class or outcome is used to produce a mathematical model and this is then evaluated with independent validation data sets.

Unsupervised PR methods are used to analyse data without reference to any other independent knowledge, for example, without regard to the identity or nature of a xenobiotic or its mode of action. Examples of unsupervised pattern recognition methods include principal component analysis (PCA), hierarchical cluster analysis (HCA), and non-linear mapping (NLM).

One of the most useful and easily applied unsupervised PR techniques is principal components analysis (PCA). Principal components (PCs) are new variables created from linear combinations of the starting variables with appropriate weighting coefficients. The properties of these PCs are such that: (i) each PC is orthogonal to (uncorrelated with) all other PCs, and (ii) the first PC contains the largest part of the variance of the data set (information content) with subsequent PCs containing correspondingly smaller amounts of variance.

PCA, a dimension reduction technique, takes m objects or samples, each described by values in K dimensions (descriptor vectors), and extracts a set of eigenvectors, which are linear combinations of the descriptor vectors. The eigenvectors and eigenvalues are obtained by diagonalisation of the covariance matrix of the data. The eigenvectors can be thought of as a new set of orthogonal plotting axes, called principal components (PCs). The extraction of the systematic variations in the data is accomplished by projection and modelling of variance and covariance structure of the data matrix. The primary axis is a single eigenvector describing the largest variation in the data, and is termed principal component one (PC1). Subsequent PCs, ranked by decreasing eigenvalue, describe successively less variability. The variation in the data that has not been described by the PCs is called residual variance and signifies how well the model fits the data. The projections of the descriptor vectors onto the PCs are defined as scores, which reveal the relationships between the samples or objects. In a graphical representation (a "scores plot" or eigenvector projection), objects or samples having similar descriptor vectors will group together in clusters. Another graphical representation is called a loadings plot, and this connects the PCs to the individual descriptor vectors, and displays both the importance of each descriptor vector to the interpretation of a PC and the relationship among descriptor vectors in that PC. In fact, a loading value is simply the cosine of the angle which the original descriptor vector makes with the PC. Descriptor vectors which fall close to the origin in this plot carry little information in the PC, while descriptor vectors distant from the origin (high loading) are important in interpretation.

Thus a plot of the first two or three PC scores gives the "best" representation, in terms of information content, of the data set in two or three dimensions, respectively. A plot of the first two principal component scores, PC1 and PC2 provides the maximum information content of the data in two dimensions. Such PC maps can be used to visualise inherent clustering behaviour, for example, for drugs and toxins based on similarity of their metabonomic responses and hence mechanism of action. Of course, the clustering information might be in lower PCs and these have also to be examined.

Multivariate Statistical Analysis:

As discussed above, multivariate statistics analysis methods that are suitable for use in the present invention, including pattern recognition methods, are a convenient and efficient way to analyse complex data, such as NMR spectra.

For example, such analysis methods may be used to identify, for example discriminant variables and/or discriminant chemical species, for a particular condition (e.g., disease) under study.

Also, such analysis methods may be used to form a predictive model, and then use that model to classify test data. For example, one convenient and particularly effective method of classification employs multivariate statistical analysis modelling, first to form a model (a "predictive mathematical model") using data ("modelling data") from samples of known class (e.g., from subjects known to have, or not have, a particular condition), and second to classify an unknown sample (e.g., "test data"), as having, or not having, that condition.

Examples of pattern recognition methods include, but are not limited to, Principal Component Analysis (PCA) and Partial Least Squares-Discriminant Analysis (PLS-DA).

PCA is a bilinear decomposition method used for overviewing "clusters" within multivariate data. The data are represented in K-dimensional space (where K is equal to the number of variables) and reduced to a few principal components (or latent variables) which describe the maximum variation within the data, independent of any knowledge of class membership (i.e., "unsupervised"). The principal components are displayed as a set of "scores" (t) which highlight clustering, trends, or outliers, and a set of "loadings" (p) that highlight the influence of input variables on t.

The PCA decomposition can be described by the following equation:

$$X = TP' + E$$

where T is the set of scores explaining the systematic variation between the observations in X and P is the set of loadings explaining the between variable variation and provides the explanation to clusters, trends, and outliers in the score space. The non-systematic part of the variation not explained by the model forms the residuals, E.

PLS-DA is a supervised multivariate method yielding latent variables describing maximum separation between known classes of samples. PLS-DA is based on PLS which is the regression extension of the PCA method explained earlier. When PCA works to explain maximum variation between the studied samples PLS-DA suffices to explain maximum separation between known classes of samples in the data (X). This is done by a PLS regression against a "dummy vector or matrix" (Y) carrying the class separating information. The calculated PLS components will thereby be more focused on describing the variation separating the classes in X if this information is present in the data. From an interpretation point of view all the features of PLS can be used, which means that the variation can be interpreted in terms of scores (t,u), loadings (p,c), PLS weights (w) and regression coefficients (b). The fact that a regression is carried out against a known class separation means that the PLS-DA is a supervised method and that the class membership has to be known prior to the actual modelling. Once a model is calculated and validated it can be used for prediction of class membership for "new" unknown samples. Judgement of class membership is done on basis of predicted class membership (Ypred), predicted scores (tpred) and predicted residuals (DmodXpred) using statistical significance limits for the decision.

In PLS, the variation between the objects in X is described by the X-scores, T, and the variation in the Y-block regressed against is described in the Y-scores, U. In PLS-DA the Y-block is a "dummy vector or matrix" describing the class membership of each observation. Basically, what PLS does is to maximize the covariance between T and U. For each component, a PLS weight vector, w, is calculated, containing the influence of each X-variable on the explanation of the variation in Y. Together the weight vectors will form a matrix, W, containing the variation in X that maximizes the covariance between the scores T and U for each calculated component. For PLS-DA this means that the weights, W, contain the variation in X that is correlated to the class separation described in Y. The Y-block matrix of weights is designated C. A matrix of X-loadings, P, is also calculated. These loadings are apart from interpretation used to perform the proper decomposition of X.

The PLS decomposition of X and Y can hence be described as follows:

$$X=TP'+E$$

$$Y=TC'+F$$

The PLS regression coefficients, B, are then given by:

$$B=W(P'W)^{-1}C'$$

The estimate of Y, $Y_{hat}$, can then be calculated according to the following formula:

$$Y_{hat}=XW(P'W)^{-1}C'=XB$$

Both of the pattern recognition algorithms exemplified herein (PCA, PLS-DA) rely on extraction of linear associations between the input variables. When such linear relationships are insufficient, neural network-based pattern recognition techniques can in some cases improve the ability to classify individuals on the basis of the many inter-related input variables. Nevertheless, the methods are sufficiently powerful to allow classification of the individuals studied, and they provide an additional benefit over neural network methods in that they allow some information to be gained as to what aspects of the input dataset were particularly important in allowing classification to be made.

Spurious or irregular data in spectra ("outliers"), which are not representative, are preferably identified and removed. Common reasons for irregular data ("outliers") include spectral artefacts such as poor phase correction, poor baseline correction, poor chemical shift referencing, poor water suppression, and biological effects such as bacterial contamination, shifts in the pH of the biofluid, toxin- or disease-induced biochemical response, and other conditions, e.g., pathological conditions, which have metabolic consequences, e.g., diabetes.

Outliers are identified in different ways depending on the method of analysis used. For example, when using principal component analysis (PCA), small numbers of samples lying far from the rest of the replicate group can be identified by eye as outliers. A more objective means of identification for PCA is to use the Hotelling's T Test which is the multivariate version of the well known Student's T test used in univariate statistics. For any given sample, the T2 value can be calculated and this is compared with a standard value within which a chosen fraction (e.g., 95%) of the samples would normally lie. Samples with T2 values substantially outside this limit can then be flagged as outliers.

"Orthogonal" Models:

An "orthogonal" supervised mathematical method or model may be employed which removes from measures of the variation in the descriptor variables (e.g., NMR spectra) any systematic variation in those variables which is orthogonal to the variables in the model that represent and/or discriminate class. That is to say, variation in the input data set that is not related to the class variables is removed, so as to permit clearer interpretation of remaining variations in the data set.

Examples of orthogonal supervised methods and models include Orthogonal Partial Least Squares—Discriminant Analysis (O-PLS-DA), and Partial Least Squares (PLS) with Orthogonal Signal Correction (OSC)—OSC serving to remove orthogonal variations from the data set.

In O-PLS and O-PLS-DA is a multivariate pattern recognition method in which the variation in a data set X (the measured values, such as NMR spectra) and the class-discriminating variables Y is separated in to three parts. The first part contains the variation common in X and Y, and the last two parts contain the variation specific to X and Y respectively. The specific variations for X and Y are known as "structured noise". An O-PLS (O-PLS-DA) model is thus written as follows:

Model of X: $X=TW'+T_{Yosc}P'_{Yosc}+E$

Model of Y: $Y=TC'+F$

Prediction of Y: $Y_{pred}=TC'$

Where the prime (') symbol indicates matrix transpose.

T represents the score matrices for X and Y, and W and C are the joint orthonormal loading matrices, respectively. E and F are the respective residual matrices for X and Y, while $T_{Yosc}$ is the score matrix orthogonal to Y, and $P_{Yosc}$ is the corresponding loading.

The O-PLS (and O-PLS-DA) method provides similar prediction to PLS. However, the interpretation of the models is improved because the structured noise is modelled separately from the variation common to X and Y. Therefore, O-PLS loading and regression coefficients allow for a more realistic interpretation than PLS which models the structured noise together with the correlated variation between X and Y. Variation in X that is unrelated to Y may disturb the multivariate modelling causing imprecise predictions.

Data Filtering:

In another orthogonal method, latent variables that are orthogonal to some variation or class index of interest are removed by "orthogonal filtering." Here, variation in the data that is not correlated to (i.e., is orthogonal to) the class separating variation of interest may be removed. Such methods are, in general, more efficient than non-orthogonal filtering methods.

Various orthogonal filtering methods have been described. One preferred orthogonal filtering method is conventionally referred to as Orthogonal Signal Correction (OSC), wherein latent variables orthogonal to the variation of interest are removed.

The class identity is used as a response vector, Y, to describe the variation between the sample classes. The OSC method then locates the longest vector describing the variation between the samples which is not correlated with the Y-vector, and removes it from the data matrix. The resultant dataset has been filtered to allow pattern recognition focused on the variation correlated to features of interest within the sample population, rather than non-correlated, orthogonal variation.

OSC is a method for spectral filtering that solves the problem of unwanted systematic variation in the spectra by removing components, latent variables, orthogonal to the response calibrated against. In PLS, the weights, w, are calculated to maximise the covariance between X and Y. In OSC, in contrast, the weights, w, are calculated to minimize the covariance between X and Y, which is the same as calculating components as close to orthogonal to Y as possible. These components, orthogonal to Y, containing unwanted systematic variation are then subtracted from the spectral data, X, to produce a filtered predictor matrix describing the variation of interest. Briefly, OSC can be described as a bilinear decomposition of the spectral matrix, X, in a set of scores, $T^{}$, and a set of corresponding loadings, $P^{}$, containing variation orthogonal to the response, Y. The unexplained part or the residuals, E, is equal to the filtered X-matrix, $X_{osc}$, containing less unwanted variation. The decomposition is described by the following equation:

$$X = T^{}P^{\prime} + E$$

$$X_{osc} = E$$

The OSC procedure starts by calculation of the first latent variable or principal component describing the variation in the data, X. The calculation is done according to the NIPALS algorithm.

$$X = tp' + E$$

The first score vector, t, which is a summary of the between sample variation in X, is then orthogonalized against response (Y), giving the orthogonalized score vector $t^*$.

$$t^* = (I - Y(Y'Y)^{-1}Y')t$$

After orthogonalization, the PLS weights, w, are calculated with the aim of making $Xw = t^*$. By doing this, the weights, w, are set to minimize the covariance between X and Y. The weights, w, are given by:

$$w = x - t^*$$

An estimate of the orthogonal score $t^{**}$ is calculated from:

$$t^{**} = Xw$$

The estimate or updated score vector $t^{}$ is then again orthogonalized to Y, and the iteration proceeds until $t^{}$ has converged. This will ensure that $t^{}$ will converge towards the longest vector orthogonal to response Y, still giving a good description of the variation in X. The data, X, can then be described as the score, $t^{}$, orthogonal to Y, times the corresponding loading vector $p^{**}$, plus the unexplained part, the residual, E.

$$X = t^{}p^{\prime} + E$$

The residual, E, equals the filtered X, $X_{osc}$, after subtraction of the first component orthogonal to the response Y.

$$E = X - t^{}p^{\prime}$$

$$X_{osc} = E$$

If more than one component needs to be removed, the same procedure is repeated using the residual, E, as the starting data matrix, X.

New external data not present in the model calculation must be treated according to filtering of the modelling data. This is done by using the calculated weights, w, from the filtering to calculate a score vector, $t_{new}$, for the new data, $X_{new}$.

$$t_{new} = X_{new}W$$

By subtracting $t_{new}$ times the loading vector from the calibration, $p^{**}$, from the new external data, $X_{new}$, the residual, $E_{new}$, will be the resulting OSC filtered matrix for the new external data.

$$E_{new} = X_{new} - t_{new}p^{**\prime}$$

If PCA suggests separation between the classes under investigation, orthogonal signal correction (OSC) can be used to optimize the separation, thus improving the performance of subsequent multivariate pattern recognition analysis and enhancing the predictive power of the model. In the examples described herein, both PCA and PLS-DA analyses were improved by prior application of OSC.

An example of a typical OSC process includes the following steps:

(a) $^1$H NMR data are segmented using AMIX, normalised, and optionally scaled and/or mean centered. The default for orthogonal filtering of spectral data is to use only mean centered data, which means that the mean for each variable (spectral bucket) is subtracted from each single variable in the data matrix.

(b) a response vector (y) describing the class separating variation is created by assigning class membership to each sample.

(c) one latent variable orthogonal to the response vector (y) is removed according to the OSC algorithm.

(d) if desired, the removed orthogonal variation can be viewed and interpreted in terms of scores (T) and loadings (P).

(e) the filtered data matrix, which contains less variation not correlated to class separation, is next used for further multivariate modelling after optional scaling and/or mean centering.

A typical unsupervised modelling process includes the following steps:

(a) optionally scaling and/or mean centering modelling data;

(b) classifying data (e.g., as control or positive, e.g., diseased);

(c) fitting the model (e.g., using PCA, PLS-DA);

(d) identifying and removing outliers, if any;

(e) refitting the model;

(f) optionally repeating (c), (d), and (e) as necessary.

Optionally (and preferably), data filtering is performed following step (d) and before step (e). Optionally (and preferably), orthogonal filtering (e.g., OSC) is performed following step (d) and before step (e).

An example of a typical PLS-DA modelling process, using OSC filtered data, includes the following steps:

(a) OSC filtered data is optionally scaled and/or mean centered.

(b) a response vector (y) describing the class separating variation is created by assigning class membership to all samples.

(c) a PLS regression model is calculated between the OSC filtered data and the response vector (y). The calculated latent variables or PLS components will be focused on describing maximum separation between the known classes.

(d) the model is interpreted by viewing scores (T), loadings (P), PLS weights (W), PLS coefficients (B) and residuals (E). Together they will function as a means for describing the separation between the classes as well as provide an explanation to the observed separation.

Once the model has been calculated, it may be verified using data for samples of known class which were not used to calculate the model. In this way, the ability of the model to accurately predict classes may be tested. This may be achieved, for example, in the method above, with the following additional step:

(e) a set of external samples, with known class belonging, which were not used in the (e.g., PLS) model calculation is used for validation of the model's predictive ability. The prediction results are investigated, fore example, in terms of predicted response ($y_{pred}$), predicted scores ($T_{pred}$), and predicted residuals described as predicted distance to model ($DmodX_{pred}$).

The model may then be used to classify test data, of unknown class. Before classification, the test data are numerically pre-processed in the same manner as the modelling data.

Interpreting the output from the pattern recognition (PR) analysis provides useful information on the biomarkers responsible for the separation of the biological classes. Of course, the PR output differs somewhat depending on the data analysis method used. As mentioned above, methods for PR and interpretation of the results are known in the art. Interpretation methods for two PR techniques (PCA and PLS-DA) are discussed briefly herein.

Interpreting PCA Results:

The data matrix (X) is built up by N observations (spectra, samples, etc.) and K variables (spectral parts carrying the biomarker information in terms of $^1$H-NMR resonances).

In PCA, the N*K matrix (X) is decomposed into a few latent variables or principal components (PCs) describing the systematic variation in the data. Since PCA is a bilinear decomposition method, each PC can be divided into two vectors, scores (t) and loadings (p). The scores can be described as the projection of each observation on to each PC and the loadings as the contribution of each variable to the PC expressed in terms of direction.

Any clustering of observations (samples) along a direction found in scores plots (e.g., PC1 versus PC2) can be explained by identifying which variables have high loadings for this particular direction in the scores. A high loading is defined as a variable that changes between the observations in a systematic way showing a trend which matches the sample positions in the scores plot. Each spectral bucket with a high loading, or a combination thereof, is defined by its $^1$H NMR chemical shift position; this is its diagnostic spectral window. These chemical shift values then allow the skilled NMR spectroscopist to examine the original NMR spectra and identify the molecules giving rise to the peaks in the relevant buckets; these are the biomarkers. This is typically done using a combination of standard 1- and 2-dimensional NMR methods.

If, in a scores plot, separation of two classes of sample can be seen in a particular direction, then examination of those loadings which are in the same direction as in the scores plots indicates which loadings are important for the class identification. The loadings plot shows points that are labelled according to the bucket chemical shift. This is the $^1$H NMR spectroscopic chemical shift that corresponds to the centre of the bucket. This bucket defines a diagnostic spectral window. Given a list of these bucket identifiers, the skilled NMR spectroscopist then re-examines the $^1$H NMR spectra and identifies, within the bucket width, which of several possible NMR resonances are changed between the two classes. The important resonance is characterised in terms of exact chemical shift, intensity, and peak multiplicity. Using other NMR experiments, such as 2-D NMR spectroscopy and/or separation of the specific molecule using HPLC-NMR-MS for example, other resonances from the same molecule are identified and ultimately, on the basis of all of the NMR data and other data if appropriate, an identification of the molecule (biomarker) is made.

In a classification situation, one procedure for finding relevant biomarkers using PCA is as follows:

(a) PCA of the data matrix (X) containing N observations belonging to either of two known classes (healthy or diseased). The description of the observations lies in the K variables containing the biomarker information in terms of $^1$H NMR resonances.

(b) Interpretation of the scores (t) to find the direction for the separation between the two known classes in X.

(c) Interpretation of loadings (p) reveals which variables have the largest impact on the direction for separation described in the scores (t). This identifies the relevant diagnostic spectral windows.

(d) Assignment of the spectral buckets or combinations thereof to certain biomarkers. This is done, for example, by interpretation of the resonances in $^1$H NMR spectra and by using previously assigned spectra of the same type as a library for assignments.

Interpreting PLS-DA Results:

In PLS-DA, which is a regression extension of the PCA method, the options for interpretation are more extensive compared to the PCA case. PLS-DA performs a regression between the data matrix (X) and a "dummy matrix" (Y) containing the class membership information (e.g., samples may be assigned the value 1 for healthy and 2 for diseased classes). The calculated PLS components will describe the maximum covariance between X and Y which in this case is the same as maximum separation between the known classes in X. The interpretation of scores (t) and loadings (p) is the same in PLS-DA as in PCA. Interpretation of the PLS weights (w) for each component provides an explanation of the variables in X correlated to the variation in Y. This will give biomarker information for the separation between the classes.

Since PLS-DA is a regression method, the features of regression coefficients (b) can also be used for discovery and interpretation of biomarkers. The regression coefficients (b) in PLS-DA provide a summary of which variables in X (measurement variable) that are most important in terms of both describing variation in X and correlating to Y. This means that variables with high regression coefficients are important for separating the known classes in X since the Y matrix against which it is correlated only contains information on the class identity of each sample.

Again, as discussed above, the scores plot is examined to identify important loadings, diagnostic spectral windows, relevant NMR resonances, and ultimately the associated biomarkers.

In a classification situation, one procedure for finding relevant biomarkers using PLS-DA is as follows:

(a) A PLS model between the N*K data matrix (X) against a "dummy matrix" Y, containing information on class membership for the observations in X, is calculated yielding a few latent variables (PLS components) describing maximum separation between the two classes in X (e.g., healthy and diseased).

(b) Interpretation of the scores (t) to find the direction for the separation between the two known classes in X.

(c) Interpretation of loadings (p) revealing which measurement variables have the largest impact on the direction for separation described in the scores (t).

In PLS-DA, a variable importance plot (VIP) is another method of evaluating the significance of loadings in causing a separation of class of sample in a scores plot. Typically, the VIP is a squared function of PLS weights, and therefore only positive numerical values are encountered; in addition, for a given model, there is only one set of VIP-values. Variables with a VIP value of greater than 1 are considered most influential for the model. The VIP shows each loading in a decreasing order of importance for class separation based on the PLS regression against class variable.

A (w*c) plot is another diagnostic plot obtained from a PLS-DA analysis. It shows which descriptors are mainly responsible for class separation. The (w*c) parameters are an attempt to describe the total variable correlations in the model, i.e., between the descriptors (e.g., NMR intensities at values of the measurement variable), between the NMR descriptors and the class variables, and between class variables if they exist (in the present two class case, where samples are assigned by definition to class 1 and class 2 there is no correlation). Thus for a situation in a scores plot (e.g., t1 vs. t2), if class 1 samples are clustered in the upper right hand quadrant and class 2 samples are clustered in the lower left hand quadrant, then the (w*c) plot will show descriptors also in these quadrants. Descriptors in the upper right hand quadrant are increased in class 1 compared to class 2 and vice versa for the lower left hand quadrant.

(d) Interpretation of PLS weights (w) reveals which variables in X are important for correlation to Y (class separation); these, too, are diagnostic spectral windows.

(e) Interpretation of the PLS regression coefficients (b) reveals an overall summary of which variables have the largest impact on the direction for separation described in the scores; these, too, are diagnostic spectral windows.

In a typical regression coefficient plot for $^1$H NMR, each bar represents a spectral region (e.g., 0.04 ppm) and shows how the $^1$H NMR profile of one class of samples differs from the $^1$H NMR profile of a second class of samples. A positive value on the x-axis indicates there is a relatively greater concentration of metabolite (assigned using NMR chemical shift assignment tables) in one class as compared to the other class, and a negative value on the x-axis indicates a relatively lower concentration in one class as compared to the other class.

(f) Assignment of the measurement variables or combinations thereof to certain biomarkers. This is done, for example, by interpretation of the resonances in $^1$H NMR spectra and by using previously assigned spectra of the same type as a library for assignments.

Classes and Predetermined Conditions

Certain aspects of the invention refer to "classes" and "classification." A thing is classified, that is, it is assigned membership to a particular class (i.e., it is assigned class membership), and is said "to be of," "to belong to," "to be a member of," a particular class.

As used herein, the term "condition" relates to a state that is, in at least one respect, distinct from another state, as determined by a suitable control population. For example, "presence of a predetermined condition" may be one class, and "absence of a predetermined condition" may be another class. A condition is "predetermined" in the sense that it is the condition in respect to which the invention is practised; a condition is predetermined by a step of selecting a condition for considering, study, etc.

Included among conditions is the state of "at risk of" a condition, "predisposition towards a" condition, and the like, again as compared to the state of normality, as determined by a suitable control population. In this way, a disease, state of the disease, severity of the disease, at risk of the disease, and predisposition towards the disease are all conditions (and are also conditions associated with the disease).

Included among conditions is the degree of a condition, for example, the progress or phase of a disease, or a recovery therefrom. For example, each of different states in the progress of a disease, or in the recovery from a disease, are themselves conditions. In this way, the degree of a condition may refer to how temporally advanced the condition is. Another example of a degree of a condition relates to its maximum severity, e.g., a disease can be classified as mild, moderate or severe). Yet another example of a degree of a condition relates to the nature of the condition (e.g., anatomical site, extent of tissue involvement, etc.).

Samples

As discussed above, many aspects of the present invention pertain to methods that involve a sample, e.g., a particular sample under study ("study sample").

In general, a sample may be in any suitable form. For methods which involve spectra obtained or recorded for a sample, the sample may be in any form which is compatible with the particular type of spectroscopy, and therefore may be, as appropriate, homogeneous or heterogeneous, comprising one or a combination of, for example, a gas, a liquid, a liquid crystal, a gel, and a solid.

Samples that originate from an organism (e.g., subject, patient) may be in vivo; that is, not removed from or separated from the organism. Thus, in one embodiment, said sample is an in vivo sample. For example, the sample may be circulating blood, which is "probed" in situ, in vivo, for example, using NMR methods.

Samples that originate from an organism may be ex vivo; that is, removed from or separated from the organism. Thus, in one embodiment, said sample is an ex vivo sample (e.g., an ex vivo blood or blood-derived sample, an ex vivo blood sample, an ex vivo serum sample; ex vivo plasma sample, an ex vivo urine sample).

In one embodiment, the sample is removed from or separated from the organism, and is not returned to the organism (e.g., an ex vivo blood sample).

In one embodiment, the sample is removed from or separated from the organism, and is returned to the organism (i.e., "in transit") (e.g., as with dialysis methods) (e.g., an ex vivo in transit sample).

Examples of samples include:

a whole organism (living or dead, e.g., a living human);

a part or parts of an organism (e.g., a tissue sample, an organ);

a pathological tissue such as a tumour;

a tissue homogenate (e.g., a liver microsome fraction);

an extract prepared from an organism or a part of an organism (e.g., a tissue sample extract, such as a perchloric acid extract);

an in vitro tissue, such as a spheroid;

a suspension of a particular cell type (e.g., hepatocytes);

an excretion, secretion, or emission from an organism (especially a fluid); material which is administered and collected (e.g., dialysis fluid);

material which develops as a function of pathology (e.g., a cyst, a blister);

supernatant from a cell culture.

Examples of fluid samples include, for example, blood plasma, blood serum, whole blood, urine, (gall bladder) bile, cerebrospinal fluid, milk, saliva, mucus, nasal fluids, sweat, gastric juice, pancreatic juice, seminal fluid, prostatic fluid, seminal vesicle fluid, seminal plasma, amniotic fluid, foetal fluid, follicular fluid, synovial fluid, aqueous humour, ascite fluid, cystic fluid, blister fluid, and cell suspensions; and extracts thereof.

Examples of tissue samples include liver, kidney, prostate, brain, gut, blood, blood cells, skeletal muscle, heart muscle, lymphoid, bone, cartilage, and reproductive tissues.

Organisms, Subjects, Patients

As discussed above, in many cases, samples are, or originate from, or are drawn or derived from, an organism (e.g., subject, patient). In such cases, the organism may be as defined below.

In one embodiment, the organism (e.g., subject, patient) is an animal.

In one embodiment, the organism (e.g., subject, patient) is a mammal.

In one embodiment, the organism (e.g., subject, patient) is a placental mammal, a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the organism (e.g., subject, patient) may be any of its forms of development, for example, a foetus.

In one embodiment, the organism (e.g., subject, patient) is a human.

The subject (e.g., a human) may be characterised by one or more criteria, for example, sex, age (e.g., 40 years or more, etc.), ethnicity, medical history, lifestyle (e.g., smoker, non-smoker), hormonal status (e.g., pre-menopausal, post-menopausal), etc.

The term "population," as used herein, refers to a group of organisms (e.g., subjects, patients). If desired, a population (e.g., of humans) may be selected according to one or more of the criteria listed above.

Integrated Metabonomics

As described herein, the methods of the present invention may employ spectral data, i.e., spectroscopic data (e.g., NMR data, UV absorption data, IR absorption data) (e.g., an NMR spectrum, a UV absorption spectrum, an IR absorption spectrum) or spectrometric data (e.g., mass spectrum data) (e.g., a mass spectrum) and/or non-spectral data (e.g., metabonomic, proteomic, transcriptomic, and/or genomic data).

The methods may also employ composite data or composite data sets.

The terms "composite data" and "composite data set," as used herein, pertain to data that comprises spectral data (e.g., NMR spectral data, e.g., an NMR spectrum; e.g., mass spectral data, e.g., a mass spectrum) and/or non-spectral data (e.g., metabonomic, proteomic, transcriptomic, and/or genomic data) as well as at least one additional datum or data vector.

The additional datum or data vector may be spectral or non-spectral. Spectral data may include, for example, numerical representations of images, etc.

The additional datum or data vector may be, for example: obtained for the same sample using a different analysis or spectroscopic technique; obtained for another sample, of the same sample type (e.g., blood, urine, tissue, tissue extract), but obtained from the subject at a different time-point; obtained for another sample of different sample type (e.g., blood, urine, tissue, tissue extract) for the same subject; and the like, and combinations thereof.

Examples of non-spectral data include, e.g., one or more clinical parameters. Clinical parameters which are suitable for use in composite methods include, but are not limited to, the following: (a) established clinical parameters routinely measured in hospital clinical labs, such as: age; sex; body mass index; height; weight; family history; medication history; cigarette smoking; alcohol intake; blood pressure; full blood cell count (FBCs); red blood cells; white blood cells; monocytes; lymphocytes; neutrophils; eosinophils; basophils; platelets; haematocrit; haemoglobin; mean corpuscular volume and related haemodilution indicators; fibrinogen; functional clotting parameters (thromboplastin and partial thromboplastin); electrolytes (sodium, potassium, calcium, phosphate); urea; creatinine; total protein; albumin; globulin; bilirubin; protein markers of liver function (alanine aminotransferase, alkaline phosphatase, gamma glutamyl transferase); glucose; Hba1c (a measure of glucose-Haemoglobin conjugates used to monitor diabetes); lipoprotein profile; total cholesterol; LDL; HDL; triglycerides; blood group; and (b) established research parameters routinely measured in research laboratories but not usually measured in hospitals, such as: hormonal status; testosterone; estrogen; progesterone; follicle stimulating hormone; inhibin; transforming growth factor-beta1; Transforming growth factor-beta2; chemokines; MCP-1; eotaxin; plasminogen activator inhibitor-1; cystatin C.

Implementation

The methods of the present invention, or parts thereof, may be conveniently performed electronically, for example, using a suitably programmed computer system.

One aspect of the present invention pertains to a computer system or device, such as a computer or linked computers, operatively configured to implement a method of the present invention, as described herein.

One aspect of the present invention pertains to computer code suitable for implementing a method of the present invention, as described herein, on a suitable computer system.

One aspect of the present invention pertains to a computer program comprising computer program means adapted to perform a method according to the present invention, as described herein, when said program is run on a computer.

One aspect of the present invention pertains to a computer program, as described above, embodied on a computer readable medium.

One aspect of the present invention pertains to a data carrier which carries computer code suitable for implementing a method of the present invention, as described herein, on a suitable computer.

Computers may be linked, for example, internally (e.g., on the same circuit board, on different circuit boards which are part of the same unit), by cabling (e.g., networking, ethernet, internet), using wireless technology (e.g., radio, microwave, satellite link, cell-phone), etc., or by a combination thereof.

Examples of data carriers and computer readable media include chip media (e.g., ROM, RAM, flash memory (e.g., Memory Stick™, Compact Flash™, Smartmedia™), magnetic disk media (e.g., floppy disks, hard drives), optical disk media (e.g., compact disks (CDs), digital versatile disks (DVDs), magneto-optical (MO) disks), and magnetic tape media.

One aspect of the present invention pertains to a system (e.g., an "integrated analyser", "diagnostic apparatus") comprising:
 (a) a first component comprising a device for obtaining spectral data (e.g., a NMR spectrometer, a mass spectrometer, etc.) for a sample; and,
 (b) a second component comprising computer system or device, such as a computer or linked computers, operatively configured to implement a method of the present invention, as described herein, and operatively linked to said first component.

In one embodiment, the first and second components are in close proximity, e.g., so as to form a single console, unit, system, etc. In one embodiment, the first and second components are remote (e.g., in separate rooms, in separate buildings).

Biomarkers and their Use

One aspect of the present invention pertains to a (novel) discriminant chemical species (e.g., biomarker), for a predetermined condition, identified by a method as described herein.

One aspect of the present invention pertains to a discriminant chemical species (e.g., biomarker), or a combination of a plurality of diagnostic species, for a predetermined condition, identified by a method as described herein, for use in a method of classification (e.g., a method of diagnosis, prognosis, etc.).

One aspect of the present invention pertains to a method of classification (e.g., a method of diagnosis, prognosis, etc.) which relies upon (or employs) a discriminant chemical species (e.g., biomarker), or a combination of a plurality of discriminant chemical species, for a predetermined condition, identified by a method as described herein.

One aspect of the present invention pertains to use of a discriminant chemical species (e.g., biomarker), or a combination of a plurality of discriminant chemical species, for a predetermined condition, identified by a method as described herein, in a method of classification (e.g., a method of diagnosis, prognosis, etc.).

One aspect of the present invention pertains to an assay for use in a method of classification (e.g., a method of diagnosis, prognosis, etc.), which assay relies upon a discriminant chemical species (e.g., biomarker), or a combination of a plurality of discriminant chemical species, for a predetermined condition, identified by a method as described herein.

One aspect of the present invention pertains to use of an assay in a method of classification (e.g., a method of diagnosis, prognosis, etc.), which assay relies upon a discriminant chemical species (e.g., biomarker), or a combination of a plurality of discriminant chemical species, for a predetermined condition, identified by a method as described herein.

Applications of Biomarkers

The methods described herein provide powerful means for the identification of biomarkers which can be used, for example, in the diagnosis and prognosis of disease, for assisting medical practitioners in providing optimum therapy for disease. Examples of these and other applications of biomarkers include, but are not limited to, the following:

Medical Diagnostic Applications (a) Early detection of abnormality/problem. For example, the technique can be used to identify a clinically silent disease prior to the onset of clinical symptoms.

(b) Diagnosis (identification of disease), especially cheap, rapid, and non-invasive diagnosis.

(c) Differential diagnosis, e.g., classification of disease, severity of disease, etc.

Medical Prognosis Applications (a) Prognosis (prediction of future outcome), including, for example, analysis of "old" samples to effect retrospective prognosis.

(b) Risk assessment, to identify subjects at risk of suffering from a particular indication. The methods described herein can be used for population screening (as for diagnosis) but in this case to screen for the risk of developing a particular disease. Such an approach will be useful where an effective prophylaxis is known but must be applied prior to the development of the disease in order to be effective.

(c) Antenatal screening for a wide range of disease susceptibilities. The methods described herein can be used to analyse blood or tissue drawn from a pre-term fetus (e.g., during chorionic vilus sampling or amniocentesis) for the purposes of antenatal screening.

Aids to Therapeutic Intervention (a) Therapeutic monitoring, e.g., to monitor the progress of treatment. For example, by making serial diagnostic tests, it will be possible to determine whether and to what extent the subject is returning to normal following initiation of a therapeutic regimen.

(b) Patient compliance, e.g., monitoring patient compliance with therapy.

(c) The methods described herein can be used for "pharmacometabonomics," in analogy to pharmacogenomics, e.g., subjects could be divided into "responders" and "non-responders" using the metabonomic profile as evidence of "response," and features of the metabonomic profile could then be used to target future patients who would likely respond to a particular therapeutic course.

Tools for Drug Development (a) Clinical evaluations of drug therapy and efficacy. As for therapeutic monitoring, the methods described herein can be used as one end-point in clinical trials for efficacy of new therapies. The extent to which sequential diagnostic fingerprints move towards normal can be used as one measure of the efficacy of the candidate therapy.

(b) Detection of toxic side-effects of drugs and model compounds (e.g., in the drug development process and in clinical trials).

(c) Improvement in the quality control of transgenic animal models of disease; aiding the design of transgenic models of disease.

The methods described herein may be used as an alternative or adjunct to other methods, e.g., the various genomic, pharmacogenomic, and proteomic methods.

EXAMPLES

The following are examples are provided solely to illustrate the present invention and are not intended to limit the scope of the present invention, as described herein.

Study 1

In order to illustrate the applicability of the methods described herein, they have been applied to 1H NMR spectra of urine from a metabonomic study of a model of insulin resistance (taken from-the Biological Atlas of Insulin Resistance (BAIR, Wellcome Trust Grant 066786) project) based on the administration of a carbohydrate diet to three different mice strains (C57BU6Oxjr, BALB/cOxjr, and 129S6/SvEvOxjr). A series of metabolites of biological importance can be conclusively assigned and identified by use of the STOCSY approach. The applicability of the methods in a functional genomic context, for the definition of strain-specific metabolic phenotype characteristics in mice, is also demonstrated.

Animal and Samples

A panel of three inbred adult male mouse strains, namely C57BU6Oxjr, BALB/cOxjr, and 129S6/SvEvOxjr, was used in this study. All mice had free access to water and standard laboratory chow pellets (ERB, Whitam, U.K.) and were maintained on a 12-h light/dark cycle. Experiments were conducted under a U.K. Home Office License approval and according to the rules of animal use in scientific experiments in the U.K. Urine samples were collected from mice maintained for 12 h (8 p.m.-8 a.m.) in metabolic cages. Samples were collected into vials containing a 1% sodium azide solution to minimize microbiological contamination, centrifuged for solid particle removal, and stored at −80° C. until NMR acquisition.

NMR Spectroscopy

An aliquot (200 μL) of each urine sample was added to 200 μL of 0.2 M sodium phosphate buffer (pH 7.4) containing 1 mMTSP (sodium trimethylsilyl [2,3,3,3-$^2$H$_4$]propionate) and 20% D$_2$O as a chemical shift reference standard and lock signal, respectively, and 200 μL of water (MilliQ quality). All samples were centrifuged at 3000 rpm for 10 minutes to remove any solid debris. $^1$H NMR spectra were measured at 600 MHz and 300 K using a flow injection system (Bruker Biospin, Karlsruhe, Germany). The water resonance was suppressed by using a 90°-3 μs-90°-100 ms-90° pulse sequence with irradiation during a 2-s relaxation delay and also during the 100-ms mixing time. For each sample 64 transients were collected into 32,768 data points using a spectral width of 20.036 ppm. The total acquisition time was around 4 minutes per sample. Prior to Fourier transformation, an exponential line-broadening factor of 1 Hz was applied to each free induction decay. A spin-lock of 100 μs was used for the TOCSY experiment (total correlation spectroscopy) (see, e.g., Braunschweiler, L.; Ernst, R. R., *J. Magn. Reson.*, 1983, 53, 521-528). The spectra were phased, baseline-corrected, and referenced to TSP (δ 0.0) automatically using an in-house routine written in MATLAB (Mathworks, Natick, Mass.). (See, e.g., Ebbels, T. M. D.; Lindon, J. C.; Nicholson, J. K.; Holmes, E., US Patent Publication No US 2001-0029380, published 2001-12-20.) The regions δ 4.6-5 and δ 5.5-6.2 were removed to eliminate baseline effects of imperfect water saturation and the non-quantitative contribution of urea, respectively.

Computer and Software

NMR processing and pattern recognition were carried out using a Power Mac G5 with dual 64-bit 2-GHz processors and 2 GB of synchronous dynamic random access memory (SDRAM). NMR processing and pattern recognition routines were written in-house in the MATLAB 6.5 environment (Mathworks, Natick, Mass.).

$^1$H NMR Spectra

A total of 612 $^1$H NMR spectra of urine samples, corresponding to the different mouse strains (216 from BALB/c, 263 from C57BU6, and 133 from 129S6 strains), were acquired and processed. The principal components analysis (PCA) of the 1H NMR spectra data set in combination with the $F_{calc}$ plot allowed us to highlight 13 outliers in the set of 612 $^1$H NMR spectra. (See, e.g., Beebe, K. B.; Pell, R. J.; Seasholtz, M. B., *Chemometrics: A Practical Guide*, John Wiley & Sons: New York, 1998.) For all of these spectra, the reason for their isolation from the main body of samples was due to either bad water resonance suppression or a very dilute sample, providing a very low signal-to-noise ratio. These outliers were, therefore, removed from the data set for the rest of the study.

In contrast with many previous $^1$H NMR based metabonomic studies using reduced data (see, e.g., Lindon, J. C.; Holmes, E.; Nicholson, J. K., *Anal. Chem.*, 2003, 75, 384A-391 A), the methods described herein used the full resolution of the 600-MHz $^1$H NMR spectra to extract the biological information related to the differences in the metabolism of different mouse strains.

Examples of $^1$H NMR spectra of urine corresponding to the three different mouse strains are presented in FIG. 1. Many metabolites can already be recognized in these spectra, and a difference in patterns among these three spectra can readily be observed. However, this may be due to variation not related to the strain discrimination (variance between groups) but instead may be due to variation within the strain (variance within groups), and obviously the comparison of only three samples cannot be conclusive.

Statistical Total Correlation Spectroscopy

All 612 urine NMR spectra from all the mouse strain samples were used for the computation of the correlation matrix. The result is shown in FIG. 2 as a contour plot indicating the highest correlation.

The contour plot can be interpreted in the same manner as two-dimensional NMR maps. For instance, in the region between δ 1.5 and δ 4.2, it is possible to recognize the spin structure of valeramide and glucose (for these compounds and all other direct assignments described herein, the chemical shift and the multiplicity of molecules have been compared with $^1$H NMR spectra of water solution of the pure compound). Just as with 2D correlation spectroscopy plots, each peak in the NMR data set will appear on the diagonal of the correlation matrix. Each data point has an autocorrelation value of 1 and a very high correlation with the other data points from the same peak; for this reason the peaks on the diagonal are visible and other peaks with data points having a significant correlation with the diagonal peak will appear at the appropriate chemical shift, that is, off the diagonal. Simply reading the two chemical shifts of an off-diagonal peak then allows the determination of the chemical shifts of the two correlated peaks. If more than two such peaks are inter-correlated, then it is possible to identify a network of correlated peak intensities.

Figure 2:
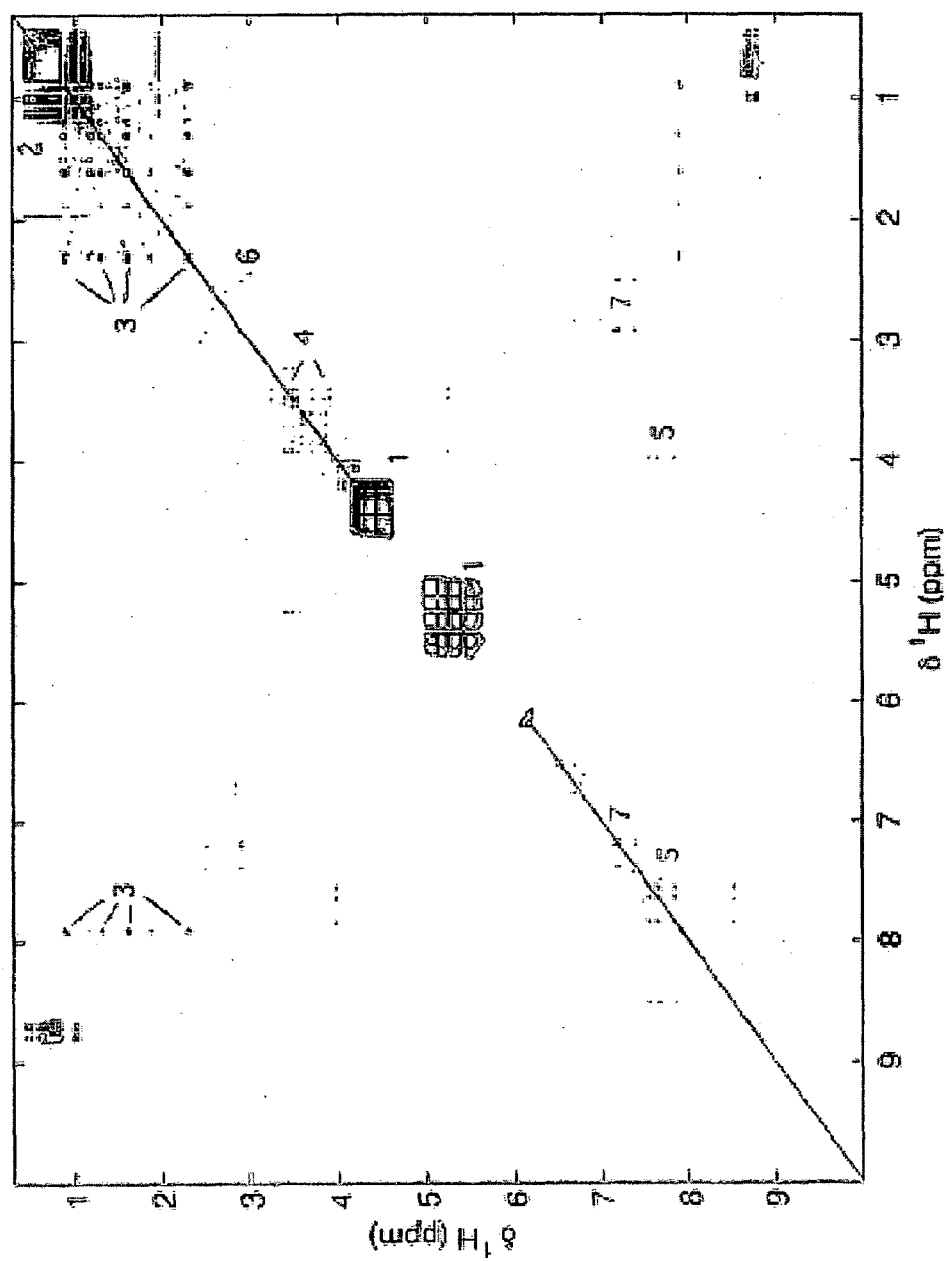
FIG. 2 is a STOCSY two-dimensional representation of $^1$H NMR spectra for three different mouse strains (BALB/c, C57BL/6, and showing δ/δ $^1$H connectivities): (1) water signal suppression imperfection; (2) protein; (3) valeramide; (4) glucose; (5) hippurate; (6) 2-oxoglutarate; (7) 3-hydroxyphenylpropionate. See Study 1 below.
Figure 3:
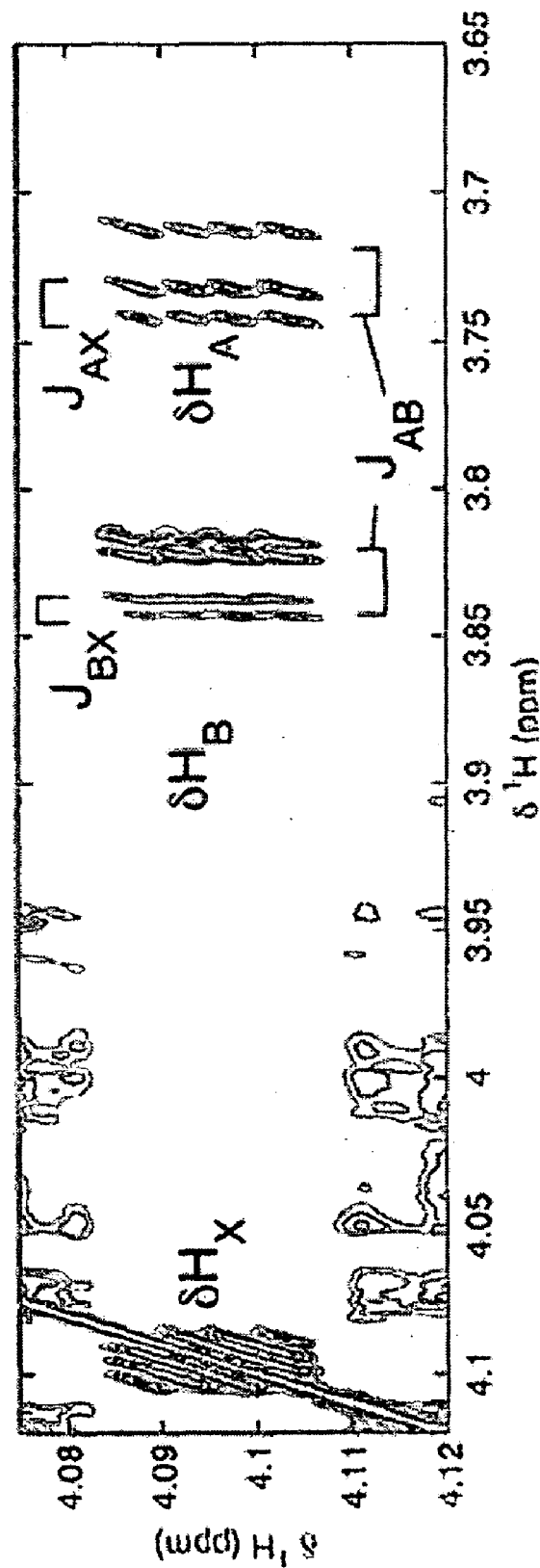
FIG. 3 is a STOCSY two-dimensional representation of $^1$H NMR spectra for three different mouse strains (BALB/c, C57BL/6, and 129S6) for the glycerate spin system ABX δH$_X$, δH$_B$, and δH$_A$ indicate chemical shifts of three protons and J$_{AB}$, J$_{AX}$, and J$_{BX}$ indicate the $^1$H-$^1$H coupling patterns. See Study 1 below.

Several other correlated peaks are also present on the large-scale representation shown in FIG. 2, and an expansion to give the small region shown in FIG. 3 reveals the structure of the glycerate ABX system with a high digital resolution such that it is possible to measure the different coupling constants ($^2J_{AB}$) 11.4 Hz, $^3J_{AX}$) 5.7 Hz, and $^3J_{BX}$) 3.0 Hz).

However, the spin system of a molecule can overlap with other spin systems, and this reduces the correlation that exists for the resonances of both molecules. For this reason, only three out of four peaks of $\delta H_A$ are present in the shown figure.

Figure 4:
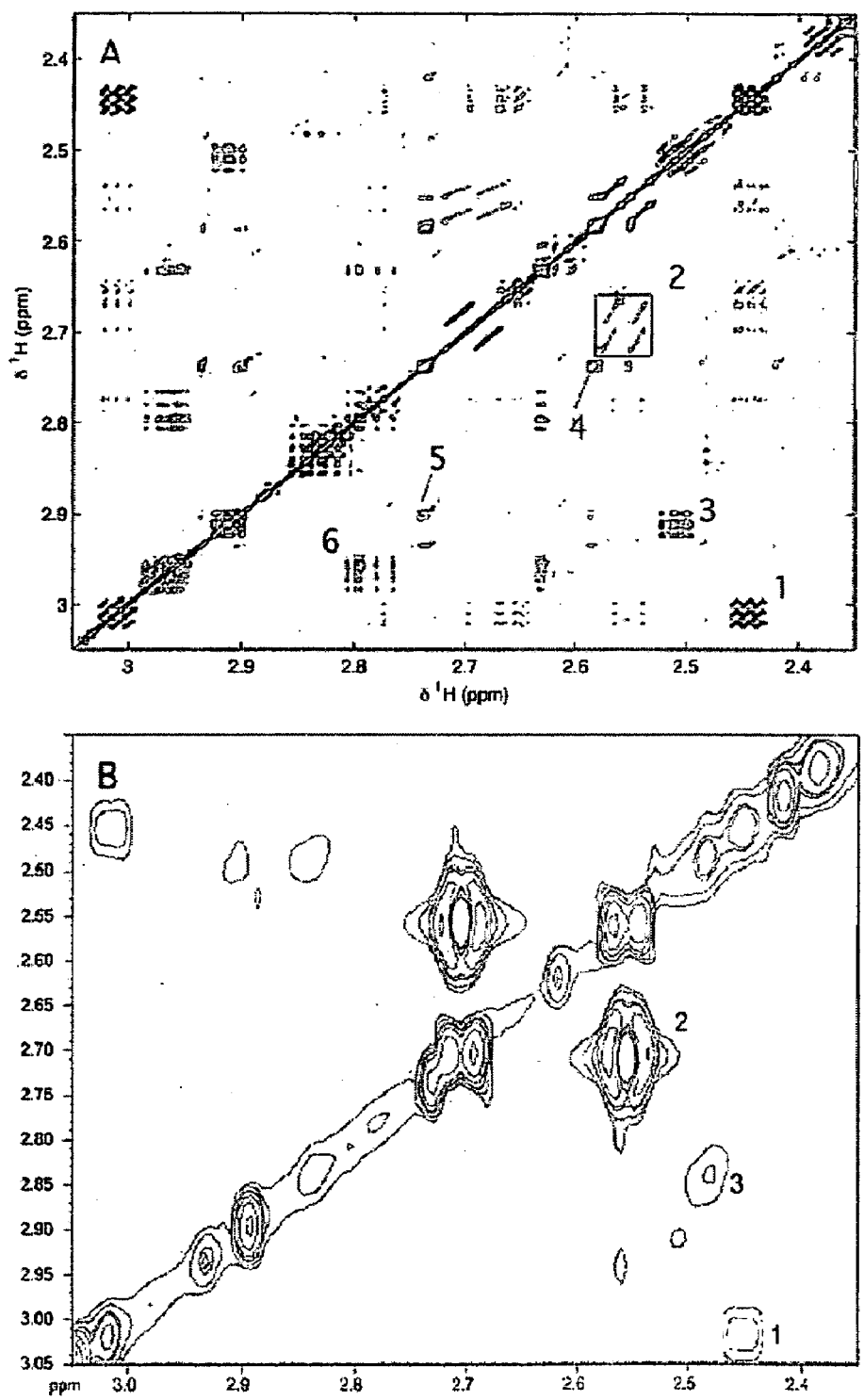
FIG. 4 is (A) a localized two-dimensional representation of STOCSY of $^1$H NMR spectra for three different mouse strains (BALB/c, C57BL/6, and 129S6); and (B) an example of a TOCSY NMR spectrum obtained from a single urine sample of a 129S6 strain mice for the same chemical shift region. Key: (1) 2-oxoglutarate; (2) citrate; (3) 3-hydroxyphenylpropionate; (4) methylamine and dimethylamine correlation; (5) dimethylamine and trimethylamine correlation. See Study 1 below.

In the region between $\delta$ 2.2 and 3.2, many resonances can be assigned easily with the correlation method (see FIG. 4). For example, the two correlated triplets at $\delta$ 2.45 and 3.01 with the coupling constant $^3J_{AX}$) 7.2 Hz are attributed to 2-oxoglutarate. The AB spin system of citrate can also be recognized, but the correlation is weakened by the peak position variation due to physicochemical differences (pH and metal ion concentration) across samples, which particularly affects citrate. This produces correlated lines instead of spots for the cross-peaks and diagonal peaks with STOCSY (see FIG. 4). Therefore, in the case of citrate, the cross-peaks are not parallel to the diagonal peaks, which indicates that the coupling constant of both AB spin systems varies with the differences of physicochemical environment across the samples.

An AX spin system of two triplets can be noticed at $\delta$ 2.91 and 2.51 with a coupling constant $^3J_{AX}$) 7.7 Hz. This spin system is strongly correlated to others resonances in the aromatic region of the spectrum. It is difficult to display the correlation between two distant resonances because the resulting peaks are too narrow relative to the large frequency difference between the peaks.

However, there is a way to approach this problem as follows. Computing only the correlation between one of the data points ($\delta$ 2.512) representing the maximum of one of the triplets and all the other variables yields one vector, which has the size of the number of variables used. Then, by selecting the spectrum with the maximum value of this selected variable (i.e., the spectrum for which the peak at $\delta$ 2.512 is greatest), it is possible to plot that spectrum with a color code corresponding to the correlation between the selected resonance and all the other points of the spectra.

Figure 5:
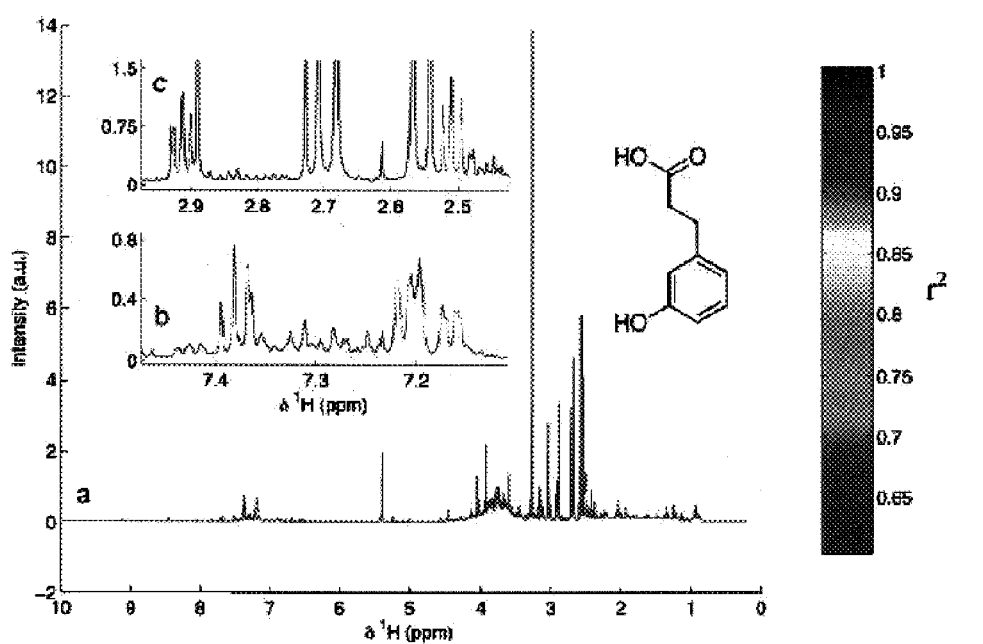
FIG. 5 is a one-dimensional STOCSY representation for the selected variable corresponding to δ 2.512. The degree of correlation across the spectrum has been (color) coded and projected on the spectrum that has the maximum for this variable. (a) Full spectrum; (b) same spectrum between δ 7.1 and 7.5; (c) same spectrum between δ 2.4 and 3. Several of the peaks (e.g., near δ 2.5, 2.9, 7.2, and 7.4) are predominantly red. See Study 1 below. See also: Cloarec et al., *Anal. Chem.*, 2005, Vol. 77, pp. 1282-1289.

A typical result is shown in FIG. 5. This approach highlights all those correlated metabolite resonances that are not strongly overlapping with resonances from other molecules. Here the potential of the approach can be seen since correlations can be observed between resonances with no NMR-based spin-coupling connectivity. Thus, in the aromatic region, it is possible to recognize the resonances of a meta-substituted benzene ring (one triplet, two doublets, and one singlet). One of the triplet peaks is overlapped with a singlet from another molecule; however, the remaining correlation (plotted in light blue) is enough to reveal its position. Thus this molecule can be identified as a derivative of a meta-substituted phenylpropanoic acid and is probably 3-hydroxyphenylpropionic acid. (See, e.g., Stanley, E. G., Ph.D., University of London, London, 2002.)

Furthermore, FIG. 4 (panel A) shows a correlation between methylamine and dimethylamine. The origin of this cross-peak is obviously not from a correlation between two parts of the same molecule but is from the fact that the concentrations of these two molecules are highly correlated, in that they vary in the same way because they are involved in the same pathways. This means that STOCSY is not only able to reveal the whole NMR peak set of single metabolites, but is also able to highlight molecules that are involved in related pathways.

Finally, although the context of these two representations is different, by comparing the STOCSY plot (FIG. 4, panel A) with a TOCSY spectrum of a single sample (FIG. 4, panel B), it is clear that the resolution of the STOCSY spectrum is much higher than that of a TOCSY spectrum. This phenomenon derives from the fact that the information provided by STOCSY is related to the whole sample set and not only to one sample. However, STOCSY is well suited to a large number of samples and the two-dimensional NMR experiments (TOCSY, COSY, JRES, . . . ) remain the best choice in the case of individual samples.

Pattern Recognition

The data analysis process next employed a supervised pattern recognition procedure in order to reveal the specific variation of the urine composition according to the mouse strain.

Data analysis was carried out in two steps with all the variables mean centered and autoscaled by dividing each variable by its standard deviation. In the first stage a principal components analysis (PCA) was conducted in order to select out the distinct outliers by comparing the spectral residuals from sample to sample using the method of the $F_{calc}$ plot (see, e.g., Beebe, K. B.; Pell, R. J.; Seasholtz, M. B., *Chemometrics: A Practical Guide*, John Wiley & Sons: New York, 1998). The selected spectra are then checked and rejected only if they showed inconsistency related to a baseline problem, bad phasing, or a very low signal-to-noise ratio.

The second stage is a supervised pattern recognition method called orthogonal projection on latent structure (O-PLS), which was developed by Trygg et al. (See, e.g., Trygg, J.; Wold, S. *J., Chemom.*, 2002, 16, 119-128; Trygg, J. J., *Chemom.*, 2002, 16, 283-293; Trygg, J.; Wold, S., *J. Chemom.*, 2003, 17, 53-64.) An O-PLS model can be seen as a factor analysis model, where the variation in the matrix X (the NMR spectra) and the matrix Y (the descriptive variables) is separated into three parts. The first part contains the variation common in X and Y, the second one contains the specific variation for X, so-called structured noise, and the last one contains the residual variance. The O-PLS method provides a prediction similar to that of PLS (projection on latent structure). However, the interpretation of the models is improved because the structured noise is modeled separately from the variation common in X and Y. Therefore, the O-PLS loading and regression coefficients provide more straightforward and accurate interpretation than PLS, which models the structured noise together with the correlated variation between X and Y. Furthermore, the orthogonal loading matrices provide the opportunity to interpret the structured noise. To test the validity of the model against overfitting, the cross-validation parameter $Q^2$ was computed. (See, e.g., Trygg, J.; Wold, S., *J. Chemom.*, 2003, 17, 53-64.) In the present example, each line of the X matrix is an NMR spectrum corresponding to one sample and each column of Y defines a class (or group) whose values are dummy variables as used in discriminant analysis. The method can therefore be defined as O-PLS-DA.

To improve the interpretability of the O-PLS model, the method described by Cloarec et al. has also been applied. (See, e.g., Cloarec, O.; Dumas, M. -E.; Trygg, J.; Craig, A.; Barton, R. H.; Lindon, J. C.; Nicholson, J. K.; Holmes, E., submitted for publication in *Anal. Chem. Analytical Chemistry A*.) It consists of combining the back-scaled O-PLS-DA coefficients from an autoscaled model with the variable weight of the same model in the same plot. For this purpose, each O-PLS coefficient is first multiplied by the standard deviation of its corresponding variable and then plotted as a function of its related chemical shift but with a color code linked to the weight of the variable in the model, highlighting in this way the resonances of the most important metabolites involved in the discrimination among the different groups (classes). This tool can also be applied to direct structural identification of biomarkers.

Furthermore, the result of STOCSY can also been combined with pattern recognition results in one plot. From the O-PLS coefficients, it is possible to select one significant variable and to re-plot the coefficients as previously, but this time with a color code corresponding to the correlation between the selected variable and other variables, revealing in this way, and according to the level of the correlation, the structural or physiological relationship existing between different resonances. In this way the discriminant resonances between the groups can be highlighted in a first step by the O-PLS-DA, and therefore, due to the intrinsic correlation between resonances from the same molecule, they can be separated to provide easier identification of the discriminant compounds.

Because a supervised data analysis method is used, the quality of the model had to be checked before any further interpretation. The O-PLS model enables very good prediction ability (see Table 1), and two orthogonal-to-Y components were selected on the basis of the cross-validation (maximum $Q^2$).

TABLE 1

O-PLS Model Summary for Discrimination among the $^1$H NMR Spectra of Three Mouse Strains[a]

| Component | $R^2X_{corr}$ | $R^2X_{yo}$ | $R^2X$ | $R^2Y$ | $Q^2$ |
|---|---|---|---|---|---|
| 1-2 | 0.204 | 0 | 0.204 | 0.553 | 0.539 |
| 3 | 0.149 | 0.167 | 0.316 | 0.704 | 0.690 |
| 4 | 0.124 | 0.236 | 0.359 | 0.800 | 0.771 |
| 5 | 0.114 | 0.296 | 0.410 | 0.859 | 0.535 |

[a]$R^2X_{corr}$ is the part of the modeled variance of X correlated to Y, and $R2X_{yo}$ is the part of the modeled variance of X orthogonal to Y.

These orthogonal components model the variations of the NMR spectra not correlated to the difference between the groups, but interfering with the prediction: the structured noise. (See, e.g., Trygg, J.; Wold, S., *J. Chemom.*, 2003, 17, 53-64.) The total explained variation of X for this model is relatively low ($R^2X$) 36%) because many regions of the spectra contained only instrumental noise, and the autoscaling of the corresponding variables contributes to increasing the random variance, which is impossible to model. However, taking into account only the explained variation of X, 33% of the variation of the 1H NMR spectra (X) is linearly correlated to the discrimination between the mouse strains (Y) and 80% of the variation of Y can be related to the variation of X.

Figure 6:
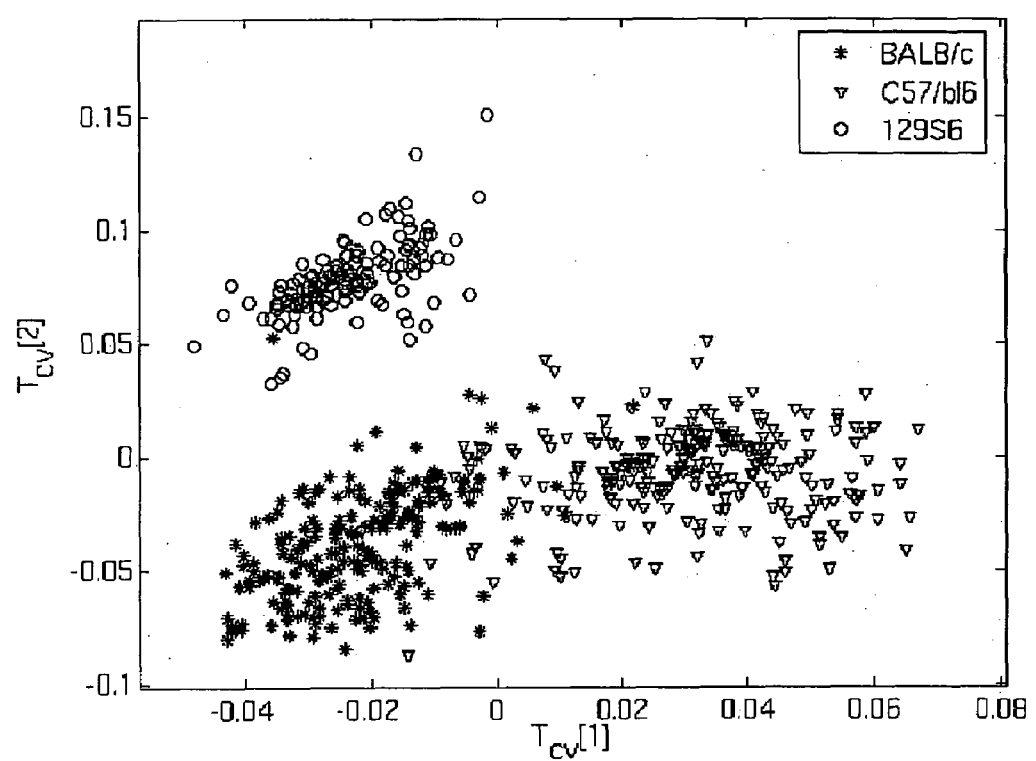
FIG. 6 is a plot of O-PLS cross-validated scores for the discrimination among $^1$H NMR urine spectra of three mouse strains (BALB/c, C57BL/6, and 129S6). See Study 1 below.

Good separation was achieved between the 1H NMR spectra classes corresponding to three mouse strains and is illustrated by the cross-validated score plot (see FIG. 6). The discrimination between the strain 129S6 and the other two strains is clearer than the discrimination between the BALB/c and C57BL/6 strains, in which a slight overlap can be noticed. Moreover, the intragroup variance is larger for the BALB/c and C57BL/6 strains than for the 129S6 strain.

The O-PLS model demonstrates that the discrimination between the urine 1H NMR spectra corresponding to the three mouse strains is clear and makes the interpretation of the O-PLS coefficients possible.

The main purpose of this example is to describe the potential of this methodology and to identify the varying metabolites rather than to focus on all the biological interpretations. For this reason, only the interpretations for the 129S6 strain O-PLS coefficients are discussed herein.

The number of coefficients in the O-PLS model is very large (30 K), but the post-processing step, which combines back-scaled coefficients with the variable weights, allows the selection of the more important peaks for the discrimination.

Figure 7:
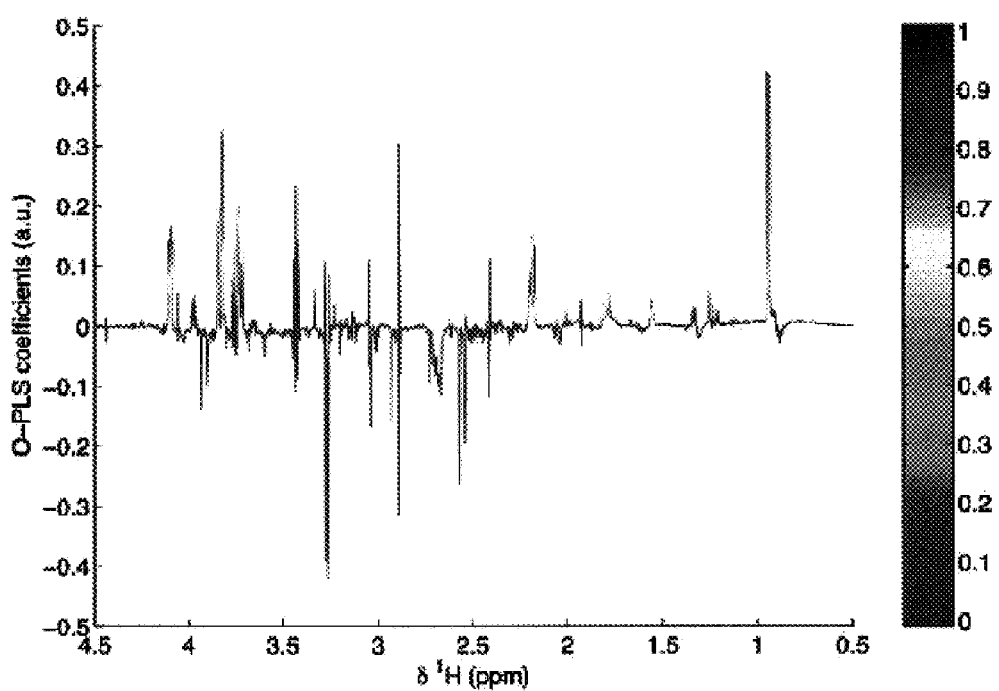
FIG. 7 is an O-PLS regression coefficient plot corresponding to the strain 129S6. The right hand bar corresponds to the weight of the corresponding variable in the discrimination between this strain and the other two strains. Several of the peaks (e.g., near δ 0.9, 1.5, 1.8, 2.2, 3.8, 3.9, and 4.2) are predominantly red. See Study 1 below. See also: Cloarec et al., *Anal. Chem.*, 2005, Vol. 77, pp. 1282-1289.

FIG. 7 shows these coefficients plotted as a function of their corresponding chemical shifts, allowing their interpretation in the same way as a conventional NMR spectrum.

Among all the different peaks, and according to the color coding, different resonances can be selected according to their weight in the discrimination between the strain 129S6 and the other strains (see Table 2).

TABLE 2

List of Resonances with O-PLS Weight >0.4

| δ (ppm) | multiplicity | O-PLS weight | variation | assigned metabolite |
|---|---|---|---|---|
| 0.941 | doublet | 0.84 | ↑ | isovalerate |
| 1.554 | multiplet | 0.87 | ↑ | isovalerate |
| 1.792 | quintuplet | 0.69 | ↑ | glutarate |
| 2.195 | overlapped resonances | 0.84 | ↑ | glutarate and isovalerate |
| 2.930 | singlet | 0.56 | ↓ | dimethylglycine |
| 3.717 | doublet | 0.74 | ↑ | glycerate |
| 3.820 | doublet | 0.95 | ↑ | glycerate |
| 4.095 | doublet of doublets | 0.93 | ↑ | glycerate |

With this list, it is already possible to nominate candidate molecules corresponding to these resonances. For example, the spin system of the glycerate matches very well with the resonances at δ 4.095, 3.820, and 3.717. The assignment is less obvious for the other resonances, particularly for those involved in the overlap at δ 2.195.

The information from the strain-NMR correlation (O-PLS) can be crossed with information from the NMR-NMR correlation (STOCSY) to provide highly interpretable models. From O-PLS coefficients plotted with the post-processing highlighting the more important variables in the discrimination, it is possible to select a resonance of interest and re-plot the same O-PLS coefficients but with a color scheme corresponding to the correlation between the selected resonances and the other resonances of the spectra, as shown previously. This permits rapid visual identification for the experimental spectroscopist.

Figure 8:
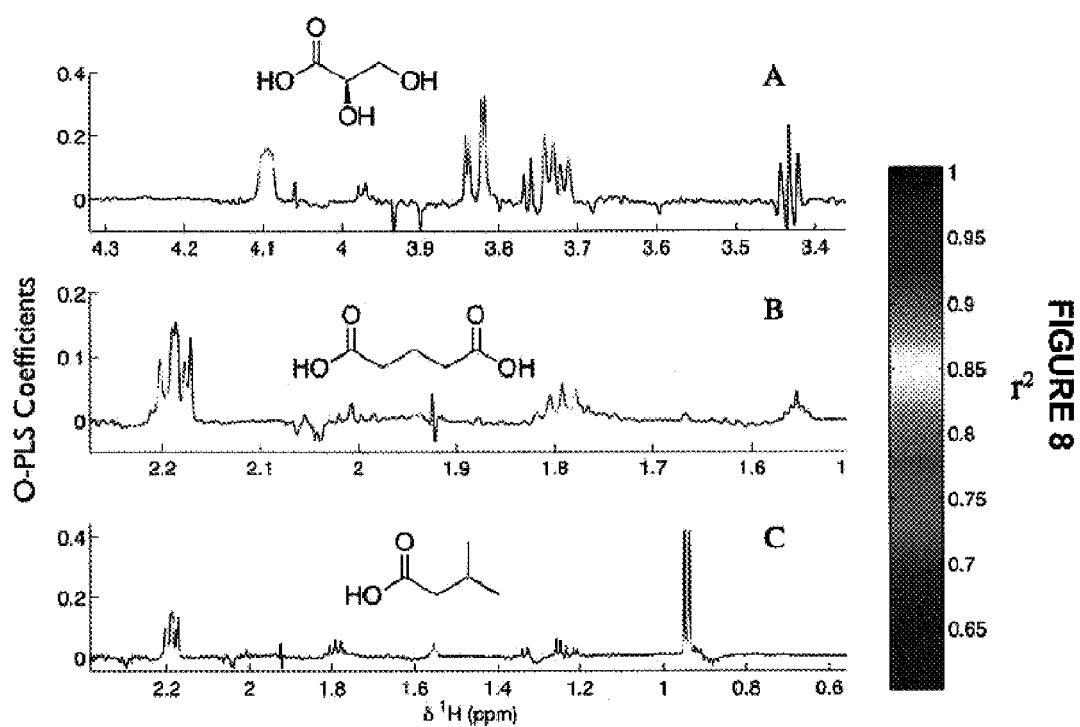
FIG. 8 is a combination of O-PLS coefficients with 1D STOCSY analysis for three exemplar sets of resonances taken from FIG. 7 (maximum intensity correlation of peaks is (color) coded and projected into statistical difference spectra constructed as FIG. 7): (A) δ 3.818, glycerate; (B) δ 1.792, isovalerate; (C) δ 0.947, glutarate. See Study 1 below. See also: Cloarec et al., *Anal. Chem.*, 2005, Vol. 77, pp. 1282-1289.

FIG. 8 presents the O-PLS coefficients of the 129S6 strain displayed with the correlations corresponding to three of the significant resonances ((A) δ 3.818, glycerate; (B) δ 1.792, isovalerate; (C) δ 0.947, glutarate) and reveals very clearly the spin systems of the metabolites. This shows the ability of combining O-PLS pattern recognition with the result of STOCSY in highlighting the metabolites that most vary among the different groups.

This example illustrates the usefulness of the methods described herein, and particularly has demonstrated how methods for analysis of metabonomic data that employ STOCSY can be used to decipher the structure of many metabolites in biofluid samples. Moreover, this example demonstrates that STOCSY, in combination with O-PLS based pattern recognition methods, provides a powerful tool for classification, prediction of sample class based on spectral features, rapid interpretation of metabolic variation, and identification of biomarkers.

Study 2

This study illustrates the use of the methods described herein to identify drug metabolites in urine samples.

Urine samples were collected from two groups of humans; one group had taken paracetamol, and one group had not. $^1$H NMR spectra were recorded for each urine sample. The collection of spectra was treated as a single data set (i.e., a matrix with one row for each $^1$H NMR spectrum, and one column for each $^1$H NMR chemical shift variable). The correlation matrix and the covariance matrix were calculated. The $^1$H NMR spectra showed a strong peak at δ 2.17, which was assigned to the N-acetyl group of paracetamol glucuronide, a well-known metabolite of paracetamol, based on the literature. The correlation between this variable (δ 2.17) and the other variables (i.e., the other chemical shifts) is given in the column of the correlation matrix associated with this variable (i.e., the column for δ 2.17). The covariance between this variable (δ 2.17) and the other variables (i.e., the other chemical shifts) is given in the column of the covariance matrix associated with this variable (i.e., the column for δ 2.17). This covariance (i.e., between δ 2.17 and the other chemical shifts) was plotted as a function of the variable (i.e., chemical shift), and was colour coded according to the correlation. That is, each data point of the covariance plot was plotted in a colour that reflects the correlation of that variable (i.e., chemical shift) with the selected variable (i.e., δ 2.17); specifically, red indicated a correlation of 1 and blue indicated a correlation of 0. This plot (covariance versus chemical shift, with correlation shown in colour) is shown in Panels A, B, and C of FIG. 9. (Each Panel shows a difference range of chemical shift; Panel A shows about δ 6.5 to about δ 8.0; Panel B shows about δ 3.0 to about δ 5.5; Panel C shows about δ 1.6 to about δ 2.6.)

In Panel C, the peak at δ 2.17 is red, as expected, and is auto-correlated with itself. In Panel B, three peaks are red. The first, at about δ 3.7, can be assigned to H2, H3, and H4 of the glucuronide ring. The second, at about δ 3.9, can be assigned to H5 of the glucuronide ring. The third, at about δ 5.1, can be assigned to the anomeric H1 proton of the glucuronide ring. In Panel A, two peaks are red, at about δ 7.2 and δ 7.4, which may be assigned to pairs of aromatic protons.

This approach allows these resonances to be assigned to paracetamol glucuronide, even though there is no conventional NMR connectivity (i.e., via spin-spin coupling) between the various groups. Previously, even several complex 2D NMR experiments (using one sample) would not have been able to show that all these resonances were related. Here, a simple experiment ($^1$H NMR) is used with a number of samples, and the variation between the samples has been exploited in order to extract these connectivities.

Figure 9:
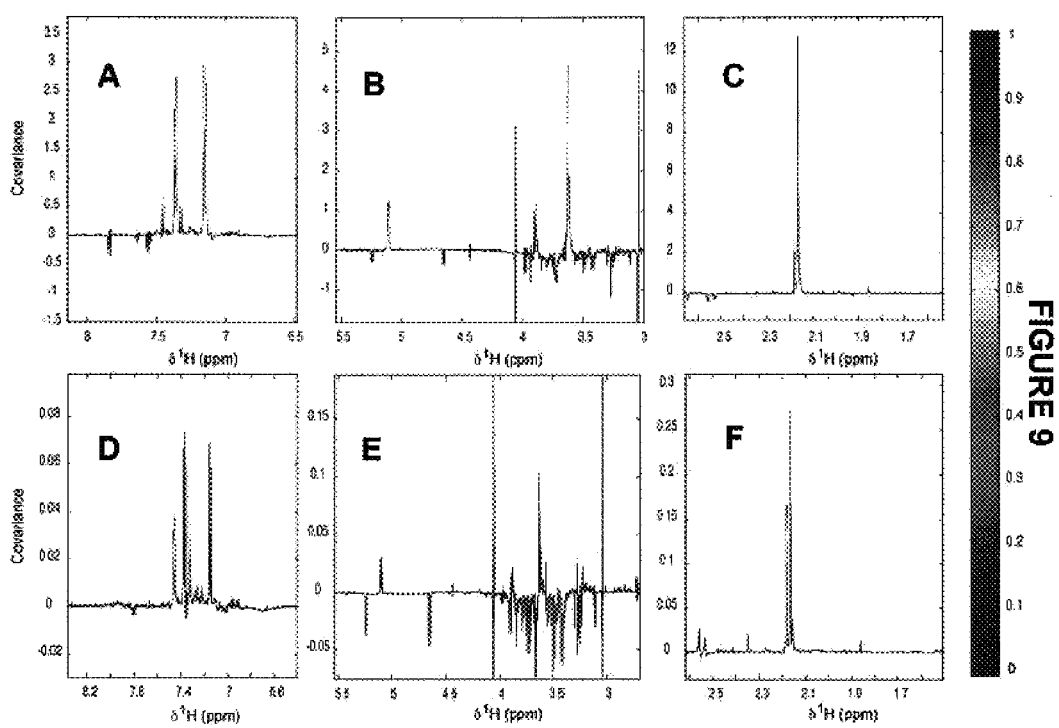
FIG. 9 is a plot of covariance versus $^1$H NMR chemical shift (δ, ppm), colour coded according to correlation, for a study of paracetamol metabolism. Panels A, B, and C show different regions of chemical shift for the same correlation study (paracetamol glucuronide), and Panels D, E, and F show different regions of chemical shift for another correlation study (paracetamol sulfate). See Study 2 below.

Panels C, D, and E of FIG. 9 reflect a similar analysis for another major paracetamol metabolite, the sulfate conjugate, based upon the peak at δ 7.45, assigned to aromatic ring protons. (This resonances was deemed to be the least overlapped of the paracetamol sulfate resonances.) (Each Panel shows a difference range of chemical shift; Panel D shows about δ 6.4 to about δ 8.2; Panel E shows about δ 3.0 to about δ 5.5; Panel F shows about δ 1.6 to about δ 2.6.) A high correlation (>0.75) was found between this resonance and all other resonances for the sulfate conjugate, specifically, the doublet derived from the aromatic proton at δ 7.31 in Panel D, and the singlet arising from the acetyl group at δ 2.18 in Panel F.

In addition, a weak (about 0.3, light blue) negative correlation was found between the resonances for the sulfate conjugate and the resonances for glucose (assignments based on the literature). See especially the peaks at δ 5.2, δ 4.6, and δ 3.25-4 in Panel E. This indicates a biochemical linkage between the levels of the exogenous paracetamol metabolite and the levels of glucose (indicative of endogenous metabolism), that is, a drug-induced interference with energy metabolism.

Study 3

Figure 10:
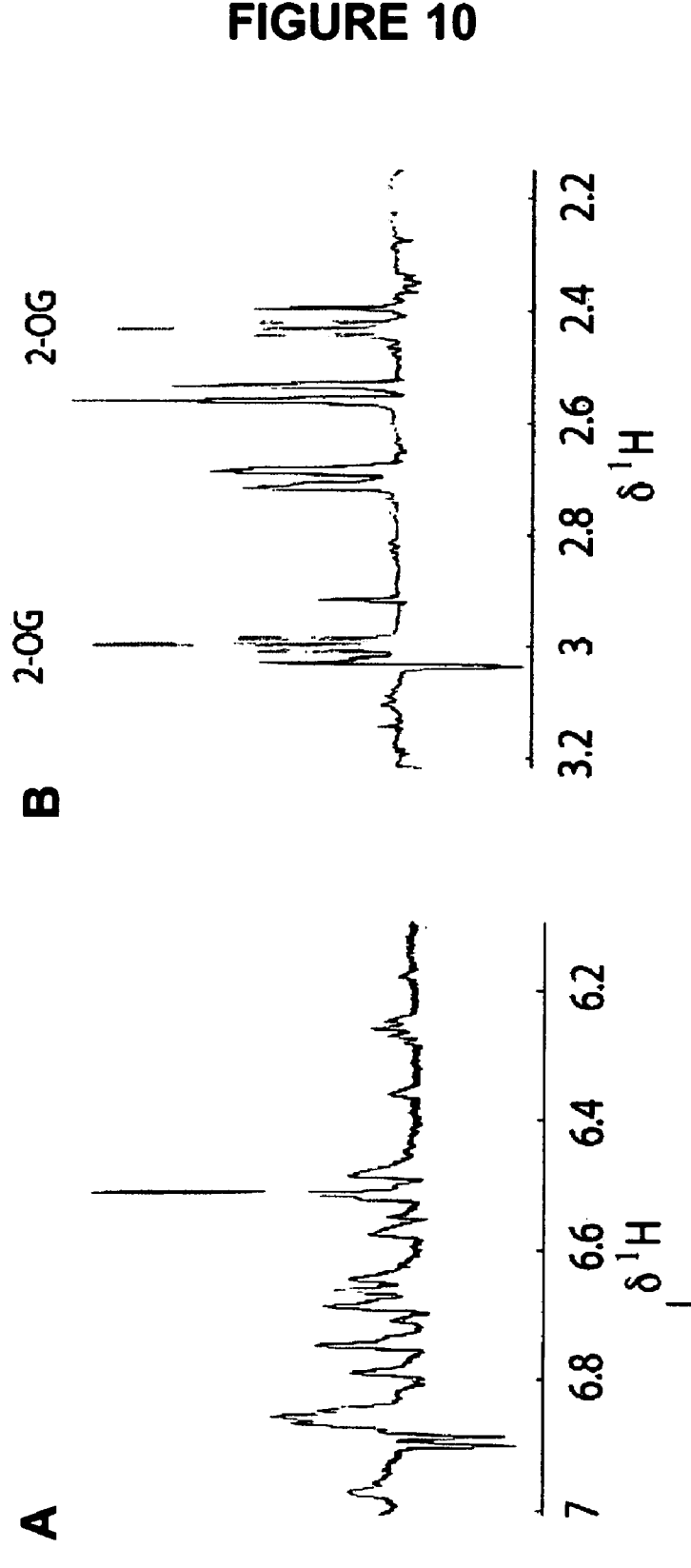
FIG. 10 is a plot of covariance versus $^1$H NMR chemical shift (δ, ppm), colour coded according to correlation with the fumarate resonance at δ 6.54, for a study of mercuric chloride poisoning. Panels A and B show different regions of chemical shift for the same correlation study. See Study 3 below.

A number of rats were dosed with the renal toxin mercuric chloride. A number of urine samples were collected from each rat at different time points after dosing. $^1$H NMR spectra were recorded for each urine sample. The collection of spectra was treated as a single data set (i.e., a matrix with one row for each $^1$H NMR spectrum, and one column for each $^1$H NMR chemical shift variable). The correlation matrix and the covariance matrix were calculated. The $^1$H NMR spectra showed a strong peak at δ 6.54, which was assigned to the olefinic protons of fumarate, a species in the Krebs cycle (the tricarboxylic acid cycle), based on the literature. The correlation between this variable (δ 6.54) and the other variables (i.e., the other chemical shifts) is given in the column of the correlation matrix associated with this variable (i.e., the column for δ 6.54). The covariance between this variable (δ 6.54) and the other variables (i.e., the other chemical shifts) is given in the column of the covariance matrix associated with this variable (i.e., the column for δ 6.54). This covariance (i.e., between δ 6.54 and the other chemical shifts) was plotted as a function of the variable (i.e., chemical shift), and was colour coded according to the correlation. That is, each data point of the covariance plot was plotted in a colour that reflects the correlation of that variable (i.e., chemical shift) with the selected variable (i.e., δ 6.54); specifically, red indicated a correlation of 1 and blue indicated a correlation of 0. This plot (covariance versus chemical shift, with correlation shown in colour) is shown in Panels A and B of FIG. 10. (Each Panel shows a difference range of chemical shift; Panel A shows about δ 6.2 to about δ 7.0; Panel B shows about δ 2.2 to about δ 3.2.)

In Panel A, the peak at δ 6.54 is red, as expected, and is auto-correlated with itself. In Panel B, two triplets are highly correlated with δ 6.54, at about δ 2.42 and about δ 3.00. Both can be assigned to 2-oxo-glutarate (denoted 2-OG in FIG. 10), based on the literature. 2-Oxo-glutarate is also involved in the Krebs cycle.

The concentrations of metabolites linked by a common pathway are expected to show a degree of correlation. For example, in a simple case, if an enzyme is inhibited by a drug, then its substrate level should increase and its product level should decrease if no competing pathways are involved. This study demonstrates that both species, fumarate and 2-oxo-glutarate, are part of a common biochemical pathway (the concentration of one affects and/or is affected by, the concentration of the other), and illustrates the more general principle that the methods described herein may be used to link metabolites that share a common pathway, that is, to reveal connectivity on the basis of a shared pathway, rather than only on the basis of being in the same molecule.

Study 4

Figure 11:
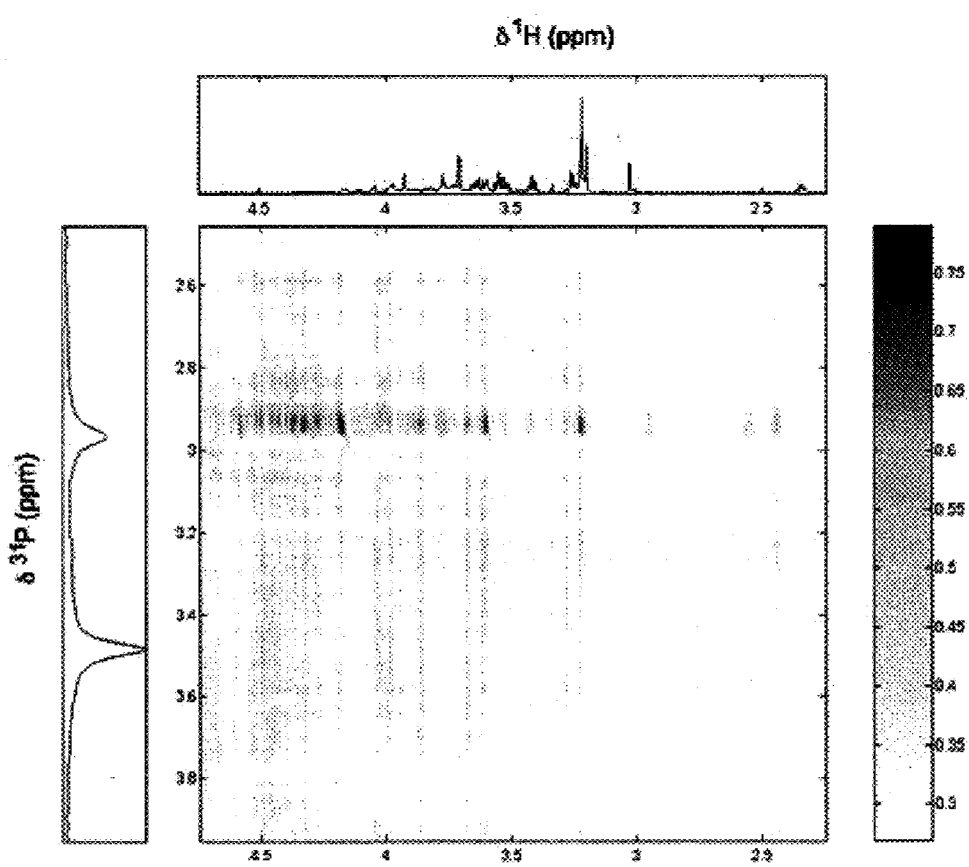
FIG. 11 is a correlation map illustrating the correlation, as indicated by colour (from white to red, for increasing correlation), as a function of both $^{31}$P chemical shift (along the vertical axis) and $^1$H chemical shift (along the horizontal axis), in a study of human gut tissue. The average $^{31}$P NMR spectrum is shown alongside the $^{31}$P δ axis for illustration. Similarly, the average $^1$H NMR spectrum is shown alongside the $^1$H δ axis. See Study 4 below.

Human gut tissue samples were obtained. $^1$H CPMG MAS NMR and $^{31}$P MAS NMR spectra were obtained for each sample. The collection of $^1$H NMR spectra was treated as a first data set (i.e., a matrix with one row for each $^1$H NMR spectrum, and one column for each $^1$H NMR chemical shift variable, n×p) and the collection of $^{31}$P NMR spectra was treated as a second data set (i.e., a matrix with one row for each $^{31}$P NMR spectrum, and one column for each $^{31}$P NMR chemical shift variable, n×q). The correlation matrix and the covariance matrix (each p×q or q×p) were calculated. A correlation map illustrating the correlation matrix is shown in FIG. 11. The correlation is indicated by colour (from white to red, for increasing correlation), as a function of both $^{31}$P chemical shift (from about δ 2.6 to about δ 3.8) and $^1$H chemical shift (from about δ 2.5 to about δ 4.5). The average $^{31}$P NMR spectrum is shown alongside the $^{31}$P δ axis for illustration. Similarly, the average $^1$H NMR spectrum is shown alongside the $^1$H δ axis.

Figure 12:
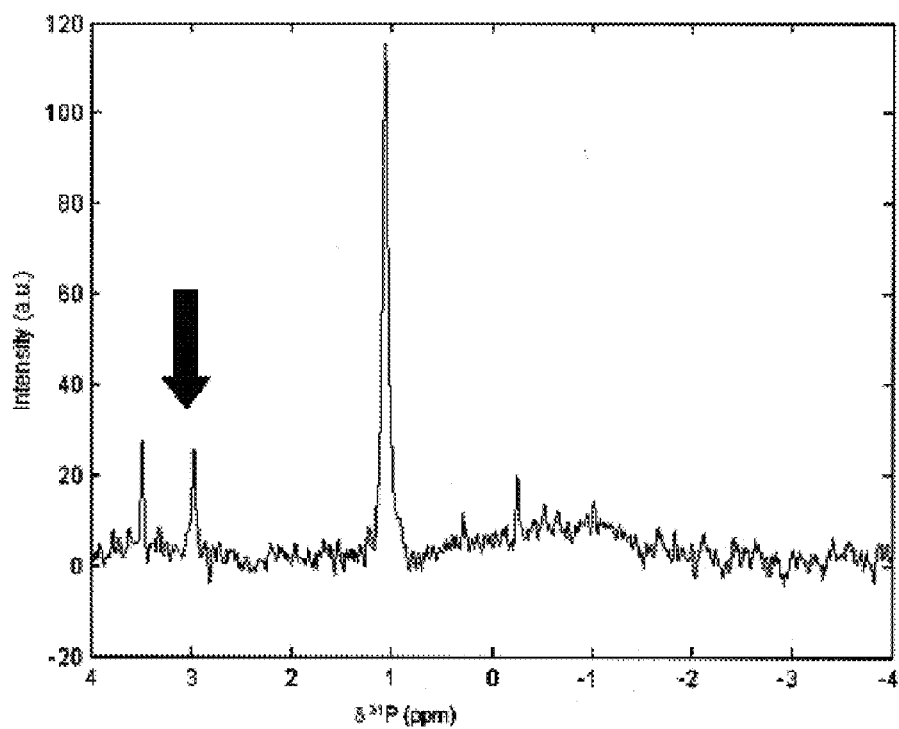
FIG. 12 is a typical $^{31}$P NMR spectrum, in a study of human gut tissue. The solid black arrow indicates the δ 3 resonance that was selected for the correlation study. See Study 5 below.

The $^{31}$P spectra showed two broad resonances at δ 2.5-4. The first, at about δ 3, showed strong correlation with various resonances in the $^1$H spectra, whereas the second, at about δ 3.5, did not. A typical $^{31}$P NMR spectrum is shown in FIG. 12, where the solid black arrow indicates the δ 3 resonance that was selected for the correlation study.

As mentioned above, the correlation matrix and the covariance matrix (each p×q or q×p) were calculated. The correlation between the selected variable ($^{31}$P δ 3) of the first data set and all of the variables of the second data set (i.e., the range of $^1$H δ) is given in the column/row of the correlation matrix associated with this variable (i.e., the column/row for $^{31}$P δ 3). The covariance between this variable ($^{31}$P δ 3) and all of the variables of the second data set (i.e., the range of $^1$H δ) is given in the column/row of the covariance matrix associated with this variable (i.e., the column/row for $^{31}$P δ 3). This covariance (i.e., between $^{31}$P δ 3 and the range of $^1$H δ) was plotted as a function of the variable (i.e., $^1$H δ), and was colour coded according to the correlation. That is, each data point of the covariance plot was plotted in a colour that reflects the correlation of that variable (i.e., $^1$H δ) with the selected variable (i.e., $^{31}$P δ 3); specifically, red indicated a correlation of about 0.45 and blue indicated a correlation of 0. This plot (covariance versus $^1$H δ for about δ 2.8 to about δ 4.4, with correlation shown in colour) is shown in FIG. 13.

Figure 13:
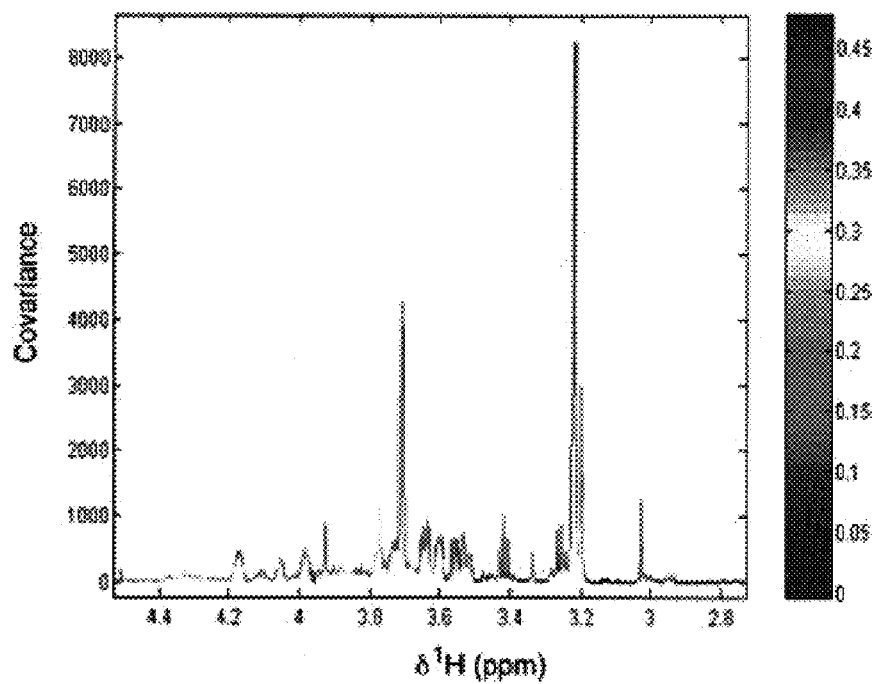
FIG. 13 is a plot of covariance versus $^1$H NMR chemical shift (δ, ppm), colour coded according to correlation with the $^{31}$P resonance at $^{31}$P δ 3, in a study of human gut tissue. See Study 5 below.

In FIG. 13, the peaks at δ 3.22, 3.6, and 4.18 are all highly correlated with the $^{31}$P δ 3. These peaks can be assigned to the choline headgroup of phosphatidylcholine, based on the literature, specifically, δ 3.22 may be assigned to N-trimethyl, δ 3.6 may be assigned to N—CH$_2$, and δ 4.18 may be assigned to O—CH$_2$.

Using these methods, it is possible to identify those parts of the $^1$H NMR spectra that are correlated with peaks in the $^{31}$P spectra (and assign those peaks to phosphatidylcholine), and in doing so, assign the featureless $^{31}$P NMR peak at about δ 3, which could not have been done otherwise.

These methods could be applied to in vivo, whole body spectroscopy (e.g., of the brain). For example, one could collect $^1$H and $^{31}$P spectra for localized regions inside the brain (of one subject, or a number of subjects; at one time-point, or a number of time-points), for example, a volume of (0.5 cm)$^3$ or (1 cm)$^3$, for example, of the grey matter, or of a tumour, and then perform correlation studies to identify the species within that volume, and, for example, diagnose the tumour and/or the type or severity of tumour, etc.

Study 5

A number of rats were dosed with 3-fluoroaniline (3-FA) at 50 mg/kg. Urine samples were collected over dry ice (i) pre-dose, (ii) after 0-24 hours, and (iii) after 24-48 hours. $^1$H NMR and $^1$H-decoupled $^{19}$F NMR spectra were collected. The collection of $^1$H NMR spectra was treated as a first data set (i.e., a matrix with one row for each $^1$H NMR spectrum, and one column for each $^1$H NMR chemical shift variable, n x p) and the collection of $^{19}$F-NMR spectra was treated as a second data set (i.e., a matrix with one row for each $^{19}$F NMR spectrum, and one column for each $^{19}$F NMR chemical shift variable, n×q). The correlation matrix and the covariance matrix (each p×q or q×p) were calculated.

There is little or no endogenous fluorine in mammals. Therefore, the peaks in the $^{19}$F NMR spectra may be assigned to 3-fluoroaniline and its fluorine-containing metabolites. But the $^{19}$F NMR spectra provide very little data that can be used to determine the chemical structure of the metabolites. The $^1$H NMR can provide this data, but only if those parts of the extremely complex spectra that correspond to the metabolites can be identified.

The $^{19}$F NMR spectra showed a resonance at δ-128.4 that can be assigned to the primary 3-fluoroaniline metabolite. This resonance was selected for the correlation study.

As mentioned above, the correlation matrix and the covariance matrix (each p×q or q×p) were calculated. The correlation between the selected variable ($^{19}$F δ-128.4) of the first data set and all of the variables of the second data set (i.e., the range of $^1$H δ) is given in the column/row of the correlation matrix associated with this variable (i.e., the column/row for $^{19}$F δ-128.4). The covariance between this variable ($^{19}$F δ-128.4) and all of the variables of the second data set (i.e., the range of $^1$H δ) is given in the column/row of the covariance matrix associated with this variable (i.e., the column/row for $^{19}$F δ-128.4). This covariance (i.e., between $^{19}$F δ-128.4 and the range of $^1$H δ) was plotted as a function of the variable (i.e., $^1$H δ), and was colour coded according to the correlation. That is, each data point of the covariance plot was plotted in a colour that reflects the correlation of that variable (i.e., $^1$H δ) with the selected variable (i.e., $^{19}$F δ-128.4); specifically, red indicated a correlation of 1 and blue indicated a correlation of 0. This plot (covariance versus $^1$H δ for about δ 6.2 to about δ 8, with correlation shown in colour) is shown in FIG. 14.

Figure 14:
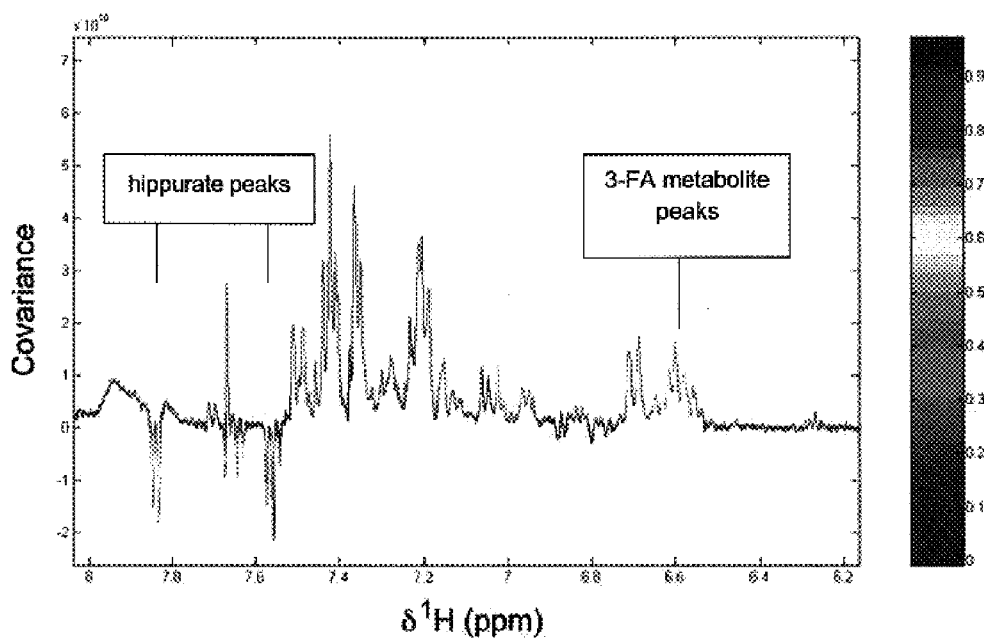
FIG. 14 is a plot of covariance versus $^1$H NMR chemical shift (δ, ppm), colour coded according to correlation with the $^{19}$F resonance at $^{19}$F δ-128.4, in a study of 3-fluoroaniline metabolism. The peaks assigned to the metabolite, N-acetyl-3-fluoroaniline-O-sulfate, are indicated. The peaks assigned to hippurate also indicated. See Study 5 below.

In FIG. 14, a number of peaks that are highly correlated to the $^{19}$F δ-128.4 resonance are visible (shown in orange to red). Those with positive covariance, specifically, those at about δ 7.05, δ 6.7, and δ 6.55-6.65, can be assigned to the protons of the 3-fluoroaniline metabolite. This information can be used to identify the metabolite as N-acetyl-3-fluoroaniline-O-sulfate, based on the literature.

In order to achieve this result using conventional NMR methods, it would be necessary to perform a time-consuming and complex $^{19}$F-$^1$H 2-dimensional correlation experiment based on a single sample. Here, simple experiments using $^1$H NMR and $^1$H-decoupled $^{19}$F NMR have been used with a number of samples, and the variation between the samples has been exploited in order to extract the connectivity, and thus the identity of the metabolite.

Also in FIG. 14, a number of the peaks that are highly correlated to the $^{19}$F δ-128.4 resonance have negative covariance, specifically, two doublets at about δ 7.55 and δ 7.85, and a triplet at about δ 7.65. Because of the negative covariance, these peaks cannot be assigned to the 3-fluoroaniline metabolite; instead, they can be assigned to another molecule, specifically, hippurate, based on the literature. Thus, this study also demonstrates that the 3-fluoroaniline is having an effect on endogenous metabolism, specifically, an effect that reduces the amount of hippurate (or hippuric acid). An increase in 3-fluoroaniline causes a decrease in hippurate levels. It is likely that this is due to a direct toxic effect of 3-fluoroaniline on the gut bacteria of the rats.

Study 6

Chromatography methods, when applied to complex mixtures, have limited value. Despite the separation, several species may elute at the same time (i.e., have the same retention time), and the associated detection methods (e.g., NMR, MS, UV-diode array) may not be able to distinguish between the different species.

Figure 15:
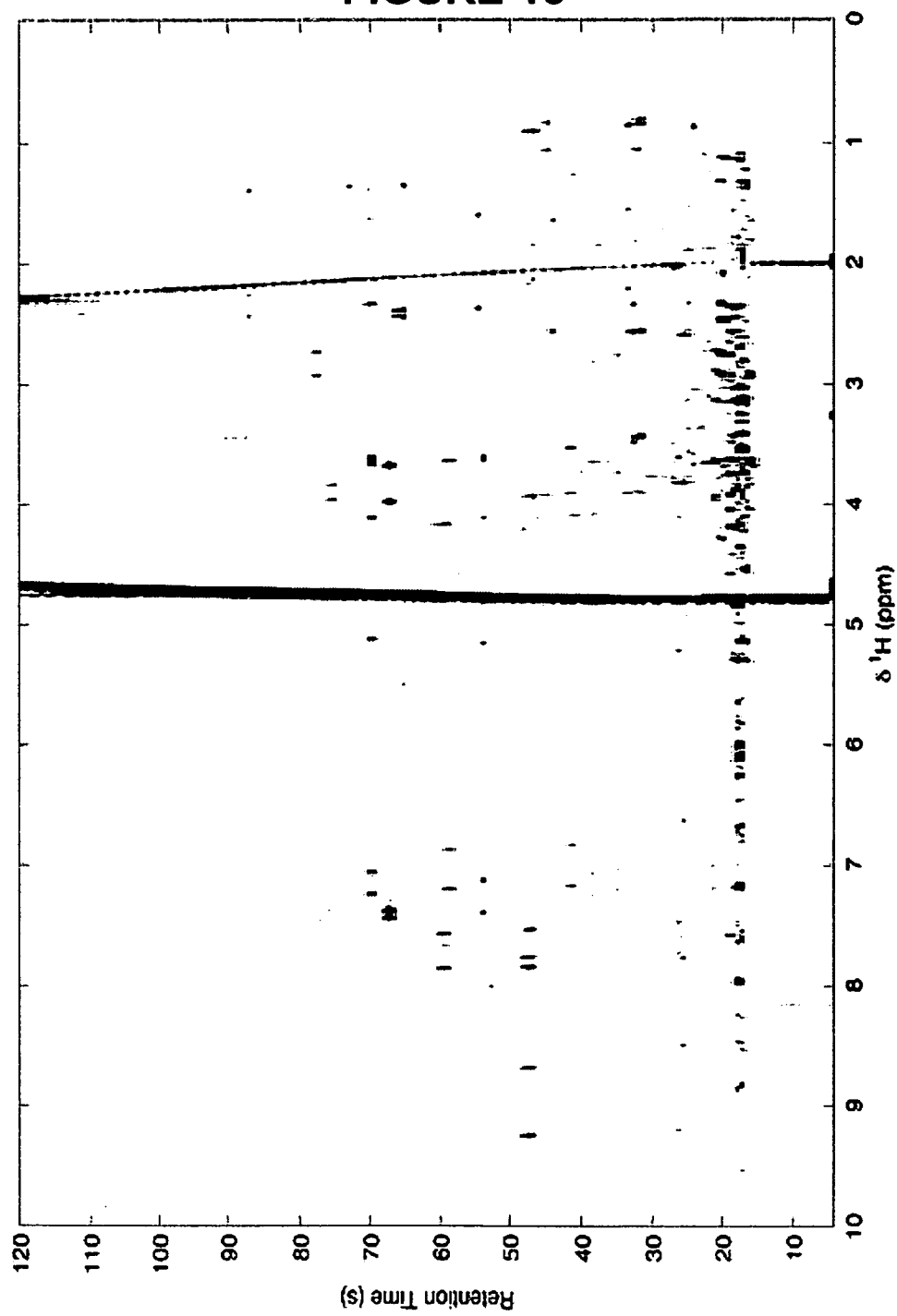
FIG. 15 is a contour plot of a set of $^1$H NMR spectra as a function of chemical shift, δ (ppm), and retention time (in seconds), with $^1$H NMR signal intensity indicated by colour (red indicates peaks), in an HPLC-NMR study of rat urine. See Study 6 below.

A rat urine sample was subjected to HPLC-NMR. $^1$H NMR spectra were recorded at a rate of about 1 spectrum per second, as a function of retention time. In FIG. 15, the $^1$H NMR spectra are plotted as a function of chemical shift, δ (ppm), and retention time (in seconds), with $^1$H NMR signal intensity indicated by colour (red indicates peaks). The broad peak at about δ 4.8, and the narrower peak at about δ 2, that are both present at all retention times are assigned to water and acetonitrile, respectively, of the elution system. The solvent front can be seen at about 18 seconds, where are large number of $^1$H NMR peaks can be seen, all associated with the very polar molecules in the mixture that are not separated by the chromatography. At later retention times, each "row" of $^1$H NMR peaks may be assigned those species eluting at that time.

Figure 16:
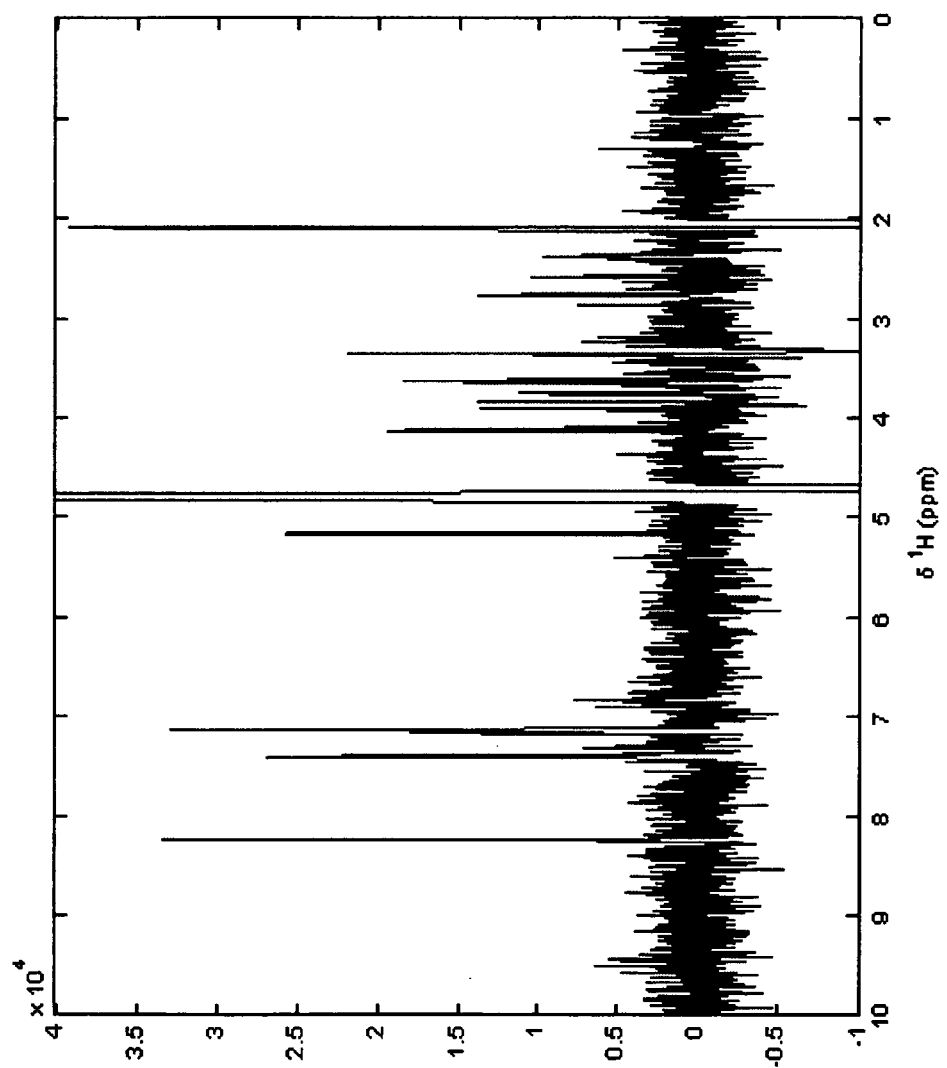
FIG. 16 is the $^1$H NMR spectrum recorded at a retention time of 54 seconds, in an HPLC-NMR study of rat urine. See Study 6 below.

As an example, the $^1$H NMR spectrum recorded at 54 second retention time is shown in FIG. 16. Again, the water and acetonitrile peaks are visible at about δ 4.8 and δ 2, respectively. A number of other peaks are visible, but the spectrum has a very low signal-to-noise ratio, and is of little value when attempting to assign the structure of the eluting species. The sharp peak at δ 7.14 (almost certainly associated with an aromatic proton) was selected for the correlation study.

The NMR peaks within each of the complex spectra should be correlated, because they are arise from the same species. Thus, the methods described herein may be used to determine that correlation and exploit it in order to identify the species in a particular elution.

Eleven (11) $^1$H NMR spectra were selected for use in the correlation study, specifically, the 5 spectra preceding 54 seconds, the five spectra following 54 seconds, and the spectrum at 54 seconds itself. This collection of spectra was treated as a single data set (i.e., a matrix with one row for each $^1$H NMR spectrum, and one column for each $^1$H NMR chemical shift variable). The correlation matrix and the covariance matrix were calculated.

Figure 17:
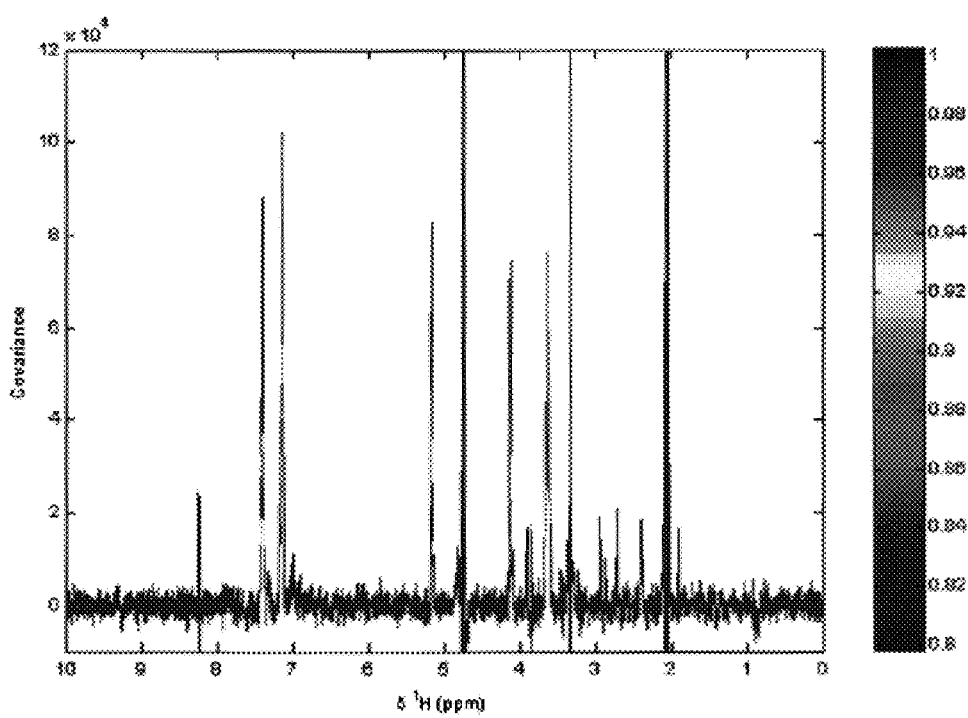
FIG. 17 is a plot of covariance versus $^1$H NMR chemical shift (δ, ppm), colour coded according to correlation with the $^1$H NMR resonance at δ 7.14. See Study 6 below.

As mentioned above, the peak at δ 7.14 in the spectrum for 54 seconds retention time was selected for the correlation study. The correlation between this variable (δ 7.14) and the other variables (i.e., the other chemical shifts) is given in the column of the correlation matrix associated with this variable (i.e., the column for δ 7.14). The covariance between this variable (δ 7.14) and the other variables (i.e., the other chemical shifts) is given in the column of the covariance matrix associated with this variable (i.e., the column for δ 7.14). This covariance (i.e., between δ 7.14 and the other chemical shifts) was plotted as a function of the variable (i.e., chemical shift), and was colour coded according to the correlation. That is, each data point of the covariance plot was plotted in a colour that reflects the correlation of that variable (i.e., chemical shift) with the selected variable (i.e., δ 7.14); specifically, red indicated a correlation of 1 and blue indicated a correlation of 0. This plot (covariance versus chemical shift, with correlation shown in colour) is shown in FIG. 17. (The figure shows a chemical range of about 0 to about 10.) The plot in FIG. 17 has a higher signal-to-noise ratio than the plot in FIG. 16, primarily because it reflects the data from 11 spectra, rather than only 1.

Figure 18:
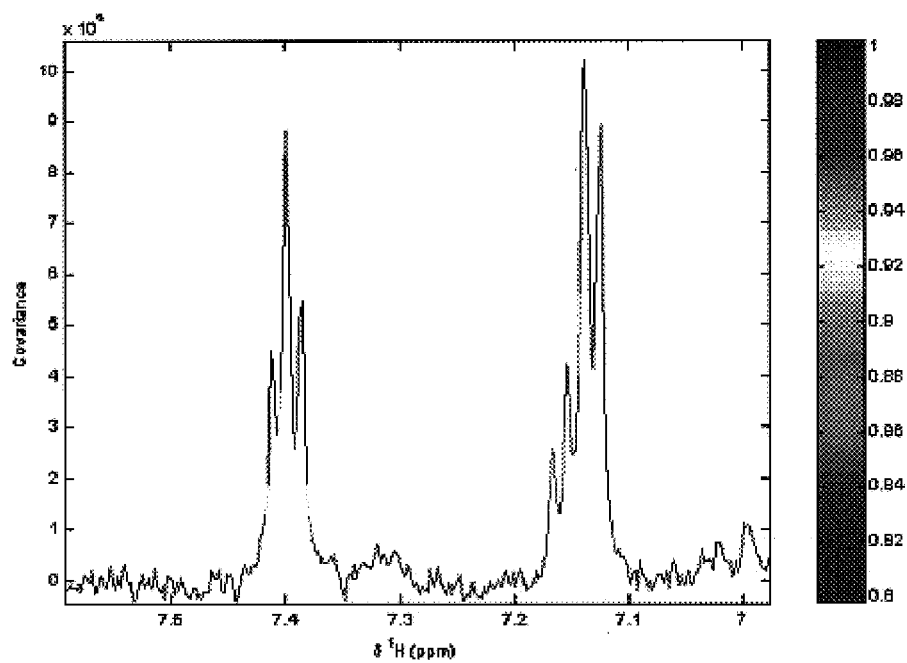
FIG. 18 is an expanded part of the plot shown in FIG. 17, showing characteristic peak chemical shifts and splittings for phenol glucuronide. See Study 6 below.
Figure 19:
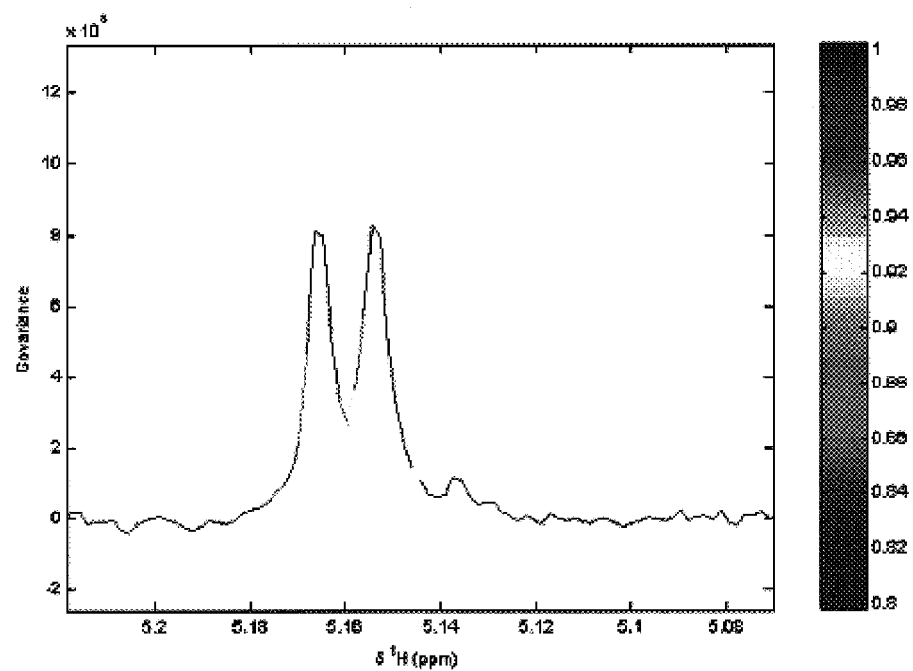
FIG. 19 is another expanded part of the plot shown in FIG. 17, showing characteristic peak chemical shifts and splittings for phenol glucuronide. See Study 6 below.
Figure 20:
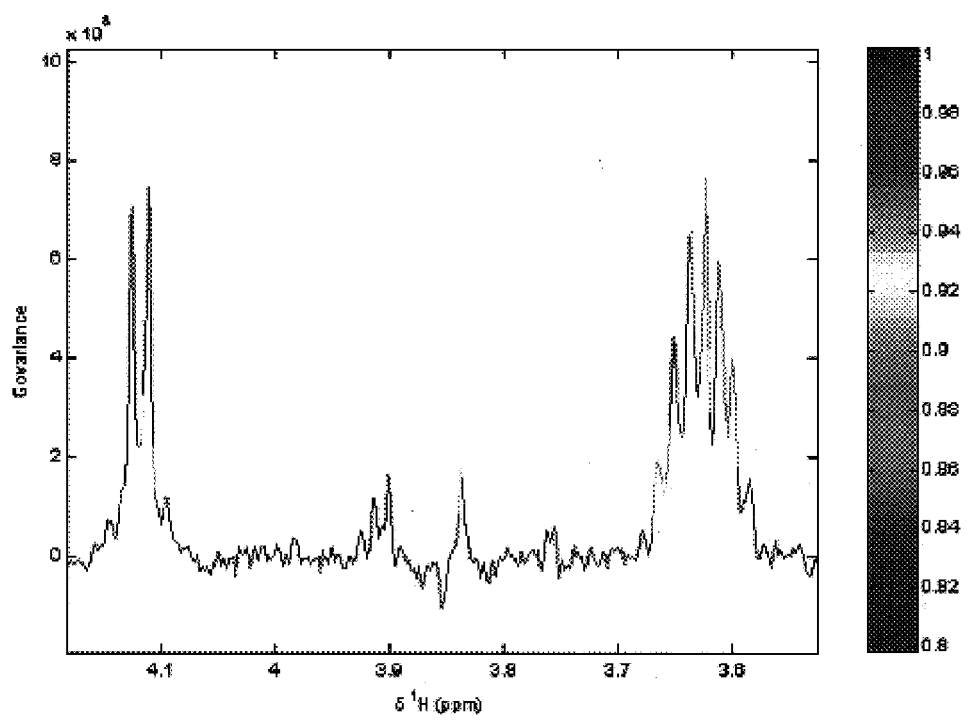
FIG. 20 is another expanded part of the plot shown in FIG. 17, showing characteristic peak chemical shifts and splittings for phenol glucuronide. See Study 6 below.

In FIG. 17, the peak at δ 7.14 is red, as expected, and is auto-correlated with itself. A number of other highly correlated (red) peaks are also visible. Each of FIG. 18, FIG. 19, and FIG. 20 shows an expanded region of FIG. 17 (δ 7.39 (triplet), δ 7.16 (triplet) overlapping with δ 7.13 (doublet); δ 5.16 (doublet); δ 4.12 (doublet); δ 3.63 (multiplet)). These highly correlated peaks are δ 7.13 and δ 7.16 (assigned to aromatic 3H and 1H of a phenol group), δ 7.39 (assigned to aromatic 2H of a phenol group), δ 5.16 (a doublet assigned to the anomeric H1 proton of glucuronide), δ 4.12 (assigned to H5 of glucuronide), and δ 3.63 (assigned to H2, H3, and H4 of glucuronide). (Assignments are based on the literature.)

Using these methods, it can be determined that one of the species eluting at a retention time of 54 seconds is phenol glucoronide, a bacterial metabolite from the gut of the rats. This information could not be obtained using HPLC-NMR methods alone.

This study demonstrates how the methods described herein can be used to overcome the limitation of chromatography, and especially chromatography with multivariate detection (e.g., NMR, MS, and/or UV-diode array detection). Even though many (if not many hundreds or thousands) of species may co-elute, and the associated data (e.g., NMR, MS, and/or UV spectra) may be very complex, it is possible to identify individual species within the co-eluting mixture by using the methods described herein. This might conveniently be described as a method of increasing or improving chromatographic resolution.

Study 7

The correlations between different types of multivariate data may be determined in an effort to identify the underlying chemical species. It is possible to correlate the output of different types of spectroscopies, applied to the same samples, in order to reveal latent biomarkers and biological relationships. This approach is often referred to as Statistical Heterospectroscopy (SHY). In this study, NMR and mass spectrometry (MS) data are used together in order to identify the species present (in this case, biomarkers for hydrazine poisoning).

A number of rats were dosed with hydrazine. Urine samples were collected. $^1$H NMR and mass spectra were recorded for each sample. (Note that the mass spectra were recorded using an UPLC-MS experiment, in which individual mass spectra are recorded as function of elution time, here over a period of six minutes with a water-acetonitrile gradient; however, for the present study, these spectra were "summed" in order to present a single mass spectrum for each sample. This gives, in effect, "virtual direct injection mass spectra." This is a known approach for improving MS detection in complex mixtures.)

Figure 21:
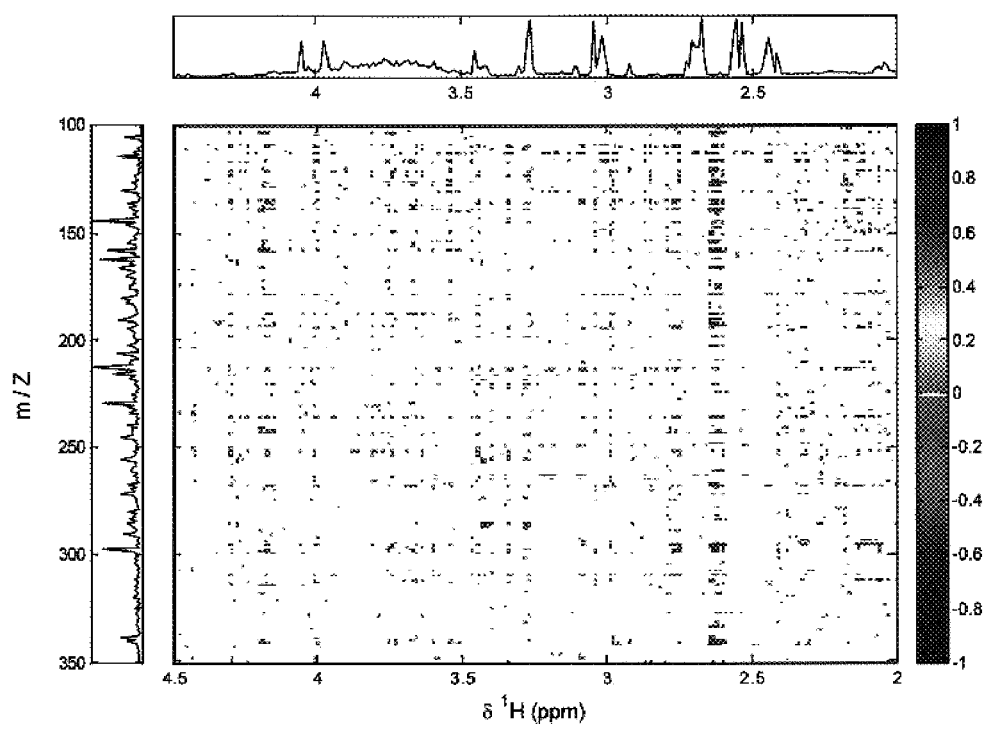
FIG. 21 is a correlation map illustrating the correlation, as indicated by colour (from blue for correlation −1 to red for correlation +1), as a function of both m/z (along the vertical axis) and $^1$H chemical shift (along the horizontal axis), in a study of hydrazine poisoning. A "summed" $^1$H NMR spectrum is shown alongside the $^1$H δ axis for illustration. Similarly, a "summed" mass spectrum is shown alongside the m/z axis for illustration. See Study 7 below.

The collection of $^1$H NMR spectra was treated as a first data set (i.e., a matrix with one row for each $^1$H NMR spectrum, and one column for each $^1$H NMR chemical shift variable, n×p) and the collection of mass spectra was treated as a second data set (i.e., a matrix with one row for each mass spectrum, and one column for each m/z variable, n×q). The correlation matrix and the covariance matrix (each p×q or q×p) were calculated. A correlation map illustrating a part of the correlation matrix, as a function of both $^1$H chemical shift (from about δ 2 to about δ 4.5) and m/z (from about 100 to about 350), is shown in FIG. 21. The correlation is indicated by colour (blue is negative correlation and red is positive correlation). A "summed" $^1$H NMR spectrum is shown alongside the $^1$H δ axis for illustration. Similarly, a "summed" mass spectrum is shown alongside the m/z axis for illustration.

Highly correlated points (red points) in the correlation map indicate a correlation between that $^1$H NMR chemical shift (a peak in the NMR spectrum) and that m/z value (a molecular weight). For example, two points of high correlation are visible at about m/z 110 and δ 3, and m/z 110 and δ 2.45. This indicates that these two NMR peaks (δ 3 and δ 2.45) are correlated with an ion having a molecular weight of 110. This provides additional structural information that can be exploited in order to determine the identity of the underlying chemical species.

Highly anti-correlated points (blue points) in the correlation map indicate a strong negative correlation between that $^1$H NMR chemical shift (a peak in the NMR spectrum) and that m/z value (a molecular weight). For example, a point of strong negative correlation is visible at about m/z 140 and δ 3.1. This indicates that when the species associated with the peak at δ 3.1 increases, the species associated with m/z 140 decreases. This provides additional information about biochemical pathways.

Figure 22:
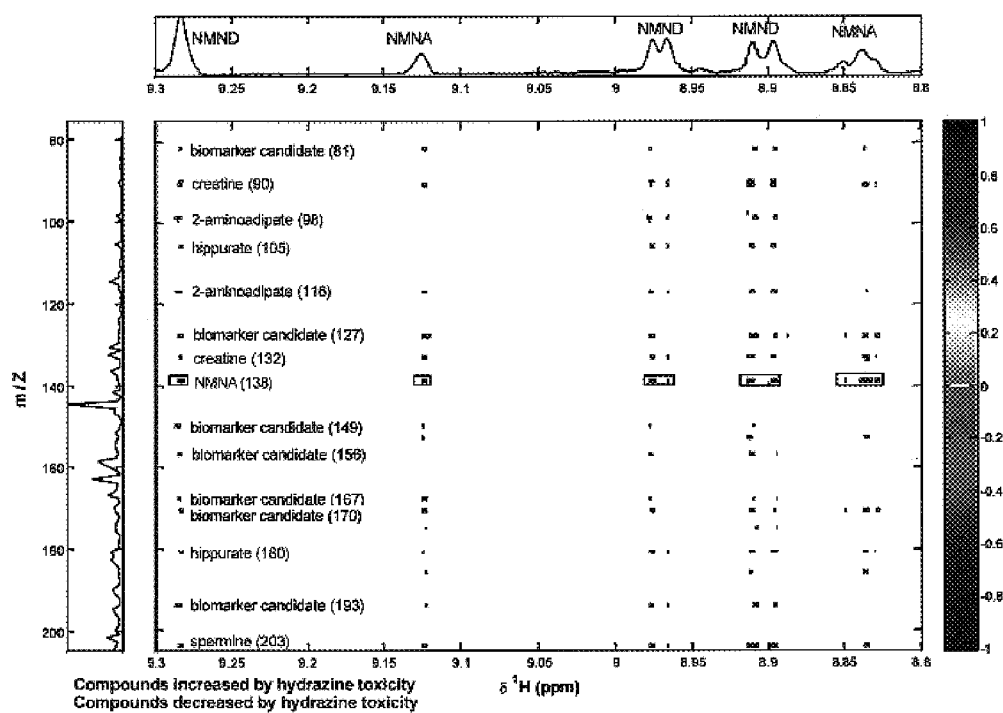
FIG. 22 is another correlation map illustrating the correlation, as indicated by colour (from blue for correlation −1 to red for correlation +1), as a function of both m/z (along the vertical axis) and $^1$H chemical shift (along the horizontal axis), in a study of hydrazine poisoning. A "summed" $^1$H NMR spectrum is shown alongside the $^1$H δ axis for illustration. Similarly, a "summed" mass spectrum is shown alongside the m/z axis for illustration. See Study 7 below.

A correlation map illustrating another (very small) part of the correlation matrix is shown in FIG. 22, specifically for $^1$H chemical shift from about δ 8.8 to about δ 9.3 and m/z from about 80 to about 200. Again, a "summed" $^1$H NMR spectrum is shown alongside the $^1$H δ axis for illustration. Similarly, a "summed" mass spectrum is shown alongside the m/z axis for illustration. The $^1$H NMR spectrum shows five peaks that are assigned to two known markers of hydrazine poisoning: N-methylnicotinamide (NMND) and N-methylnicotinic acid (NMNA). As expected, the mass spectrum peak at m/z 138 (for NMNA) is highly correlated with the $^1$H NMR peaks at about δ 9.12 about δ 8.84 (also for NMNA). Also as expected, the mass spectrum peak at m/z 138 (for NMNA) is highly anti-correlated with the $^1$H NMR peaks at about δ 9.28, about δ 8.97, and about δ 8.9 (for NMND). (It is well known that hydrazine poisoning causes an decrease in NMNA and a concurrent increase in NMND.) A number of other species are also assigned to the various m/z "rows", on the basis of the m/z value and the associated highly correlated (or, alternatively, highly anti-correlated) $^1$H NMR δ values. For example, creatine (m/z 90, m/z 116) and 2-aminoadipate (m/z 98, m/z 116) are identified, and are shown to be affected in the same way as NMND, that is, they are increased by hydrazine poisoning. Similarly, hippurate (m/z 105, m/z 180) is identified, and is shown to be affected in the same way as NMNA, that is, it is decreased by hydrazine poisoning. These are known biomarkers for hydrazine poisoning. A number of other (as yet unknown) biomarker candidates are also visible, but their complete assignment has not been made (m/z 81, 127, 149, 156, 167, 170, 193). One new biomarker, spermine (m/z 203), has been identified on the basis of the m/z value and the associated $^1$H NMR δ values. It was not previously known that spermine was a biomarker for hydrazine poisoning.

Since any metabolite that correlates with a biomarker is itself a biomarker (e.g., a surrogate biomarker), this approach facilitates rapid biomarker candidate discovery. By applying the technique to other data exhibiting only normal biological variation (rather than variation driven by toxic response), it is possible to find groups of metabolites that co-vary naturally, and are therefore are likely to be related to the same pathway.

As discussed above, this study employed virtual direct injection mass spectra, obtained by integrating mass spectra over retention time, and thereby losing any associated information. However, it is possible to integrate over a subset of retention time, giving a filtered output that provides additional information that can contribute to biomarker identification. Indeed, with enough computational power, it would be possible to retain all of the retention time information, and the results could then be displayed in a 3-dimensional correlation map, characterised by axes of chemical shift, m/z, and retention time, with correlation indicated by the colour of each point within that 3-dimensional space.

In the same way that a collection of NMR spectra can be analysed in order to identify those NMR peaks that are correlated, and thus help with chemical structure determination, mass spectral data can be analysed in order to identify those m/z peaks that are correlated (e.g., reflect fragments of the same parent species), again to help with chemical structure determination. This approach may conveniently be referred to as STAMSY.

Figure 23:
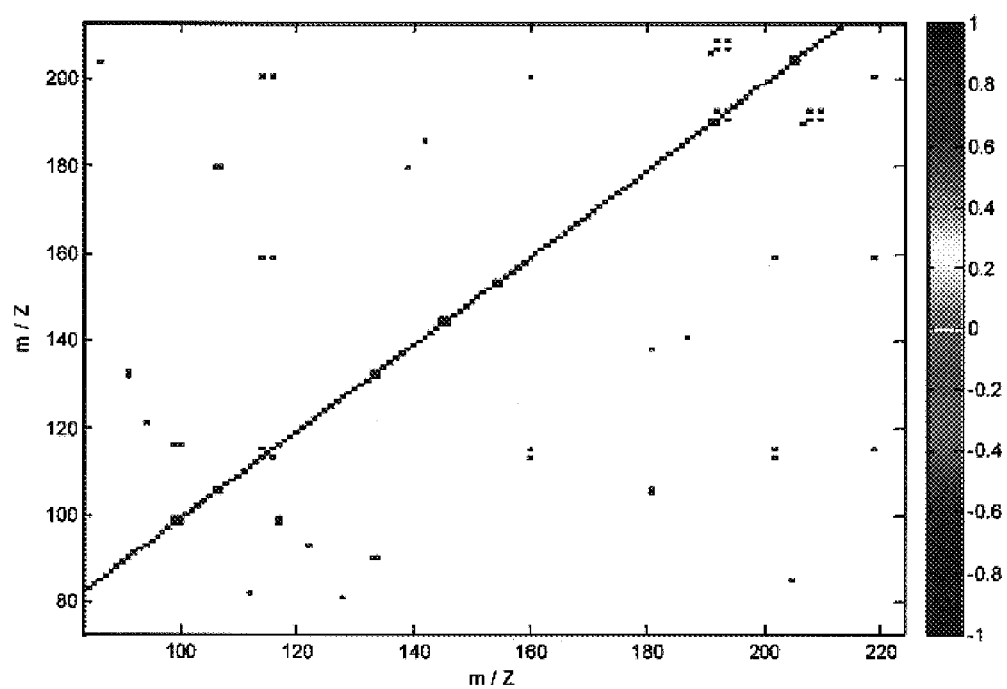
FIG. 23 is a correlation map illustrating the correlation within the mass spectral data, as indicated by colour (from blue for correlation −1 to red for correlation +1; for convenience, only those points with a correlation of 0.6 or greater (red) are shown), as a function of m/z (along both the vertical and the horizontal axis), in a study of hydrazine poisoning. See Study 7 below.

Here, the collection of mass spectra described above was treated as the only data set (i.e., a matrix with one row for each mass spectrum, and one column for each m/z variable, n×p). The correlation matrix and the covariance matrix (each p×p) were calculated. The calculation was filtered so that correlations between peaks at different retention times were ignored. A correlation map illustrating a part of the correlation matrix is shown in FIG. 23. The correlation is indicated by colour (blue is −1 correlation; green is 0 correlation; and red is +1 correlation), as a function of m/z along each axis (from about 100 to about 220, and from about 80 to about 200). For convenience, only those points with a correlation of 0.6 or greater (red) are shown. The diagonal line (y=x) reflects the auto-correlation of each m/z with itself. Points of high correlation off the diagonal indicate correlation between two fragments. For example, at m/z about 108 and m/z about 180, there is a point of high correlation. This indicates that the mass spectrum peaks at these two m/z values are highly correlated, and may represent, for example, parent ion and fragment ion, or two fragments originating from the same parent ion.

In this study, several of the off-diagonal peaks correspond to parent ions of known hydrazine-toxicity biomarkers, but most of the off-diagonal peaks indicate fragments of these parents resulting from ion-source fragmentation. With this information, in the search for new biomarkers, one can avoid wasting time trying to identify (e.g., by other means) peaks that are now known to correspond to fragments of known biomarkers, rather than new biomarker candidates.

In this approach, filtering so as to ignore correlations of peaks at the same retention time, allows distinct co-varying metabolites to be highlighted. This could provide biomarker candidates that are different from those identified using SHY methods on NMR and LC-MS data, described earlier, because the different physical basis of the two analytical techniques tends to cause the metabolites detected by them to be complementary.

Study 8

As another example of methods applied to different types of multivariate data, both NMR and proteomic data were analysed in order to determine associations between proteins and metabolites.

Mice were implanted with a prostate cancer (PC-3) xenograft as a human tumour xenograft mouse model of prostate cancer. Plasma samples were collected from the xenograft mice as well as matched control animals and $^1$H NMR recorded for each sample, and on the same samples, 2D-DIGE (fluorescent 2-D differential gel electrophoresis) proteomic studies were performed.

Figure 24:
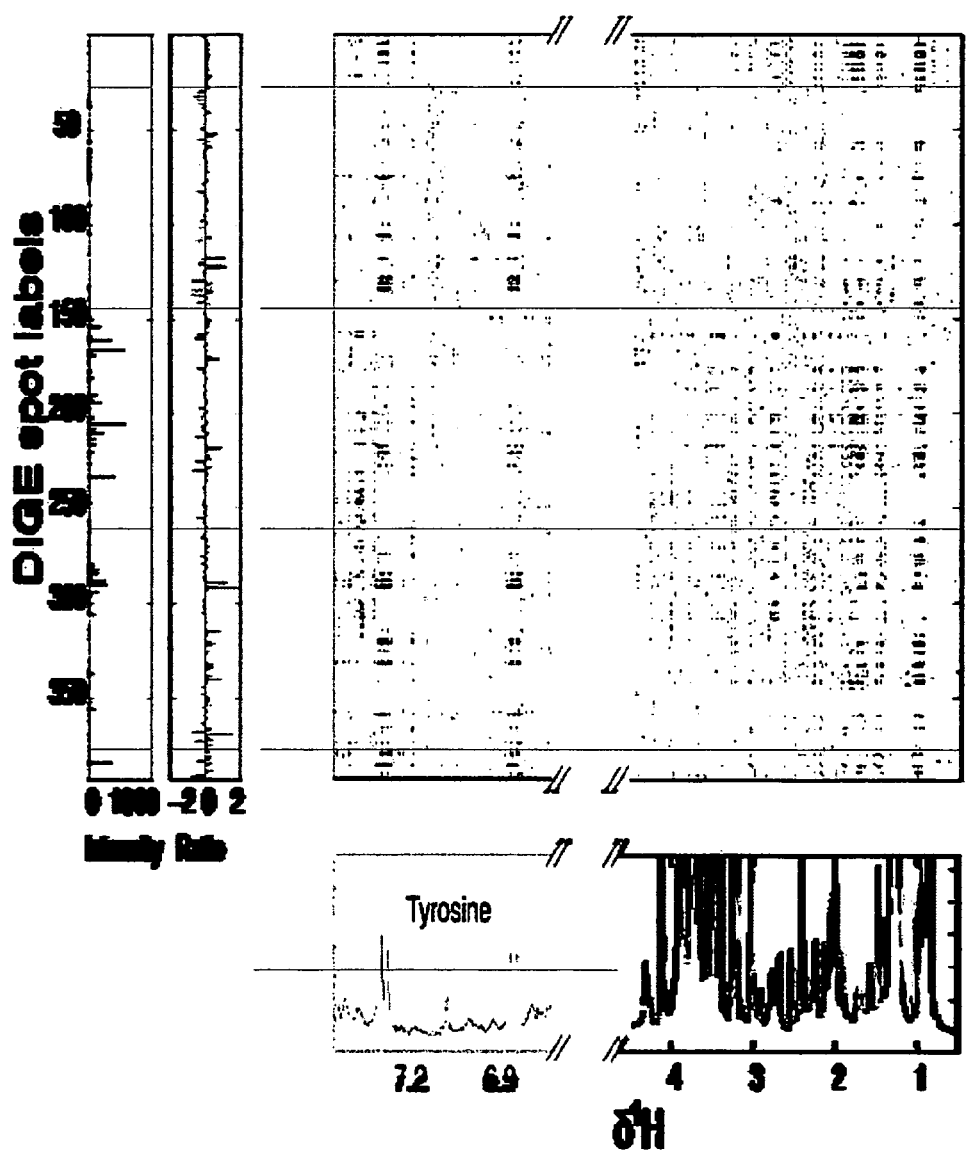
FIG. 24 is a correlation map illustrating the correlation, as indicated by colour (from blue for negative correlation to red for positive correlation), as a function of both DIGE spot label and $^1$H chemical shift, in an NMR-proteomic study of a human tumour xenograft mouse model of prostate cancer. For convenience, only correlations of >+0.77 or <−0.77 are shown. See Study 8 below.

The collection of $^1$H NMR spectra was treated as a first data set (i.e., a matrix with one row for each $^1$H NMR spectrum (i.e., for each sample), and one column for each $^1$H NMR chemical shift variable, n×p) and the collection of DIGE data was treated as a second data set (i.e., a matrix with one row for the DIGE data for each sample, and one column for each spot label, n×q). The correlation matrix and the covariance matrix (each p×q or q×p) were calculated. A correlation map illustrating a part of the correlation matrix, as a function of both DIGE spot label (from 0 to 400) and 1 H chemical shift (from about δ 6.9 to about δ 7.2 and from about δ 1 to about δ 4) is shown in FIG. 24. The correlation is indicated by colour (blue is −1 correlation; green is 0 correlation; and red is +1 correlation). For convenience, only correlations of >+0.77 or <−0.77 are shown.

A representative $^1$H NMR spectrum is shown alongside the $^1$H δ axis for illustration. The colour coding in this spectrum indicates peaks that are changed upon xenograft implantation (from red—indicating most change—to blue—indicating least change). Similarly, a representative DIGE "spectrum" (of DIGE spot density (e.g., protein level) versus DIGE spot label (e.g., indicating a particular protein) is shown alongside the DIGE spot label axis for illustration. Again, the colour coding in this spectrum indicates spots (proteins) that are changed upon xenograft implantation (from red—indicating most change—to blue—indicating least change).

Spots within the correlation map may be used to link features in the NMR spectra with particular proteins in the DIGE array. For example, the NMR resonances at about δ 6.85 and δ 7.3 correspond to tyrosine in the blood plasma samples (based on the literature). These resonances (and thus tyrosine) are substantially changed upon xenograft implantation. Tyrosine is also highly correlated with a number of the proteins indicated by DIGE spot labels, for example, the protein indicated by a DIGE spot label number of about 295.

Indeed, multiple correlations between metabolites and proteins are indicated, including associations between serotransferrin precursor and both tyrosine and 3-D-hydroxybutyrate. Additionally, a correlation between decreased plasma levels of tyrosine and increased presence of gelsolin was also observed.

This approach can greatly improve both the speed and accuracy of identification of biomarkers across multi-omic platforms (e.g., metabonomics, proteomics, transcriptomics, genomics), thus enhancing understanding of in vivo model systems.

Study 9

As yet another example of methods applied to different types of multivariate data, both NMR and transcriptomic data were analysed.

Two strains of mouse were studied: a wild-type and an insulin resistance knock-out strain (IRS-2). These mice show no metabolic distinctions at 5 weeks of age, based on transcriptomics, or metabonomics (based on $^1$H NMR spectra of blood serum). At 8 weeks of age, different transcriptomic profiles distinguish the two strains. Similarly, metabonomic differences also allow classification of the two strains. By analysing the transcriptomic data in combination with the NMR data, it is possible to determine which changes in gene expression relate to which changes in the levels of metabolites.

Blood plasma samples were collected from the two strains of mice and $^1$H NMR recorded for each sample. Tissue samples were also collected from the two strains of mice, and transcriptomic studies were performed using a microarray.

The collection of $^1$H NMR spectra was treated as a first data set (i.e., a matrix with one row for each $^1$H NMR spectrum (i.e., for each sample), and one column for each $^1$H NMR chemical shift variable, n×p) and the collection of transcriptomic data was treated as a second data set (i.e., a matrix with one row for the transcriptomic data for each sample, and one column for each transcriptomic label, n×q). The correlation matrix and the covariance matrix (each p×q or q×p) were calculated. Gene expression for the gene coding for apolipoprotein A1 was selected for the correlation study.

Figure 25:
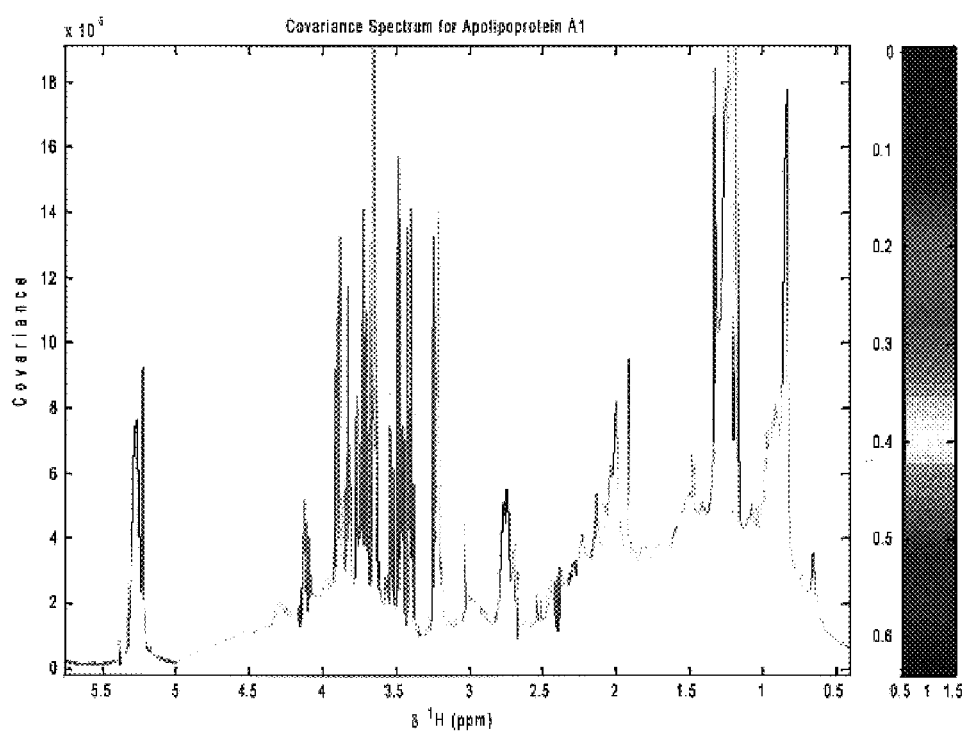
FIG. 25 is a plot of covariance versus $^1$H NMR chemical shift (δ, ppm), colour coded according to correlation with Apolipoprotein A1 gene expression, in a study of wild-type and insulin resistance knock-out (IRS-2) mice. See Study 9 below.

The correlation between the selected variable (apolipoprotein A1) of the first data set and all of the variables of the second data set (i.e., the range of $^1$H δ) is given in the column/row of the correlation matrix associated with this variable (i.e., the column/row for apolipoprotein A1). The covariance between this variable (apolipoprotein A1) and all of the variables of the second data set (i.e., the range of $^1$H δ) is given in the column/row of the covariance matrix associated with this variable (i.e., the column/row for apolipoprotein A1). This covariance (i.e., between apolipoprotein A1 and the range of $^1$H δ) was plotted as a function of the variable (i.e., $^1$H δ), and was colour coded according to the correlation. That is, each data point of the covariance plot was plotted in a colour that reflects the correlation of that variable (i.e., $^1$H δ) with the selected variable (i.e., apolipoprotein A1); specifically, red indicated a correlation of about 0.6 and blue indicated a correlation of 0. This plot (covariance versus $^1$H δ for about δ 0.5 to about δ 5.5, with correlation shown in colour) is shown in FIG. 25.

Several highly correlated (red) peaks are visible, specifically, at about δ 5.3, 3.7, 2.7, 1.9, 1.1, and 0.7. These can be assigned to the fatty acyl groups of lipoproteins, based on the literature. This study indicates that the main metabolic consequence of this difference in gene expression is in the lipoprotein levels.

This study demonstrates that is it possible to find correlations between changes in plasma metabolite levels, as measured using NMR, and changes in gene expression, and to use these correlations to better understand that biological processes involved. For example, it is possible to link changes in expression of a gene with the associated biochemical changes in blood plasma.

The foregoing has described the principles, preferred embodiments, and modes of operation of the present invention. However, the invention should not be construed as limited to the particular embodiments discussed herein. Instead, the above-described embodiments should be regarded as illustrative rather than restrictive, and it should be appreciated that variations may be made in those embodiments by workers skilled in the art without departing from the scope of the present invention.

The invention claimed is:

1. A method of identifying a sample constituent of a sample, the method comprising the steps of:
   (a) providing a plurality of spectra defining a first set of spectra, wherein each spectrum of said set of spectra is a spectrum of measurement values derived from different measurements of a property of a sample comprising said sample constituent, each measurement value corresponding to one of a range of measurement variables defining the spectrum;

(b) providing a plurality of spectra defining a second set of spectra, wherein each spectrum of said set of spectra is a spectrum of measurement values derived from different measurements of a property of a sample comprising said sample constituent, each measurement value corresponding to one of a range of measurement variables defining the spectrum;

(c) generating a measure of the correlation between: each spectrum of measurement values in the first set of spectra and each spectrum of measurement values in the second set of spectra;

(d) generating association data through which a particular measurement variable in any spectrum of the first set of spectra, and a particular measurement variable in any spectrum of the second set of spectra, is associated to the measure of correlation between: the measurement values of the respective given measurement variables;

(e) identifying said sample constituent using the measure of correlation and the association data.

2. A method according to claim 1, wherein said first set of spectra and said second set of spectra are identical.

3. A method according to claim 1, wherein said first set of spectra and said second set of spectra are different.

4. A method according to claim 1, wherein said plurality of spectra defining a first set of spectra is at least 5, and said plurality of spectra defining a second set of spectra is at least 5.

5. A method according to claim 1, wherein for said first set of spectra and/or said second set of spectra, said measurement values are NMR signal intensities, said property is NMR signal, and said measurement variables are NMR chemical shifts or surrogates therefor.

6. A method according to claim 1, wherein for said first set of spectra and said second set of spectra, said measurement values are NMR signal intensities, said property is NMR signal, and said measurement variables are NMR chemical shifts or surrogates therefor.

7. A method according to claim 1, wherein for said first set of spectra and/or for said second set of spectra, said measurement values are mass spectral intensities, said property is mass spectral ion signal, and said measurement variables are mass-to-charge ratios or surrogates therefor.

8. A method according to claim 1, wherein for said first set of spectra and/or for said second set of spectra, said measurement values are infrared absorption values, said property is infrared absorption, and said measurement variables are wave numbers or surrogates therefor.

9. A method according to claim 1, wherein for said first set of spectra and/or for said second set of spectra, said measurement values are ultraviolet absorption values, said property is ultraviolet absorption, and said measurement variables are wavelengths or surrogates therefor.

10. A method according to claim 1, wherein for said first set of spectra and/or for said second set of spectra, said measurement values are metabolite levels, said property is amount of metabolite, and said measurement variables are names or labels associated with the metabolites, or surrogates therefor.

11. A method according to claim 1, wherein for said first set of spectra and/or for said second set of spectra, said measurement values are protein levels, said property is amount of protein, and said measurement variables are names or labels associated with the proteins, or surrogates therefor.

12. A method according to claim 1, wherein for said first set of spectra and/or for said second set of spectra, said measurement values are gene expression levels, said property is amount of gene expression, and said measurement variables are names or labels associated with the genes, or surrogates therefor.

13. A method according to claim 1, wherein for said first set of spectra and/or for said second set of spectra, said measurement values are indicators of presence or absence of genes, said property is presence or absence of the genes, and said measurement variables are names or labels associated with the genes, or surrogates therefor.

14. A method of identifying a sample constituent of a sample, the method comprising the steps of:

(a) providing a plurality of spectra defining a first set of spectra, wherein each spectrum of said set of spectra is a spectrum of measurement values derived from different measurements of a property of a sample comprising said sample constituent, each measurement value corresponding to one of a range of measurement variables defining the spectrum;

(b) providing a plurality of spectra defining a second set of spectra, wherein each spectrum of said set of spectra is a spectrum of measurement values derived from different measurements of a property of a sample comprising said sample constituent, each measurement value corresponding to one of a range of measurement variables defining the spectrum;

(c) selecting a measurement variable of interest from a spectrum of the first set of spectra; and (d) generating a measure of the correlation between: the measurement values in the spectra of the first set of spectra corresponding to the measurement variable of interest, and measurement values corresponding to some or all of the measurement variables in the spectra of the second set of spectra;

(e) generating association data through which the measurement variable of interest in any spectrum of the first set of spectra, and a measurement variable in any spectrum of the second set of spectra is associated to the measure of correlation between: the measurement values of the respective measurement variables;

(f) identifying said sample constituent using the measure of correlation and the association data.

15. A method according to claim 14, wherein said first set of spectra and said second set of spectra are identical.

16. A method according to claim 14, wherein said first set of spectra and said second set of spectra are different.

17. A method according to claim 14, wherein said plurality of spectra defining a first set of spectra is at least 5, and said plurality of spectra defining a second set of spectra is at least 5.

18. A method according to claim 14, wherein for said first set of spectra and/or said second set of spectra, said measurement values are NMR signal intensities, said property is NMR signal, and said measurement variables are NMR chemical shifts or surrogates therefor.

19. A method according to claim 14, wherein for said first set of spectra and said second set of spectra, said measurement values are NMR signal intensities, said property is NMR signal, and said measurement variables are NMR chemical shifts or surrogates therefor.

20. A method according to claim 14, wherein for said first set of spectra and/or for said second set of spectra, said measurement values are mass spectral intensities, said property is mass spectral ion signal, and said measurement variables are mass-to-charge ratios or surrogates therefor.

21. A method according to claim 14, wherein for said first set of spectra and/or for said second set of spectra, said measurement values are infrared absorption values, said property is infrared absorption, and said measurement variables are wave numbers or surrogates therefor.

22. A method according to claim 14, wherein for said first set of spectra and/or for said second set of spectra, said measurement values are ultraviolet absorption values, said property is ultraviolet absorption, and said measurement variables are wavelengths or surrogates therefor.

23. A method according to claim 14, wherein for said first set of spectra and/or for said second set of spectra, said measurement values are metabolite levels, said property is amount of metabolite, and said measurement variables are names or labels associated with the metabolites, or surrogates therefor.

24. A method according to claim 14, wherein for said first set of spectra and/or for said second set of spectra, said measurement values are protein levels, said property is amount of protein, and said measurement variables are names or labels associated with the proteins, or surrogates therefor.

25. A method according to claim 14, wherein for said first set of spectra and/or for said second set of spectra, said measurement values are gene expression levels, said property is amount of gene expression, and said measurement variables are names or labels associated with the genes, or surrogates therefor.

26. A method according to claim 14, wherein for said first set of spectra and/or for said second set of spectra, said measurement values are indicators of presence or absence of genes, said property is presence or absence of the genes, and said measurement variables are names or labels associated with the genes, or surrogates therefor.

27. A method of identifying a plurality of biologically correlated sample constituents of a sample, the method comprising the steps of:
    (a) providing a plurality of spectra defining a first set of spectra, wherein each spectrum of said set of spectra is a spectrum of measurement values derived from different measurements of a property of a sample comprising said first sample constituent and said second sample constituent, each measurement value corresponding to one of a range of measurement variables defining the spectrum;
    (b) providing a plurality of spectra defining a second set of spectra, wherein each spectrum of said set of spectra is a spectrum of measurement values derived from different measurements of a property of a sample comprising said first sample constituent and said second sample constituent, each measurement value corresponding to one of a range of measurement variables defining the spectrum;
    (c) generating a measure of the correlation between: each spectrum of measurement values in the first set of spectra and each spectrum of measurement values in the second set of spectra;
    (d) generating association data through which a particular measurement variable in any spectrum of the first set of spectra, and a particular measurement variable in any spectrum of the second set of spectra, is associated to the measure of correlation between: the measurement values of the respective given measurement variables;
    (e) identifying said plurality of biologically correlated sample constituents using the measure of correlation and the association data.

28. A method of identifying a class-discriminant chemical species for a particular class membership, comprising the steps of:
    (a) providing a data set that comprises a plurality of data vectors for each of a plurality of classes,
    each data vector comprising, at least, a spectrum and a class representation variable,
    wherein said spectrum comprises measurement values derived from different measurements of a property of a sample representative of one of said plurality of classes,
    each measurement value corresponding to one of a range of measurement variables;
    (b) modelling said data set using a supervised mathematical model;
    (c) calculating the degree of correlation between: measurement variables and class representation variables of the supervised mathematical model;
    (d) identifying class-discriminant measurement variables as those measurement variables that are correlated with the particular class, thereby being discriminant for the particular class;
    (e) selecting a class-discriminant measurement variable of interest according to the degree of correlation with the particular class;
    (f) generating a measure of the correlation between: the measurement value of the class-discriminant measurement variable of interest, and measurement values corresponding to some or all of the other measurement variables,
    (g) identifying correlated measurement variables of measurement values that are relatively highly correlated with the measurement value of the class-discriminant measurement variable of interest;
    (h) identifying said class-discriminant chemical species for the particular class membership using said correlated measurement variables.

* * * * *